US010258230B2

(12) United States Patent
Rotenstreich

(10) Patent No.: US 10,258,230 B2
(45) Date of Patent: Apr. 16, 2019

(54) PUPILLOMETERS AND SYSTEMS AND METHODS FOR USING A PUPILLOMETER

(71) Applicant: Tel HaShomer Medical Research Infrastructure and Services Ltd., Ramat Gan (IL)

(72) Inventor: Ygal Rotenstreich, Kfar Bilu (IL)

(73) Assignee: Tel Hashomer Medical Research Infrastructure and Services, Ltd., Ramat Gan (IL)

(*) Notice: Subject to any disclaimer, the term of this patent is extended or adjusted under 35 U.S.C. 154(b) by 157 days.

(21) Appl. No.: 15/031,842

(22) PCT Filed: Oct. 30, 2014

(86) PCT No.: PCT/IB2014/002922
§ 371 (c)(1),
(2) Date: Apr. 25, 2016

(87) PCT Pub. No.: WO2015/063598
PCT Pub. Date: May 7, 2015

(65) Prior Publication Data
US 2016/0262611 A1    Sep. 15, 2016

Related U.S. Application Data

(60) Provisional application No. 61/897,494, filed on Oct. 30, 2013.

(51) Int. Cl.
A61B 3/00    (2006.01)
A61B 3/14    (2006.01)
(Continued)

(52) U.S. Cl.
CPC ............ *A61B 3/112* (2013.01); *A61B 3/0008* (2013.01); *A61B 3/0025* (2013.01);
(Continued)

(58) Field of Classification Search
CPC ......... A61B 3/112; A61B 3/14; A61B 3/0025; A61B 3/0058; A61B 3/0008; A61B 3/11;
(Continued)

(56) References Cited

U.S. PATENT DOCUMENTS 4,755,043 A    7/1988 Carter
5,114,222 A    5/1992 Cornsweet
(Continued)

OTHER PUBLICATIONS

Skaat et al., "Pupillometer-Based Objective Chromatic Perimetry in Normal Eyes and Patients with Retinal Photoreceptor Dystrophies", Invest Ophthalmol Vis Sci., 17;54(4), pp. 2761-2770, Apr. 2013.
(Continued)

Primary Examiner — Brandi Thomas
(74) Attorney, Agent, or Firm — Dinsmore & Shohl LLP

(57) ABSTRACT

In one embodiment, a portable pupillometer including a testing compartment, at least one ocular disposed on the testing compartment, two or more light sources disposed in the testing compartment and forming a plurality of visual stimuli for a subject looking through the at least one ocular, at least one camera configured to capture images of a pupil of the subject via infrared detection, the images indicating pupillary responses to the two or more light sources, and an interface for connection with a computing device external to the pupillometer, the interface adapted to (i) provide, to the computing device, images from the at least one camera, and (ii) receive, from the computing device, control signals for controlling the plurality of light sources.

14 Claims, 59 Drawing Sheets

(51) Int. Cl.
*A61B 3/11* (2006.01)
*A61B 3/024* (2006.01)

(52) U.S. Cl.
CPC .......... *A61B 3/0033* (2013.01); *A61B 3/0041* (2013.01); *A61B 3/0075* (2013.01); *A61B 3/024* (2013.01); *A61B 3/14* (2013.01); *A61B 2560/0431* (2013.01)

(58) Field of Classification Search
CPC ......... A61B 3/145; A61B 5/16; A61B 5/4088; A61B 2560/0431; A61B 3/0033; A61B 3/0041; A61B 3/0075; A61B 3/024; A61B 2560/0475; A61B 3/113; A61B 5/08; A61B 5/1079; A61B 5/48
USPC ........ 351/200, 205, 206, 209–211, 221, 222, 351/243–246
See application file for complete search history.

(56) References Cited

U.S. PATENT DOCUMENTS

| | | | |
|---|---|---|---|
| 5,422,690 A | 6/1995 | Rothberg et al. | |
| 5,459,536 A | 10/1995 | Shalon et al. | |
| 5,610,673 A | 3/1997 | Rafal et al. | |
| 5,646,709 A | 7/1997 | Carter | |
| 5,805,271 A | 9/1998 | Kirschbaum et al. | |
| 5,892,568 A | 4/1999 | Carter | |
| 6,022,109 A | 2/2000 | Dal Santo | |
| 6,116,736 A * | 9/2000 | Stark .................. | A61B 3/112 351/206 |
| 6,260,968 B1 | 7/2001 | Stark et al. | |
| 6,820,979 B1 | 11/2004 | Stark et al. | |
| 7,083,280 B2 | 8/2006 | Hakamata | |
| 7,118,217 B2 | 10/2006 | Kardon et al. | |
| 7,147,327 B2 | 12/2006 | Stark et al. | |
| 7,216,982 B2 | 5/2007 | Fujimatsu et al. | |
| 7,258,444 B2 | 8/2007 | Gorin | |
| 7,407,287 B2 | 8/2008 | Hakamata | |
| 7,448,751 B2 | 11/2008 | Kiderman et al. | |
| 7,520,614 B2 | 4/2009 | Joos et al. | |
| 7,524,064 B2 | 4/2009 | Wyatt | |
| 7,614,746 B2 | 11/2009 | Severns | |
| 7,618,143 B2 | 11/2009 | Clark et al. | |
| 7,625,087 B2 | 12/2009 | Taylor et al. | |
| 7,665,845 B2 | 2/2010 | Kiderman et al. | |
| 7,670,002 B2 | 3/2010 | Stark et al. | |
| 7,677,728 B2 | 3/2010 | Hirohara et al. | |
| 7,712,899 B2 | 5/2010 | Tanassi et al. | |
| 7,731,360 B2 | 6/2010 | MacDougall et al. | |
| 7,753,523 B2 | 7/2010 | Kiderman et al. | |
| 7,866,818 B2 | 1/2011 | Schroeder et al. | |
| 7,967,442 B2 | 6/2011 | Siminou | |
| 7,976,160 B2 | 7/2011 | Nauche | |
| 7,980,699 B2 | 7/2011 | Neal et al. | |
| 8,016,420 B2 | 9/2011 | Yee et al. | |
| 8,096,658 B2 | 1/2012 | Kikawa et al. | |
| 8,235,526 B2 | 8/2012 | Stark et al. | |
| 8,348,426 B2 | 1/2013 | Tsukada et al. | |
| 8,388,135 B2 | 3/2013 | Hacker et al. | |
| 8,393,734 B2 | 3/2013 | Privitera et al. | |
| 8,500,281 B2 | 8/2013 | Ahn et al. | |
| 8,534,840 B2 | 9/2013 | Siminou | |
| 8,662,667 B2 | 3/2014 | Schuhrke et al. | |
| 8,744,140 B2 | 6/2014 | Baughman et al. | |
| 8,750,575 B2 | 6/2014 | Baughman et al. | |
| 8,807,753 B2 | 8/2014 | Maddess et al. | |
| 8,833,940 B2 | 9/2014 | Yee et al. | |
| 8,911,085 B2 | 12/2014 | Privitera et al. | |
| 9,101,296 B2 | 8/2015 | Schroeder et al. | |
| 9,198,570 B2 | 12/2015 | Siminou, III et al. | |
| 9,220,408 B2 | 12/2015 | Privitera et al. | |
| 2002/0099305 A1 | 7/2002 | Fukushima et al. | |
| 2003/0098951 A1 | 5/2003 | Hakamata | |
| 2004/0246441 A1 | 12/2004 | Stark et al. | |
| 2005/0099601 A1 | 5/2005 | MacDougall et al. | |
| 2005/0270483 A1 | 12/2005 | Fujimatsu et al. | |
| 2006/0106437 A1 | 5/2006 | Czeisler et al. | |
| 2006/0181678 A1 | 8/2006 | Stark et al. | |
| 2006/0181679 A1 | 8/2006 | Hakamata | |
| 2006/0189886 A1 | 8/2006 | Jones et al. | |
| 2006/0200751 A1 | 9/2006 | Underwood et al. | |
| 2007/0121068 A1 | 5/2007 | MacDougall et al. | |
| 2007/0132841 A1 | 6/2007 | MacDougall et al. | |
| 2007/0229760 A1 | 10/2007 | Hirohara | |
| 2008/0024724 A1 | 1/2008 | Todd | |
| 2008/0049186 A1 | 2/2008 | MacDougall et al. | |
| 2008/0049187 A1 | 2/2008 | Joos et al. | |
| 2008/0117384 A1 | 5/2008 | Inakagata et al. | |
| 2008/0198330 A1 | 8/2008 | Taylor | |
| 2008/0234972 A1 | 9/2008 | Tsukada et al. | |
| 2008/0273084 A1 | 11/2008 | MacDougall et al. | |
| 2008/0278685 A1 | 11/2008 | MacDougall et al. | |
| 2008/0284979 A1 | 11/2008 | Yee et al. | |
| 2009/0161090 A1 | 6/2009 | Campbell et al. | |
| 2009/0174865 A1 | 7/2009 | Privitera et al. | |
| 2009/0190093 A1 | 7/2009 | Tanassi et al. | |
| 2010/0149489 A1 | 6/2010 | Kikawa et al. | |
| 2010/0165293 A1 | 7/2010 | Tanassi et al. | |
| 2010/0195049 A1 | 8/2010 | Stark et al. | |
| 2010/0214532 A1 | 8/2010 | Siminou | |
| 2010/0220286 A1 | 9/2010 | Nauche | |
| 2010/0249532 A1 | 9/2010 | Maddess et al. | |
| 2011/0033090 A1 | 2/2011 | Baughman et al. | |
| 2011/0043758 A1 | 2/2011 | Ahn et al. | |
| 2011/0069279 A1 | 3/2011 | Hacker et al. | |
| 2011/0228224 A1 | 9/2011 | Siminou | |
| 2011/0279777 A1 | 11/2011 | Yee et al. | |
| 2012/0268715 A1 | 10/2012 | Stark et al. | |
| 2012/0274906 A1 | 11/2012 | Privitera et al. | |
| 2013/0011023 A1 | 1/2013 | Baughman et al. | |
| 2013/0033677 A1 | 2/2013 | MacDougall et al. | |
| 2014/0043587 A1 | 2/2014 | Siminou, III et al. | |
| 2014/0347629 A1 | 11/2014 | Donitzky et al. | |
| 2015/0282704 A1 | 10/2015 | Maddess et al. | |
| 2015/0297074 A1 | 10/2015 | Privitera et al. | |
| 2015/0342495 A1 | 12/2015 | Davis et al. | |

OTHER PUBLICATIONS

Chibel et al., "Chromatic Multifocal Pupillometer for Objective Perimetry and Diagnosis of Patients with Retinitis Pigmentosa", Ophtalmology, 123, pp. 1898-1911, 2016.

Rotenstreich et al., "Novel technique: a pupillometer-based objective chromatic perimetry", SPIE BiOS, vol. 8930, pp. 89300G-1-89300G-9, International Society for Optics and Photonics, 2014.

Rotenstreich et al., "The first prototype of chromatic pupillometer for objective perimetry in retinal degeneration patients", Ophthalmic Technologies, SPIE, vol. 9307, pp. 93070Q-1-93070Q-7, 2015.

Skaat et al., "Pupillometer-Based Objective Chromatic Perimetry in Normal Subjects and Glaucoma Patients", Investigative Ophthalmology & Visual Science, vol. 52, 5094, Apr. 2011 (Abstract only).

Rotenstreich et al., "Novel Technique" A Pupillometer-Based Objective Chromatic Perimetry, Investigative Ophthalmology & Visual Science, vol. 54, 3944, Jun. 2013 (Abstract only).

Rotenstreich et al., "Novel technique: a pupillometer-based objective chromatic perimetry", SPIE Photonics West 2014, Presentation: Feb. 1-6, 2014, Abstract only published.

Chibel et al., "Chromatic pupillometer-based perimetry in normal eyes and patients with retinitis pigmentosa", Israel Society for Vision & Eye Research 34rd Annual Meeting, p. 100, Presentation: Mar. 26-27, 2014, Abstract only published.

Mhajna et al., "Chromatic pupillometer-based perimetry in patients with Best's vitelliform macular dystrophy", Israel Society for Vision & Eye Research 34rd Annual Meeting, p. 101, Presentation: Mar. 26-27, 2014, Abstract only published.

Yahia et al, "Objective chromatic pupillometer—pupillary responses of health subjects to chromatic stimulations from small 2.5-mm-diameter spots", Israel Society for Vision & Eye Research 34rd Annual Meeting, p. 122, Presentation: Mar. 26-27, 2014, Abstract only published.

(56) References Cited

OTHER PUBLICATIONS

Sher-Rosenthal et al., "Novel Technique: Chromatic Multifocal Pupillometer for Objective Evaluating 76-Point Central 30 Degree Perimetry", Investigative Ophthalmology & Visual Science, vol. 55, 4839, Apr. 2014 (Abstract Only).
Ben-Ner et al., "Chromatic multifocal pupillometer for objective perimetry in patients with macular degeneration", Israel Society for Vision & Eye Research 35th Annual Meeting, p. 88, Presentation: Mar. 11-12, 2015, Abstract only published.
Chibel et al., "Chromatic multifocal pupillometer for objective perimetry in health subjects and patients with retinal dystrophies", Israel Society for Vision & Eye Research 35th Annual Meeting, p. 89, Presentation: Mar. 11-12, 2015, Abstract only published.
Yahia et al., "Pupillary responses of healthy subjects to chromatic light stimuli at incremental intensities at central and peripheral visual field locations", Israel Society for Vision & Eye Research 35th Annual Meeting, p. 87, Presentation: Mar. 11-12, 2015, Abstract only published.
Rotenstreich et al., "Chromatic multifocal pupillometer for objective perimetryin patients with macular degeneration", SPIE Photonics West 2016, Presentation: Feb. 13-18, 2016, Abstract only published, p. 110.
Rotenstreich et al., "Pupillary responses of healthy subjects to chromatic light stimuli at incremental intensities at central and peripheral visual field locations", SPIE Photonics West 2016, Presentation: Feb. 13-18, 2016, Abstract only, p. 110 published.
Rotenstreich et al., "Objective chromatic perimetry using a multifocal pupillometer", SPIE Photonics West 2016, Presentation: Feb. 13-18, 2016, Abstract only published, p. 117.
Rotenstreich et al., "Chromatic Multifocal Pupillometer for Objective Early Diagnosis of Mild Cognitive Impairment", Proc. of SPIE Vo. 10045, p. 100451Z-1, Abstract Only.
Ben-Ner et al., "Chromatic Multifocal pupillometer for Objective Diagnosis of Neurodegeneration in the Eye and the Brain", Israel Society for Vision & Eye Research 37th Annual Meeting, p. 30, Presentation: Mar. 15-16, 2017, Abstract only published.
Rotenstreich et al., "Chromatic multifocal pupillometer for objective perimetry in macular and retinal degeneration Diseases", American Academy of Ophthalmology, AAO 2016 Presentation: Oct. 15-18, 2016, Abstract only published.
Sher-Rosenthal et al., "Chromatic multifocal pupilloperimetry for objective perimetry in retinal and optic nerve neurodegeneration", AROV Annual Meeting Presentation, Jun. 2017, Abstract only published.
Skaat et al., "A Preliminary Evaluation of a Pupillometer-Based Objective Chromatic Primetry", Investigative Ophthalmology & Visual Science, vol. 51, 4793, Apr. 2010, Abstract only published.
Curcio et al., "Human Photoreceptor Topography", The Journal of Comparative Neurology, 1990, 292: 497-523, Wiley-Liss, Inc.
Kardon et al., "Chromatic Pupillometry in Patients with Retinitis Pigmentosa", American Academy of Opthalmology, 2011, 376-381, Elsevier Inc.
Kardon et al., "Chromatic Pupil Responses. Preferential Activation of the MelanpsinMediated Versus Outer Photoreceptor-Mediated Pupil Light Reflex", American Academy of Ophthalmology, 2009, 1564-1573.
Rotenstreich et al., "The Application of Chromatic Dark-Adapted Kinetic Perimetry to Retinal Diseases", American Academy of Ophthalmology, 2004, 1222-1227, Elsevier Inc.
Tapia et al., "Pupillary responses evoked by chromatic stimulus in objective perimetry", IS&T/SPIE Conference on Human Vision and Electronic Imaging IV, Jan. 1999, 598-605, SPIE vol. 3644.
Gomez et al., "Pupillary Escape Quantification with an Image-Processing System in Clinical Perimtry", Bioelectronics Section, Department of Electrical Engineering; Proceeding of SPIE 1996, vol. 2673, 252-261.
Rotenstreich et al., "The Application of Chromatic Dark-Adapted Kinetic Perimetry to Retinal Diseases", Department of Opthalmology and Visual Sciences, Ophthamology, Jun. 2004,vol. 111, No. 6, 1222-1227.
Maeda et al., "A Pupil Perimeter for Objective Visual Field Measurement", Department of Sensory Science, Complex Medical Engineering, May 2007, IEEE/ICME International Conference, 1116-1119.
International Search Report and Written Opinion dated Mar. 23, 2011 pertaining to International Application No. PCT/IL2010/000624.
International Search Report and Written Opinion dated Mar. 24, 2015 pertaining to International Application No. PCT/IB2014/002922.
European Search Report dated Feb. 26, 2015 for EP Application No. 10754996.6.

* cited by examiner

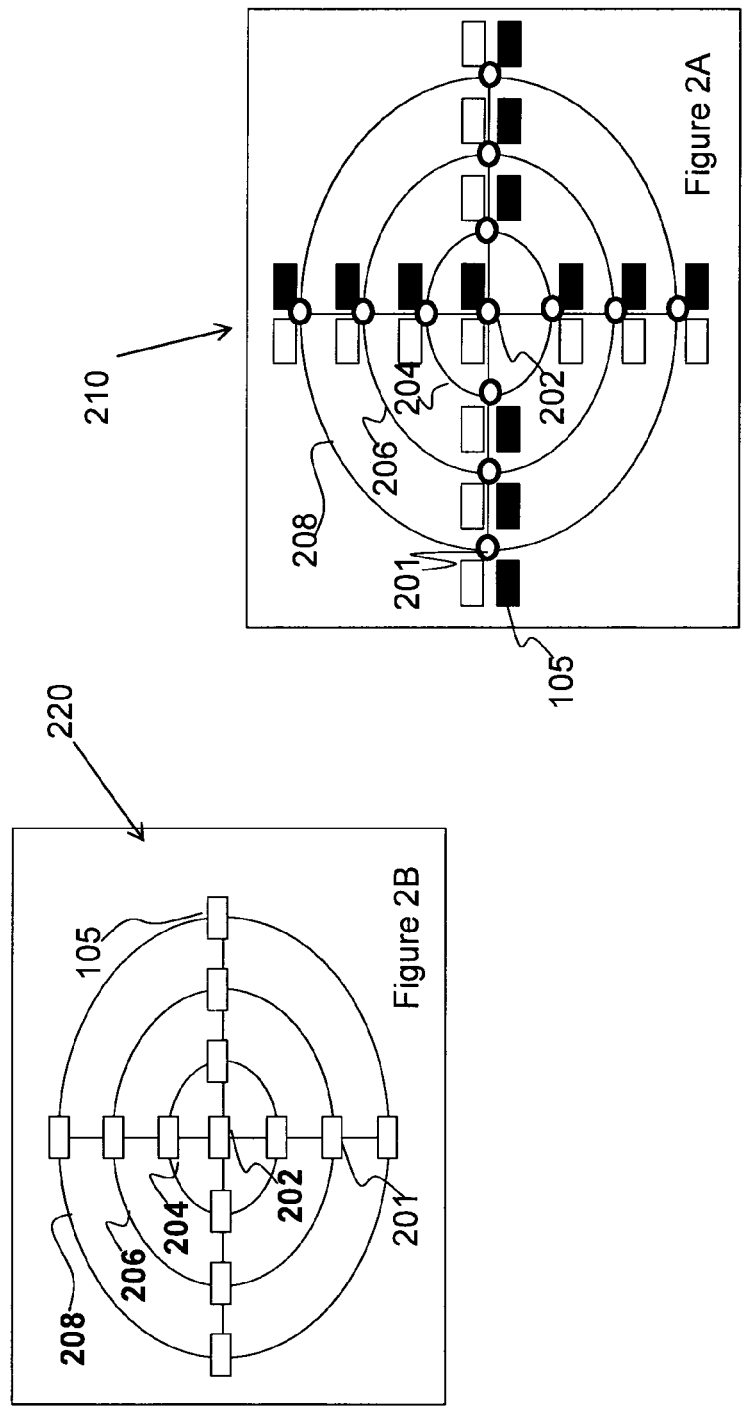

FIG. 15

| Visual Field Location | P value (RED) | P value (BLUE) |
|---|---|---|
| center | 0.17 | 0.01 |
| N10 | 0.12 | 0.02 |
| N20 | 0.07 | 0.007 |
| N30 | 0.18 | 0.18 |
| T10 | 0.61 | 0.13 |
| T20 | 0.01 | 0.01 |
| T30 | 0.02 | 0.07 |
| I10 | 0.001 | 0.001 |
| I20 | 0.15 | 0.002 |
| I30 | 0.42 | 0.02 |
| S10 | 0.92 | 0.005 |
| S20 | 0.12 | 0.001 |
| S30 | 0.96 | 0.09 |

FIG. 19

| Location | Pearson Chi Square Test ($p$ Value) | | |
|---|---|---|---|
| | Low Intensity Blue | High Intensity Blue | Red |
| Ctr | 0.02 | 0.000 | 0.000 |
| Nasal 10° | 0.01 | 0.002 | 0.001 |
| Nasal 20° | 0.01 | 0.006 | 0.001 |
| Nasal 30° | 0.008 | 0.036 | 0.033 |
| Inferior 10° | 0.791 | 0.121 | 0.333 |
| Inferior 20° | 0.172 | 0.708 | 0.871 |
| Temporal 10° | 0.03 | 0.000 | 0.333 |
| Temporal 20° | 0.008 | 0.221 | 0.015 |
| Superior 10° | 0.007 | 0.000 | 0.001 |
| Superior 20° | 0.802 | 0.000 | 0.013 |

FIG. 22

PUPILLOMETERS AND SYSTEMS AND METHODS FOR USING A PUPILLOMETER

FIELD OF THE INVENTION

The present invention relates to systems, devices and methods for visual field testing and, in particular, to systems and methods for assessing various health conditions using a pupillometer.

BACKGROUND OF THE INVENTION

A visual field test, also known as perimetry, is a method of measuring an individual's entire scope of vision, that is, the central and peripheral vision. Such visual field tests attempt to map the visual field of each eye individually. Visual field testing is most frequently used to detect any signs of glaucoma-caused damage to the optic nerve. In addition it is useful for detection of central or peripheral retinal disease, eyelid conditions such as ptosis or drooping, optic nerve disease, and diseases affecting the visual pathways within the brain and associated with the Central Nervous System ("CNS").

The present prevailing method for visual field testing is performed as follows: one eye of the patient is covered, and the chin is placed on a concave chin rest. The patient must look straight ahead at all times in order to avoid testing the central vision rather than the periphery. Next, light flashes of various intensities are projected on the tested eye or onto a testing bowl at different locations. Whenever the patient notices a flash, he or she is instructed to push a button. After all the relevant viewing angles are covered, a computer program analyzes the patient's responses and assesses the visual field map of the tested eye.

The principal stumbling block of the above procedure is its subjectivity, requiring the patient to understand the testing instructions, fully cooperate, and complete the entire test in order to provide useful information. However, the patient cooperation may strongly depend on his or her level of fatigue, wakefulness and attentiveness. This problem is especially severe in case of ill or elderly patients, younger children or patients with mental disabilities and developmental delay. Consequently, the test results obtained by the current method may not be accurate and may lead to false medical diagnosis. Moreover, the results may not be repeatable, which does not allow for reliable and effective tracking of the patient's medical condition.

Additional tests to assess the state of the eye include the Pupillary Light Reflex ("PLR") to provide clinical signs of the condition associated with the CNS. The PLR tests the pupil response, namely constriction, by testing the pupil's response to light stimuli in each eye, where a healthy eye may be indicative of symmetric constriction of both pupils. A quantitative measurement of a PLR may be obtained using a pupillometer.

Pupil perimetry utilizes a pupillometer together with a stimulus arrangement similar to that of a perimeter to measure the latency and amplitude of the constriction of the pupil in response to stimuli, usually in the form of a spot ("small-area") of flashes of light that are directed to different locations on the retina.

The pupillary response to spatially-localized luminance increments has been used as an indicator of glaucomatous retinal damage, but the small-area stimuli used in pupil perimetry may target small retinal areas that only weakly stimulate a PLR, and may fail to stimulate a PLR if the small retinal area that is being stimulated by light has been damaged by glaucoma.

Standard pupil perimetry testing produces large variations in pupil response amplitude among patients, and the changes in sensitivity of the pupil response with the retinal location of the small-area light stimulus have also limited the usefulness of such measurements.

Pupillometer-based objective visual tests have been recited in some references, based on an achromatic beam stimulus which is applied at various angles, for example, U.S. Pat. No. 5,610,673 to Rafal et al, U.S. Pat. No. 7,524,064 to Wyatt, U.S. Pat. No. 7,258,444 to Gorin. However, these methods fail to achieve either accurate or repeatable visual field mapping due to their susceptibility to time variations in the human ocular system and to differences in the behavior of the ocular system of different patients.

SUMMARY OF THE INVENTION

There is an unmet need for a system and a method for objective chromatic perimetry analysis using a pupillometer that is adept at providing an indication of the state of health of the eye and in particular identifying damage to the eye. The present invention overcomes the deficiencies of the background by providing a system and method that provides an objective test and analysis that is able to quantify an individual's state of health of the eye. The system and method overcome the deficiencies of the art by providing individual specific indication of problem areas of the eye in obtaining measurements that are relative to an individual's field of vision at specific visual field testing points, rather than the full field test provided by the prior art. Moreover the objective test of optional embodiments of the present invention provides for a quick test that does not require patient specific interaction or input that is subjective and often unreliable or misleading. Rather, the test of the present invention most preferably measures a subject's PLR without a subject's input ensuring the objective nature of the test, hence more reliable and repetitive.

In one embodiment, the invention provides a portable pupillometer including a testing compartment, at least one ocular disposed on the testing compartment, two or more light sources disposed in the testing compartment and forming a plurality of visual stimuli for a subject looking through the at least one ocular, at least one camera configured to capture images of a pupil of the subject via infrared detection, the images indicating pupillary responses to the two or more light sources, and an interface for connection with a computing device external to the pupillometer, the interface adapted to (i) provide, to the computing device, images from the at least one camera, and (ii) receive, from the computing device, control signals for controlling the plurality of light sources.

In another embodiment, the invention provides a method for using a portable pupillometer including a testing compartment, at least one ocular disposed on the testing compartment, two or more light sources disposed in the testing compartment and forming a plurality of visual stimuli for a subject looking through the at least one ocular, at least one camera configured to capture images of a pupil of the subject via infrared detection, the images indicating pupillary responses to the two or more light sources, and an interface for connection with a computing device external to the pupillometer, the interface adapted to (i) provide, to the computing device, images from the at least one camera, and (ii) receive, from the computing device, control signals for controlling the plurality of light sources. The method includes: the light sources displaying to the subject visual stimuli based on the control signals received from the computing device; and the camera capturing images of the pupil of the subject via infrared detection and providing the images to the computing device.

An optional embodiment of the present invention provides a system and method for testing an individual's response to at least two or more stimuli that are individually associated with the anatomical tissue, cells, ganglion, or the like anatomical structures comprising the eye, for example, including but not limited to ganglion, most preferably the rods and cones, and elucidating a ratio reflective of the relative response of the stimuli utilized. For example the ratio utilized may comprise at least two response measurements associated with the group comprising of rods, cones, ganglion in any combination thereof, therein providing for a ratio selected from the group consisting of rods to cones; rods to ganglion, cones to ganglion, or the like.

An optional embodiment of the present invention provides a system and method for testing an individual's response to at least three or more stimuli that are individually associated with the anatomical tissue, cells, ganglion, or the like anatomical structures comprising the eye, for example including but not limited to ganglion, rods and cones, and optionally elucidating at least one or more ratios reflective of the relative response of the stimuli utilized; more preferably elucidating at least two ratios reflective of the relative response of the stimuli utilized. For example, at least two ratios utilized may for example be any combination of the ratio selected from the group comprising rods to ganglion, cones to ganglion, rods to cone, ganglion to rods, ganglion to cones, or the like. Optionally the evaluation of the eye may be provided by a utilizing a ratio comprising a common denominator for example, a ratio of rods to ganglion may be compared and evaluated with respect to the ratio of cones to ganglion.

A preferred embodiment of the present invention introduces at least two or more stimuli comprising at least one cone specific stimulus and at least one rod specific stimulus, to a plurality of location herein referred to as the visual field points ("VFP") of at least one eye, and measuring the PLR response, namely pupil constriction, via a pupillometer; and comparing the PLR response, at given VFP, of the respective stimulus to obtain a ratio indicative an individual's state of health of the eye.

For example, stimulus that is geared toward the rod is provided in the form of chromatic light flashes comprising a short wavelength most preferably a narrow beam within the blue spectrum range, for example including but not limited to wavelengths of about 450 nm, 455 nm, 460 nm, 465 nm, 470 nm, 475 nm, 480 nm, 485 nm, 490 nm or the like, most preferably the stimuli utilized is about 485 nm. Optionally the cone specific stimulus is provided in the form of chromatic light flashes comprising a long wavelength, most preferably narrow beam within the red spectrum range, for example, including but not limited to wavelengths of about 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, any combination thereof, or the like.

Optionally and preferably the ratio obtained according to optional embodiments of the present invention is a ratio of cone specific stimulus response to a rod specific stimulus response.

Optionally the ratio utilized may be region specific about the different visual field points tested. For example, the central field points of the VFP may optionally utilize a ratio determined by rod specific stimulus response to cone specific stimulus response, while the peripheral field points may utilize a ratio of cone specific stimulus response to a rod specific stimulus response, as an indication of eyes state of health in the particular region and/or visual field point.

Optionally the ratio provided by the system and method of the present invention provides for individual specific measurements, reducing variability between the tested population, an indicator of an individual's internal state of balance associated with the sympathetic and parasympathetic state. Optionally utilization of the ratio accounts for and reduces variability due to light scattering and supranuclear inhibition. Optionally the ratio according to the present invention may account for the variability among the population pupil size, therein providing a standardized measurement relative to an individual rather than a population. Optionally and preferably the ratio is adept at assessing and providing an indication of the extent of an individual's visual field rim.

The present invention resolves the above background art limitations by providing, in at least some embodiments, a reliable and objective visual field testing, that is reliable and repeatable. An optional embodiment of the present invention provides a decision support system for diagnosing eye and/or retinal damage by assessing a subject's PLR in response to at least two or more chromatic stimuli to define a ratio indicative of the underlying state of health of the tested eye.

Optionally the at least two stimuli is composed of a first stimulus comprising a short wavelength chromatic stimulus and a second stimulus comprising a long wavelength chromatic stimulus, and wherein the ratio is the determined by evaluating the long wavelength PLR response with respect to the short wavelength PLR response of the tested eye.

Optionally the first stimulus is within the blue range from about 450 nm to about 490 nm, optionally and preferably about 475 nm, more preferably 480 nm and most preferably 485 nm. Optionally the second stimulus is within the red range from about 635 nm to about 700 nm, optionally and preferably about 650 nm.

An optional embodiment of the present invention provides a system for objective chromatic perimetry test comprising a pupillometer, a process and a camera that most preferably does not require subject input:

a. the pupillometer comprising:

i. a testing compartment provided in the form of a hemispheric bowl, wherein an inner surface of the bowl comprises a plurality of openings forming form a plurality of visual field testing points; and ii. wherein the hemispheric bowl may be associated with a plurality of chromatic beam emitters arranged about the visual field such that they are disposed over the plurality of visual field testing points; and wherein the chromatic emitters provide for generating a chromatic stimuli about the visual field points; and wherein iii. the stimuli comprises at least two different stimulus selected from the visual spectrum spanning from about 390 nm to about 750 nm wherein the different stimulus are individually characterized by their individual stimulus parameters including wavelength, duration, delay, and intensity; and iv. wherein the outer perimeter of the inner surface of the testing compartment further comprises a light adaptation emitter wherein the adaptation emitter comprising at least one or more chromatic beam emitters; and v. The inner surface further comprising a fixation point opposite a subject's line of sight; and vi. The bowl further comprising at least one or more opening for at least one or more camera provided for recording the pupil contraction in response to the stimuli; and b. The processor provided for controlling the chromatic beam emitters, the stimulus parameters and the visual field points; and wherein the processor processes data associated with and generated by the stimulus and camera.

Optionally and preferably the device according to the present invention may be adapted to provide for color vision testing.

Optionally the stimuli may include a first stimulus characterized in that it may be a short wavelength chromatic beam and a second stimulus characterized in that it may be a long wavelength chromatic beam.

Optionally the stimuli comprises up to three individual stimuli. Optionally the first stimulus may be provided in the form of a chromatic beam in the blue wavelength range centered at about 480 nm or about 485 nm. Optionally the chromatic beam stimulus may be selected from about 450 nm to about 495 nm and comprising a blue wavelength beam selected from about the group consisting of about 450 nm, 455 nm, 460 nm, 465 nm, 470 nm, 475 nm, 480 nm, 485 nm, 490 nm, 495 nm, 500 nm, or any combination thereof.

Optionally the second stimulus may be a chromatic beam in the red wavelength range centered about 640 nm or about 620 nm. Optionally the second stimulus chromatic beam may be selected from about 590 nm to about 750 nm and comprising a red wavelength selected from the group, for example, including but not limited to about 610 nm, 615 nm, 620 nm, 625 nm, 630 nm, 635 nm, 640 nm, 645 nm, 650 nm, 655 nm, 660 nm, or any combination thereof.

Optionally the first stimulus and the second stimulus are adapted to individually stimulate a specific anatomical structure of the eye. Optionally the first stimulus may be adapted to stimulate rods and ganglion while the second stimulus may be adapted to stimulate cones.

Optionally the stimulus may be characterized in that it may be specific an anatomy of the eye; and wherein the system of the present invention comprises at least two stimuli that may be generated to simulate at least two anatomical structures of the eye.

Optionally a light adaptation emitter comprises three chromatic beam emitters adapted to produce a visible color about the inner surface of the bowl of the test compartment.

Optionally the hemispheric bowl may be provided in the form of a Ganzfeld dome or a Goldmann or static perimeter.

Optionally the plurality of chromatic beam emitters or the plurality of openings are further provided with a controllable shutter for controlling the size and shape of the generated stimulus. Optionally and preferably the shutter size may be adapted to provide a stimulus having a substantially circular formation with a diameter from about 0.8 cm to about 2 cm. Optionally and preferably shutters may be controllable with the processors.

Optionally the plurality of chromatic beam emitters are provided in the form of a Light Emitting Diode ("LED"). Optionally the LED provides a specific chromatic beam characterized in that it may be specific to an anatomy of the eye. Optionally the LED may provide a plurality of optional specific chromatic beams characterized in that each beam may be individually specific to an anatomy of the eye.

Optionally the chromatic beam emitters or the openings about the inner surface of the test compartment are arranged to provide from about 13 to about 256 visual field testing points about the vertical and horizontal planes of the hemispheric bowl. Optionally each of the visual field point comprises at least one chromatic beam emitter in the form of a LED that may provide a plurality of optional specific chromatic beams.

Optionally the device according to the present invention may be configured such that each of the visual field points may comprise at least two chromatic beam emitters in the form of a LED characterized in that each LED provides a specific chromatic beam.

Optionally the device according to the present invention may be configured such that each of the visual field point comprises at least three chromatic beam emitters that may optionally be provided in the form of a LED.

Optionally the chromatic beams may be further characterized in that each beam may be individually specific to an anatomic structure of the eye, for example including but not limited to the rods and cones, ganglion.

Optionally the fixation point may be disposed at about the pole of the hemispheric bowl and may comprise up to four fixation points about the center.

Optionally the system according to the present invention may comprise at least one and up to four cameras, for objectively recording the PLR of a subject. Optionally the system may comprise at least one, or at least two, or at least three or at least four cameras. Optionally the PLR may be recorded for each eye utilizing at least two cameras.

Optionally the shutter may for example be provided in the form of a static shutter or a dynamic shutter, or a combination thereof or the like.

Optionally the stimulus duration or delay may be controllably set to be any single value or range of values selected from about 100 ms to about 4000 ms.

Optionally the stimulus intensity used with a system and method according to the present invention may be controllably set to be any single value or range of values from about from $3.98 \times 10^{-8}$ cd/m$^2$ up to about $3.98 \times 10^2$ cd/m$^2$. An optional embodiment of the present invention provides for a method for determining the state of health of an eye with a pupillometer providing an objective chromatic perimetry analysis test, where most preferably a subject's input is not required and therefore the test is performed and results are analyzed independently of subject's input. Most preferably the measurement of the PLR in response to chromatic beam stimuli is presented at a plurality of visual field testing points, and defining a ratio of the measured PLR at each of the plurality of visual field testing points in response to a first chromatic beam stimulus relative to a response to a second chromatic beam stimulus, wherein the first and second stimulus are characterized by parameters, for example, including but not limited to wavelength, duration, delay, and intensity; and wherein the stimuli wavelength are selected from the visual spectrum spanning from about 390 nm to about 750 nm.

Optionally the first chromatic beam stimulus may be a short wavelength beam and the second chromatic beam stimulus may be a long wavelength beam. Optionally the first chromatic beam may be within the blue wavelength spectrum range centered at about 480 nm or about 485 nm; and the second chromatic beam may be a chromatic beam within the red wavelength spectrum range centered at about 640 nm or about 620 nm.

Optionally the ratio of the PLR is measured with the long wavelength response relative to the PLR measured with the short wavelength response. Optionally the first and second chromatic beam stimuli are specific to different anatomical structures within the eye, for example, including but not limited to rods, cones and ganglion. Optionally the first stimuli may be directed at the rods; and the second stimuli may be directed at the cones.

Optionally the first stimulus may be provided for a duration of about 1 s (one second), with an intensity of about $3.98 \times 10^{-8}$ cd/m$^2$, with an inter-stimulus pause of about 891 ms (milliseconds); and the second stimulus may be provided for a duration of about 1 s (one second), with an intensity of about $3.98 \times 10^{-8}$ cd/m$^2$, with an inter-stimulus pause of about 1023 ms (milliseconds).

Optionally the first and second stimulus may be presented to a subject at least once and up to three times for each visual field testing point.

Most preferably the ratio may be mapped to a visual field map. Optionally and preferably the ratio or map thereof may be indicative of the state of health of anatomical structures correlated with individual visual field points.

Optionally the ratio that may be indicative of underlying normal and/or healthy anatomical structures are provided by the following field point coordinates and expected ratio (0°, nasal, 0.50); (10°, nasal, 0.41); (10°, temporal, 0.45); (10°, up, 0.48); (10°, down, 0.43); (20°, nasal, 0.40); (20°, temporal, 0.33); (20°, up, 0.38); (20°, down, 0.39); (30°, nasal, 0.50); (30°, temporal, 0.44); (30°, up, 0.5); (30°, down, 0.40). Optionally the ratios may be indicative of the state of health of an eye associated with glaucoma, and retinitis pigmentosa (RP). Optionally the ratios may be indicative of the state of health of an eye associated with color blindness.

Optionally and preferably the test according to the present invention may be performed with background luminance providing for light adaptation. Optionally and preferably background luminance and light adaptation may be controllable, preferably provided to facilitate testing of an anatomical structure of the eye. Optionally the background luminance may be any one value or a range of values selected from about 1 cd/m$^2$ to about 20 cd/m$^2$. Optionally background luminance may be about 2.7 cd/m$^2$ or about 17.1 cd/m$^2$ (about 5 foot-lambert). Optionally the onset of light adaptation may be controlled and therefore provided at a plurality of optional portions of the test or at different controllable periods of the test, for example, including but not limited to between stimulus presentations, between visual field testing points, between visual field rings, or any combination thereof or the like. An optional embodiment of the present invention provides device in the form of a pupillometer for performing an objective chromatic perimetry test, that most preferably does not require a subject's input, the device comprising a pupillometer testing compartment and at least one or more cameras, the pupillometer testing compartment comprising:

a. the testing compartment provided in the form of a hemispheric bowl, wherein an inner surface of the bowl comprises a plurality of openings forming form a plurality of visual field testing points; and b. wherein the hemispheric bowl may be associated with a plurality of chromatic beam emitters arranged about the visual field such that they are disposed over the plurality of visual field testing points; and wherein the chromatic emitters provide for generating a chromatic stimuli about the visual field points; and wherein c. the stimuli comprises at least two different stimulus selected from the visual spectrum spanning from about 390 nm to about 750 nm wherein the different stimulus are individually characterized by their individual stimulus parameters including wavelength, duration, and intensity; and d. wherein the outer perimeter of the inner surface of the testing compartment further comprises a light adaptation emitter wherein the adaptation emitter comprising at least one or more chromatic beam emitters; and e. The inner surface further comprising a fixation point opposite a subject's line of sight; and f. The bowl further comprising at least one or more opening for at least one or more camera provided for recording the pupil contraction in response to the stimuli.

An optional embodiment of the present invention provides for determining the a ratio of the PLR response at individual visual field testing points based on a response to at least two or more, or three or more, or four or more chromatic beam stimuli presented to a tested eye. Optionally a different ratio may be determined based on how the eye was stimulated, for example, each eye individually, both eyes in turn, or both eyes simultaneously.

Unless otherwise defined the various embodiment of the present invention may be provided to an end user in a plurality of formats, platforms, and may be outputted to at least one of a computer readable memory, a computer display device, a printout, a computer on a network or a user.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and/or the ability to execute one or more instructions may be described as a computer, including but not limited to a PC (personal computer), a server, a minicomputer, a cellular telephone, a smart phone, a PDA (personal data assistant), a pager. Any two or more of such devices in communication with each other, and/or any computer in communication with any other computer, may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2A-C are schematic illustrative diagrams of visual field points showing alternative configurations for the chromatic beam emitters according to optional embodiments of the present invention;

FIG. 4A presents measured results with the long wavelength stimuli within the red spectrum, about 610 nm, associated with the cones. FIG. 4B presents measured results with the short wavelength stimuli within the blue spectrum, about 485 nm, associated with the rods. FIG. 4C presents the long wavelength to short wavelength ratio according to the present invention as obtained from the results presented in FIG. 4A and FIG. 4B.

FIG. 5A presents measured results with the long wavelength stimuli within the red spectrum, about 610 nm, associated with the cones. FIG. 5B presents measured results with the short wavelength stimuli within the blue spectrum, about 485 nm, associated with the rods. FIG. 5C presents the long wavelength to short wavelength ratio according to the present invention as obtained from the results presented in FIG. 5A and FIG. 5B.

FIG. 6A presents measured results with the long wavelength stimuli within the red spectrum, about 610 nm, associated with the cones. FIG. 6B presents measured results with the short wavelength stimuli within the blue spectrum, about 485 nm, associated with the rods. FIG. 6C presents the long wavelength to short wavelength ratio according to the present invention as obtained from the results presented in FIG. 6 A and FIG. 6B. FIG. 6D provides an additional view of FIG. 56 on a background of the traditional visual field map for the tested glaucoma patient.

FIG. 7A shows an infrared video image of a pupil while being recorded with the pupil tracking system, and FIG. 7B shows an example of pupil recordings from the chromatic multifocal pupillometer.

FIG. 15 is a table showing demographic, genetics, visual acuity, and ERG findings for study patients.

FIG. 19 is a table showing agreement between the chromatic pupillometer recordings and chromatic Goldmann in RP patients.

FIG. 22 shows agreement between the chromatic pupillometer recordings and Humphrey's perimetry in glaucoma patients.

DETAILED DESCRIPTION

The principles and operation of the present invention may be better understood with reference to the drawings and the accompanying description. The following reference labels listed below are used throughout the drawings to refer to objects having similar function, meaning, role, or objective.

100 Pupillometer;
101 Pupillometer test compartment;
102 Pupillometer head and chin support frame;
103 Pupillometer ocular(s);
104 hemispheric surface; 105 chromatic beam emitters;
105a first stimuli chromatic beam emitters;
105b second stimuli chromatic beam emitters;
105c light adaptation RGB emitter;
106 camera;
107 focal fixation point marker;
108 shutters;
109 computer;
110 power supply;
112 light adaptation emitter;
120 objective chromatic perimetry system;
200 visual field map arrangement;
201 visual field points
202 0° field map ring;
204 10° field map ring;
206 20° field map ring;
208 30° field map ring;
210 multi source chromatic beam emitter configuration;
220 single source chromatic beam emitter configuration.

Figure 1A:
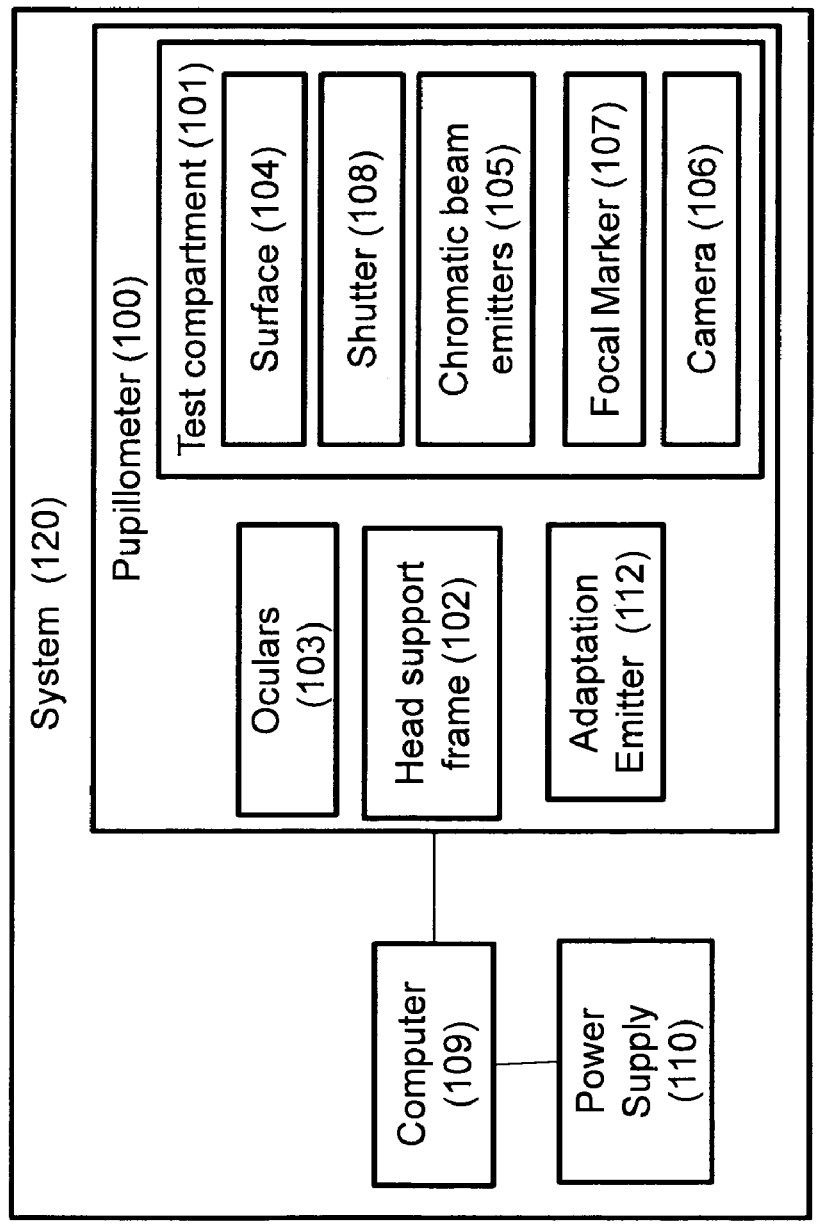
FIGS. 1A-B are schematic block diagrams of an exemplary system according to the present invention.
Figure 1B:
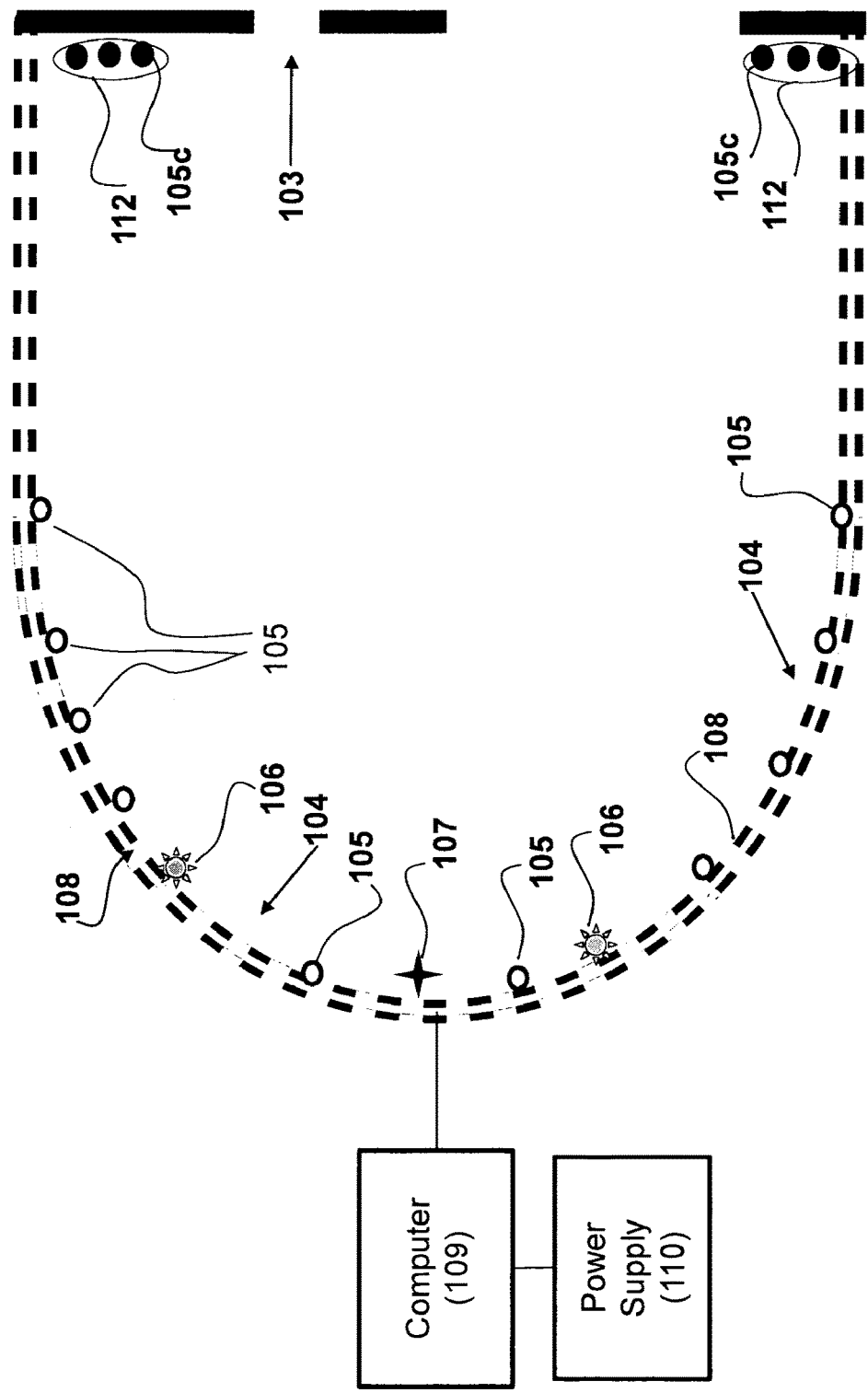

Referring now to the drawings, FIGS. 1A-B show schematic illustrative diagrams of system 120 of the present invention for objective chromatic perimetry analysis comprising a binocular pupillometer 100 and a computer 109. Pupillometer 100 is utilized to perform a Pupillary Light Reflex ("PLR") test of at least one eye where the PLR is measured by presenting the tested eye with stimulus and measuring the pupil's constriction response. Pupillometer 100 comprises a testing compartment 101 most preferably in the form of a Ganzfeld bowl and is a hemispherical shaped bowl to allow for testing of the full visual field of a subject. Preferably testing compartment 101 comprises an inner surface 104 forming a screen onto which the stimuli is presented, a plurality of chromatic beam emitters 105, focal fixation point marker 107 and camera 106.

Test compartment 101 preferably comprises and incorporates and is integrated with inner surface 104, where surface 104 is associated with at least one or more preferably a plurality of chromatic beam emitters 105 that preferably provide for generating and presenting the stimulus for a which a response is measured. Focal fixation point marker 107 provides a subject with a fixation point during the test, optionally and preferably fixation point comprises 4 beams of red light arranged about a central point on surface 104, most preferably the pole of surface 104. Camera 106, for example in the form of a CCD camera or a the like digital camera, may be provided within test compartment and is preferably directed toward the tested eye so as to allow for visualizing and recording the pupil during testing therein providing for recording the PLR of the tested eye. Camera 106 (or, alternatively, a photodiode with filters) may also be used to verify visually that a given test stimulus has been activated. Most preferably at least one camera 106, may be disposed within test compartment 101, optionally at least one and up to four cameras may be provided and arranged within test compartment 101 to better identify the PLR of the tested eye. Optionally two cameras may be utilized to record a single tested eye. Optionally two cameras may be utilized to record a subject PLR when both eyes are tested simultaneously. Optionally up to four cameras may be utilized to record a subject PLR when both eyes are tested simultaneously, wherein at least one camera and more preferably at least two cameras are provided to record the PLR of each tested eye. Most preferably camera 106 transmits and records the subject's eye during testing sending data to computer 109 or the like processor for analysis, for example including but not limited to a server, PDA, smart phone or the like device comprising a processor. Most preferably data obtained by at least one or more camera 106 is processed with computer 109 via dedicated software.

Optionally camera 106 may be attached, coupled or otherwise associated with surface 104. Most preferably camera 106 continuously captures images of at least one of the tested eye, or of both eyes, for example, when the consensual reflex is tested. Optionally camera 106 may be substantially simultaneously controlled with emitters 105 by computer 109. Most preferably camera 106 continuously transfers images of the pupil to computer 109 at a rate of about 50 shots-per-second, or 40 shots per second or the like. Optionally the pupillary images may be provided and/or transferred in various forms for example including but not limited to stills, common digital video format or the like as is known in the art. Optionally camera 106 may communicate and/or transfer data to computer 109 through a plurality of optional communication technology and/or protocols for example including but not limited to wired, wireless, cellular, optical or acoustic communication protocols for example including but not limited to infrared, Bluetooth, wifi or the like.

Optionally computer 109 may further provide for decision support tools associated with the state of health of the eye. Optionally a decision support tool may provide physician and/or clinicians with assistance in analyzing and determining the state of health of the tested eye based on the results obtained with the system and method of embodiments of the present invention.

Figure 2C:
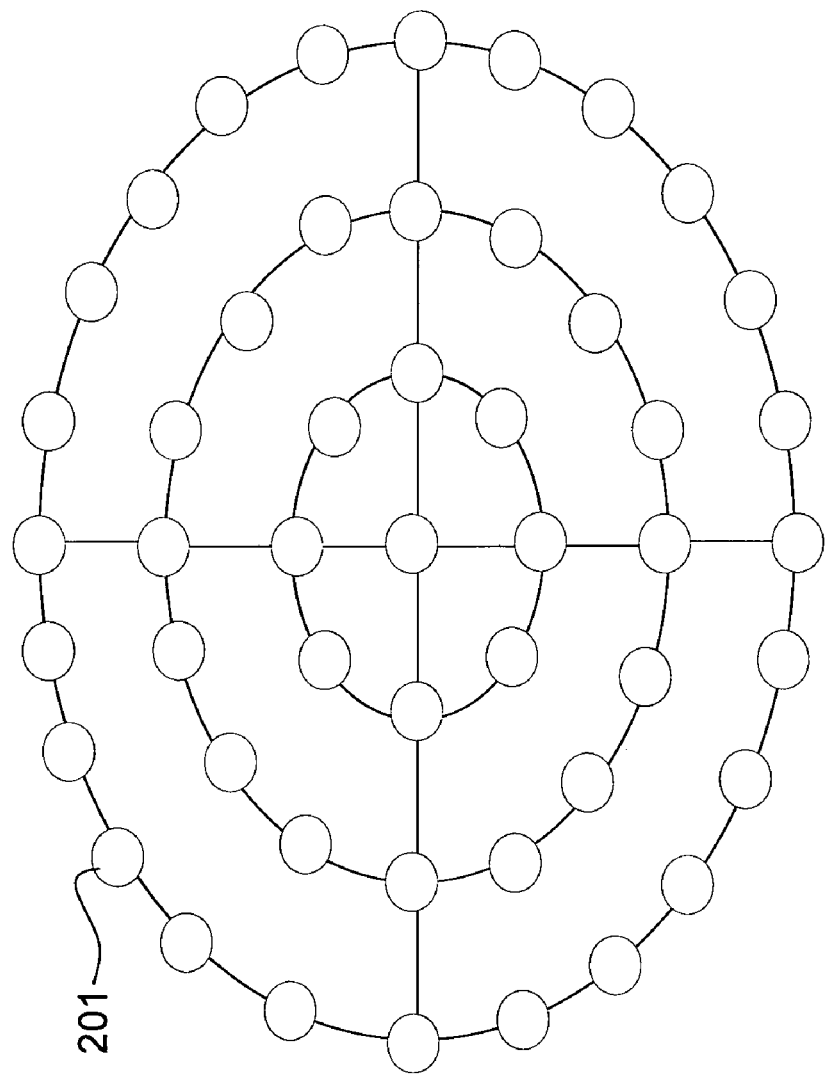

FIG. 1B provides a cross-section view of a schematic optional test compartment 101 of system 120. Test compartment 101 may be provided as an opaque chamber that preferably serves to block interference of external illumination during testing. Optionally and preferably the front side of test compartment 101 forms a support frame 102 that is capable of receiving the patient's head while supporting the chin and forehead. Preferably the middle section of support frame 102 comprises at least two openings 103 that serve as oculars allowing a subject to view the presented stimulus about surface 104. Optionally and preferably each ocular 103 may be controlled by computer 109. For example when testing only the subject's right eye the right ocular is controllably placed in the open position by computer 109 while the left ocular is placed in the closed position, allowing for isolating the right eye and measuring the PLR of the right eye only. The rear part of testing compartment 101, is optionally and preferably provided in the form of a semispherical bowl, Ganzfeld dome, Goldmann perimeter, or a like surface 104 that is preferably made of a reflective material. Most preferably at least one and more preferably a plurality of chromatic beam emitters 105, optionally in the form of a Light Emitting Diode ("LED") are located about, attached or otherwise coupled to surface 104. Optionally emitters 105 may be integrated with surface 104. Most preferably emitters 105 are provided in the form of a chromatic LED providing a narrow spectrum light source in the visible range. Optionally the arrangement of emitters 105 about surface 104 may be controlled, for example a single multi spectrum LED may be placed about the stimuli location field point as shown in FIG. 2B. Optionally at least two or more preferably a plurality of emitters 105, for example a spectrum specific LED, may be arranged about surface 104 as shown field map 210 in FIG. 2A, wherein each emitter 105 is specific to a particular chromatic stimulus source that is being tested. Most preferably emitters 105 provide for stimulating the tested eye in particular the retina by illuminating a portion of the eye with a chromatic narrow light beam. Optionally emitters 105 may be configured about surface 104 in a dense grid structure, optionally and preferably corresponding to visual field map having a plurality of point being tested, from about 13 to at least 256 or more as shown in FIG. 2C. Optionally a plurality of emitters 105 may be associated with or integrated with internal shutters to control stimulus parameters for example the shape, size, timing of the stimulus.

Optionally surface 104 may comprise a plurality of openings and shutters 108 arranged similarly to that of emitters 105 as shown in FIGS. 2A-C, optionally and preferably corresponding to the resolution of the visual field points tested. Optionally shutters 108 and/or openings may be controllable with computer 109 to control at least some parameters of the stimuli presented to the tested eye, for example including parameters such as the shape and size of the stimulus to be provided. Optionally screen 104 may be provided with a finite number, for example three, of controllable opening sizes and or shapes with which the presented stimulus may be controlled. Optionally shutter 108 may provide a stimulus size of about 0.05 cm to about 2 cm in diameter. For example, the stimulus shape may be chosen from circular with a diameter of about 1 cm, or a square with each side having a length of about 0.95 cm.

Most preferably surface 104 comprises a focal point marker 107 at about the central point of the surface 104. Optionally and preferably marker 107 is provided in the form of a dim red light that may serve as a focal marker for the tested patient. Optionally the focal fixation point marker may comprise at least one and up to four dim red light sources about a central point. During testing a subject is asked to look at focal marker 107 providing a common reference point that is repeatable point for all subjects and/or eyes tested. Optionally at a plurality of focal markers 107 may be utilized with Pupillometer 100.

Optionally light adaptation emitter 112 optionally and preferably comprising at least one and up to three chromatic beam emitters 105c, optionally in the red, green and blue range wavelength, may be disposed about the outer perimeter of test compartment 101 near head support frame 102, for example along the inner surface 104.

Optionally light adaptation emitter 112 may be attached to the front wall of test compartment 101. Preferably when light adaptation emitter 112 is activated it illuminates surface 104 providing for light adaptation as described in stage 302 of FIG. 3 where the light adaptation used may prime particular anatomical structures of the eye therein facilitating the performed test.

Optionally light adaptation emitter 112 may provide for fully illuminating screen 104 in any chromatic wavelength comprising a combination of at least one and up to three chromatic beam emitters 105c. Optionally stimulus control with light adaptation emitter 112 may be provided with controllable shutters 108 to selectively emit the light produced by emitter 112 to select field points 201 corresponding to selected shutters 108 that are in the open position, where most preferably control of the shutter 108 is provided with computer 109. Optionally light adaptation emitter 112 may provide for a color field perimetry test, for example, for testing color blindness about individual field points as shown in FIG. 2C.

Optionally and preferably computer 109 may provides for overall control of pupillometer 100 and system 120.

Power Supply unit 110 is most preferably coupled with main power which for providing system 120. Preferably power supply 110 converts and/or generates stabilized DC (Direct Current) voltages that are required for proper operation of system 120 and varying components of pupillometer 100.

FIGS. 2A-B provide illustrative diagrams of a 13 point visual field map 200 showing optional alternative configurations for the chromatic beam emitters 105, for each point 201, in the form of a multi source chromatic beam emitter configuration 210, FIG. 2A, in the form of a single source chromatic beam emitter configuration 220, FIG. 2B, each according to optional embodiments of the present invention.

FIG. 2A shows visual field 210 comprising a plurality of emitters 105 at each of a plurality of visual field points 201, optionally accounting for individual emitters 105, where each emitter 105 may provide for a specific chromatic beam stimulus at the a given visual field point about visual field 210, at each point 201. Optionally at least two or more chromatic beam emitters 105 may be provided at each visual field point 201. For example, emitters 105a and 105b may be provided to stimulate the tested eye at the same visual field point, for example at 30° field map ring 208. For example, beam emitter 105a may provide a short wavelength chromatic stimulus, for example, in the blue range at about 475 nm, while emitter 105b may provide a long wavelength chromatic stimulus, for example in the red range at about 650 nm. FIG. 2B shows visual field 220 comprising a single emitter 105 at individual visual field points 201, where optionally emitter 105 may provide at least two or more preferably a plurality of optional chromatic beams at varying wavelengths. For example, a single beam emitter 105 may provide both a short wavelength chromatic stimulus in the blue range, for example about 475 nm, and a long wavelength chromatic stimulus in the red range, for example about 650 nm, at a given visual field point 201 about visual field 220, for example at 20° field map ring 206, as shown.

FIG. 2C provides a depiction of an optional map of a visual field map with a plurality of points that may be used to stimulate a subject's eye during a test protocol according to the present invention. Optionally the number of field points 201, utilized with the system and method of the present application may vary from about 13 points to about 256 points or more, Optionally any number of points in a circular grid structure, about a visual field may be used to test specific areas of a subject's eye, for example a 64 point visual field map. Optionally the number of tested field points utilized is proportional to the desired resolution of the field map of the test protocol or the required test. Optionally each field ring 202, 204, 206, 208 is separated by about 10° to 30°, another option is that each point within the ring is spaced and/or separated by at about 5°, resulting in higher resolution with more points of examination in the visual field.

Figure 3:
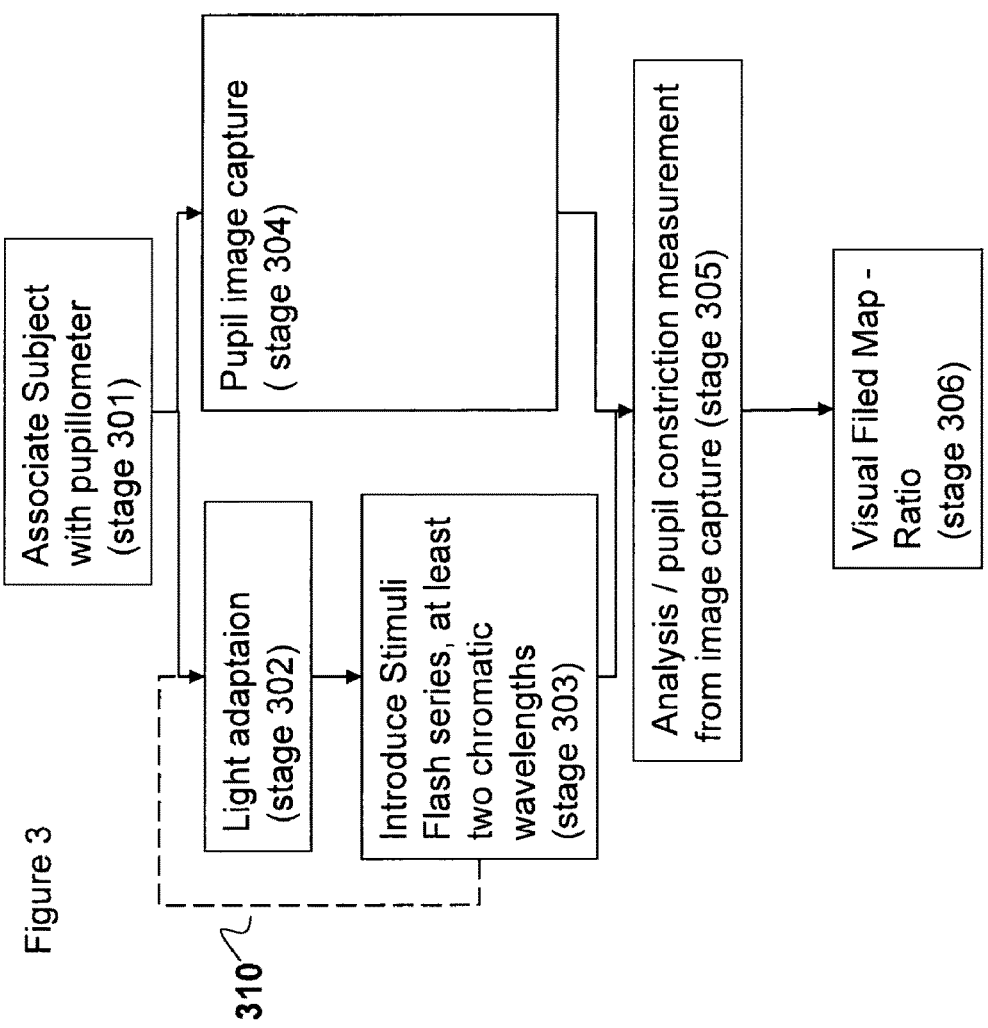
FIG. 3 is a flowchart of an exemplary method according to the present invention.

FIG. 3 shows a flowchart of an exemplary method according to the present invention for objective chromatic perimetry analysis using pupillometer therein providing an objective, repeatable and quick test.

In stage 301, a subject is prepared for the test where at least one eye of a subject is introduced to pupillometer 100 wherein the subject's forehead and chin are supported by support frame 102 while the tested eye is focused onto focal fixation point marker 107 through at least one ocular 103. Optionally and preferably test preparation may include selecting the test sequence to be preformed via computer 109 utilizing dedicated software. Most preferably testing sequence, comprising the stimulus parameters, the visual field points tested, tested eye(s), light adaptation and the number times a stimulus is presented or number of stimulus sessions, may be preset and automated according to the test being performed and/or according to the test's objectives. Optionally and preferably a testing sequence may be created manually, altered, changed, abstracted or otherwise controlled by an operator via dedicated software associated with computer 109 adapt at controlling pupillometer 100.

Most preferably stimulus parameters for example including but not limited to luminance, intensity, duration, and wavelength may be controlled by the operator via computer 109.

Optionally and preferably the visual field points stimulated (FIG. 2A-C) and the order and sequence by which they may be presented to a subject is automatically controlled or manually controlled via computer 109.

Optionally and preferably the number of stimuli provided at each of the visual field testing points may also be automated, manually or otherwise controlled via computer 109.

Optionally and preferably the test sequence and/or protocol may be performed on a single eye, on each eye individually one at a time, may alternate between both eyes, both eyes tested simultaneously, or any combination thereof. Optionally control of which eye is tested during the testing sequence is controlled via computer 109 and oculars 103. Optionally computer 109 provides for controlling oculars 103 according to the prescribed and/or selected testing sequence.

An objective chromatic perimetry test according to the present invention is initiated by simultaneously initiating and presenting a subject with stimulus as described in stage 303 below, while continuously capturing, recording and measuring a subject's PLR response to the presented stimuli in stages 304 and 305. Most preferably in stage 304 at least one or more cameras 106 disposed within testing compartment 101 are simultaneously activated with the image capture and PLR analysis provided with computer 109. In stage 302 following the pupillometer preparation and subject preparation, test compartment 101 is provided with a light adaptation where the background luminance, via light adaptation emitter 112 comprising at least one and up to three chromatic beam emitters 105c, of the test compartment is controlled and to facilitate and/or prime the eye for testing particular anatomical structures of the eye.

For example a background luminance of 2.7 cd/m$^2$ (candela per square meter) may be utilized to prime for testing of the rods, cones and ganglion. For example a background luminance equal to about 5 foot-lambert or 17.1 cd/m$^2$ (candela per square meter) may be utilized to specifically prime testing conditions for testing cones while suppressing rods. Most preferably light adaptation is provided throughout the test sequence and/or protocol.

Next in stage 303, the stimulus is provided to the tested eye, while camera 109 provides for capturing the images and video of subject's PLR. The stimulus and test sequence is preferably controlled with computer 109, and may be altered based on the type of test and test objective.

Optionally and preferably stimuli parameters are controllable, for example, including but not limited to wavelength, duration of stimulus, inter-stimuli delay, size, shape, luminance, intensity, or like parameters may be controlled with computer 109. Optionally test stimulus wavelength may be any chromatic beam from the visible spectrum spanning from about 390 nm to about 750 nm, for example including but not limited to violet range (about 380 nm to about 450 nm), blue range (about 450 nm to about 475 nm), cyan range (about 476 nm to about 495 nm), green range (about 495 nm to about 570 nm), yellow range (about 570 nm to about 590 nm), orange range (about 590 nm to about 620 nm), red range (about 620 nm to about 750 nm), in any combination thereof or the like. Optionally stimuli duration and/or delay may be from about 100 ms to about 4000 ms, for example including but not limited to about 100 m, about 200 ms, about 300 ms, about 400 ms, about 500 ms, about 600 ms, about 700 ms, about 800 ms, about 900 ms, about 1000 ms, about 1100 ms, about 1200 ms, about 1300 ms, about 1400 ms, about 1500 ms, about 1600 ms, about 1700 ms, about 1800 ms, about 1900 ms, about 2000 ms, about 2100 ms, about 2200 ms, about 2300 ms, about 2400 ms, about 2500 ms, about 2600 ms, about 2700 ms, about 2800 ms, about 2900 ms, about 3000 ms, about 3100 ms, about 3200 ms, about 3300 ms, about 3400 ms, about 3500 ms, about 3600 ms, about 3700 ms, about 3800 ms, about 3900 ms, about 4000 ms, or the like. Optionally stimuli luminance and/or intensity may be provided from about from $3.98 \times 10^{-8}$ cd/m² up to about $3.98 \times 10^{2}$ cd/m².

Optionally and preferably the test protocol and stimulus sequence may be presented to a subject in up to three sessions, optionally two sessions and most preferably at least one session, as shown with directional arrow 310.

Next following the completion of the test protocol where all stimuli have been presented over the specified visual field points to the tested eye and images of the PLR have been recorded (stage 304), in stage 305 and 306 a processor, optionally in the form of computer 109, may optionally provide a decision support device utilized to abstract the visual field map by determining a ratio of the PLR response of the second stimulus, long wavelength stimulus, in relation to the PLR response of the first stimuli, short wavelength stimulus. Most preferably PLR response is elucidated from video and image capture, provided by up to four cameras 106, utilized in stage 304 optionally with dedicated software adept at determining the pupil constriction and size. Most preferably the pupil constriction peak amplitude is then utilized to determine the PLR ratio per visual field points tested.

Most preferably the visual field map is determined in stage 306 is based on the recorded constriction results for each of the first and second stimuli to produce a PLR ratio of the long to short wavelengths ratio.

Optionally and preferably the resulting visual field map may be stored for later monitoring, decision support system diagnosis, and/or further processing.

Optionally any number of test protocol may be abstracted according to the method of the present invention where a ratio is used to evaluate individual visual field points for a number of animalize for example Glaucoma, RP, color blindness, color vision test or the like.

EXAMPLES

A preferred and optional embodiment of the present invention utilizing the method described in FIG. 3 utilizing system 120 of FIGS. 1A-B and testing a visual field map comprising 13 visual field points, FIG. 2A, is described herein below with respect to Glaucoma and RP, in determining a ratio, namely red to blue. The test protocol comprises at least one and up to three stimuli sessions, as shown with directional arrow 310, wherein the stimuli comprises at least two wavelengths to stimulate at least 13 visual field points (FIG. 2A) to simulated each eye individually. Most preferably the wavelengths utilized comprise a first long wavelength chromatic beam, in the red range, and a second short wavelength chromatic beam, in the blue range. Optionally the first and second stimulus are presented in alternating fashion for each visual field points at the outermost 30° visual field ring 208 and sequentially toward the central field ring 202.

Optionally and more preferably the first stimuli may be a short wavelength chromatic stimulus in the blue range, for example about 475 nm, while the second stimuli may be a long wavelength chromatic stimulus in the red range, for example about 650 nm. Optionally the first stimuli may be a long wavelength chromatic stimulus in the red range, for example about 650 nm, while the second stimuli may be a short wavelength chromatic stimulus in the blue range, for example about 475 nm.

Optionally and preferably the stimulus characteristics of the first stimuli is about 480±19 nm, duration of about 1 s (one second); inter-stimuli delay of about 1023 ms (milliseconds) and intensity of $3.98 \times 10^{-8}$ cd/m. Optionally and preferably the stimulus characteristics of the second stimuli is about 640±10 nm, duration of about 1 s (one second); inter-stimuli delay of about 891 ms (milliseconds) and intensity of $3.98 \times 10^{-8}$ cd/m². The above test specification was utilized to determine the red/blue ratio of normal, RP and Glaucoma subjects to evaluate the system and method according to optional embodiments of the present invention.

Example 1—Normal Subjects

The system and method described in FIGS. 1-3 was tested on subjects having a healthy eye. In total 25 eyes from 14 subjects were tested, 6 females and 8 males, with a mean age 29.8 years. The stimulus provided was as follows: the first stimulus characteristics were a chromatic beam having a wavelength of 480±19 nm, duration of about 1 s (one second), provided three times; inter-stimuli delay of 1023 ms (milliseconds) and intensity of $3.98 \times 10^{-8}$ cd/m; and the second stimulus characteristics were a chromatic beam having a wavelength of 640±10 nm, duration of about 1 s (one second); inter-stimuli delay of 891 ms (milliseconds) and intensity of $3.98 \times 10^{-8}$ cd/m².

Figure 4A:
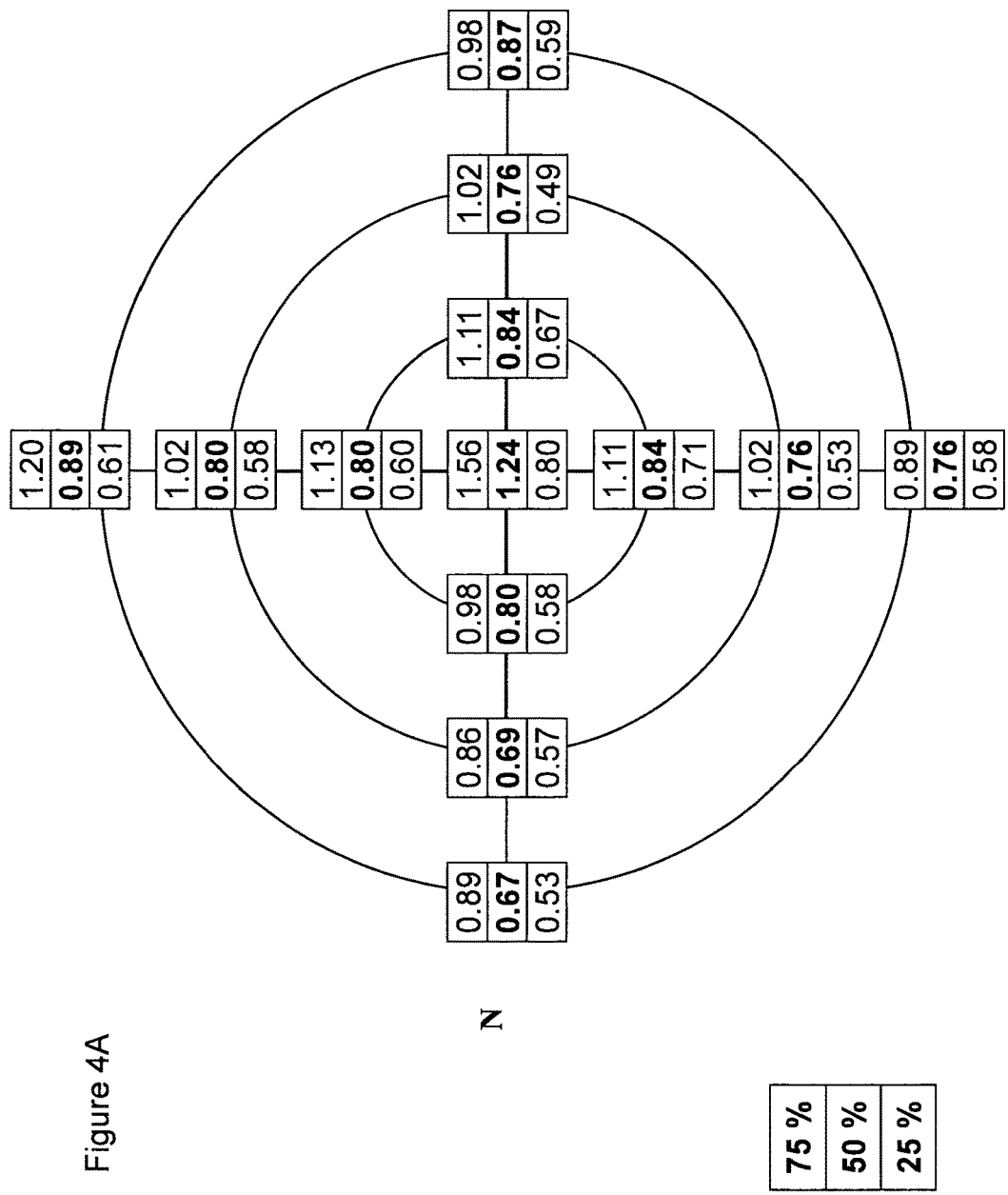
FIGS. 4A-C are schematic illustrative visual field diagrams showing results obtained from healthy normal eyes within the 50th, 75th and 25th percentiles.
Figure 4B:
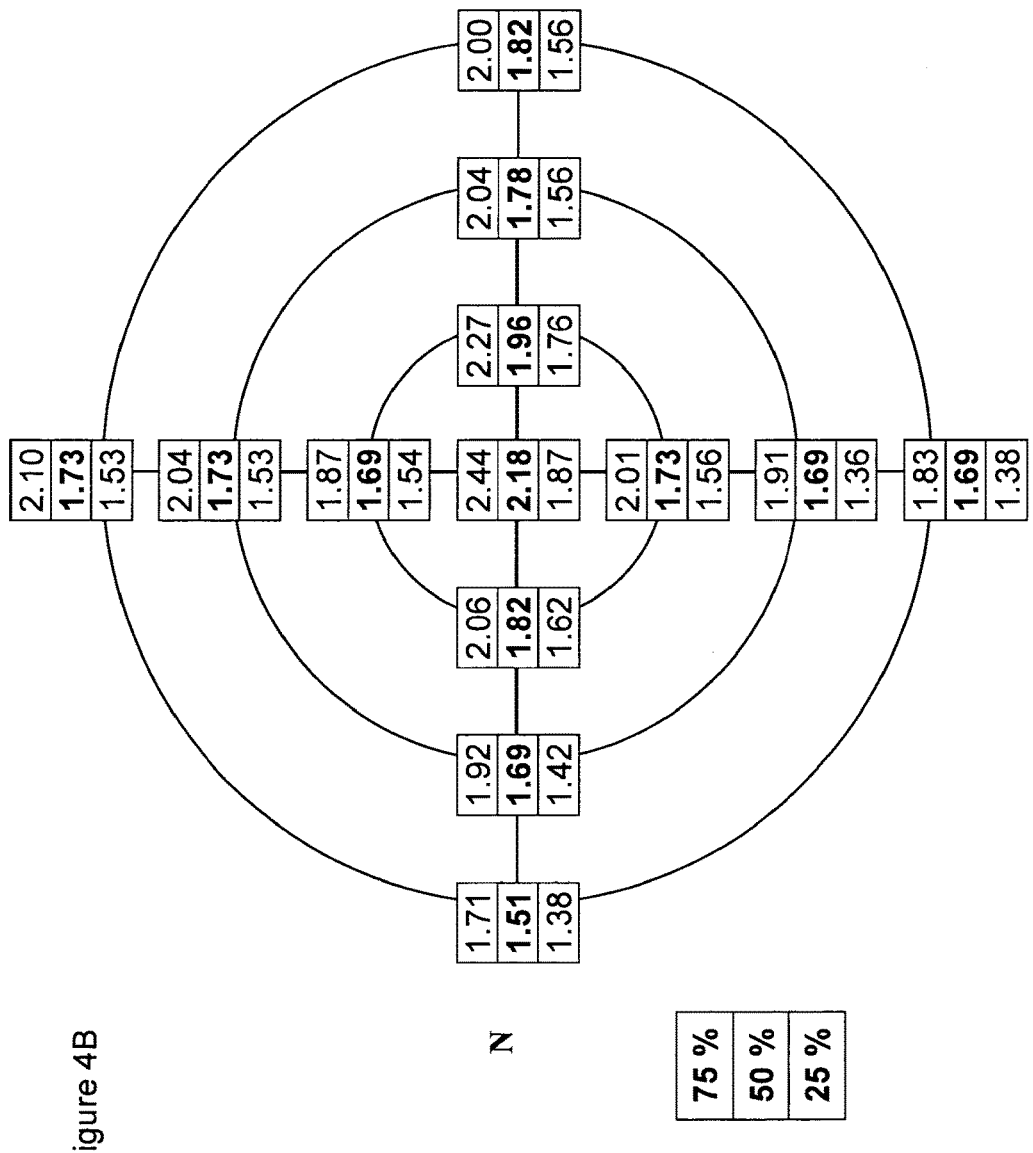

The visual field map was generated for both first and second stimuli,

FIG. 4A shows the objective PLR response obtained with the second stimuli, while FIG. 4B shows the objective PLR response obtained with the first stimuli. Both FIGS. 4A and 4B show the respective population percentile score in $75^{th}$ percentile, $50^{th}$ percentile and $25^{th}$ percentile.

Figure 4C:
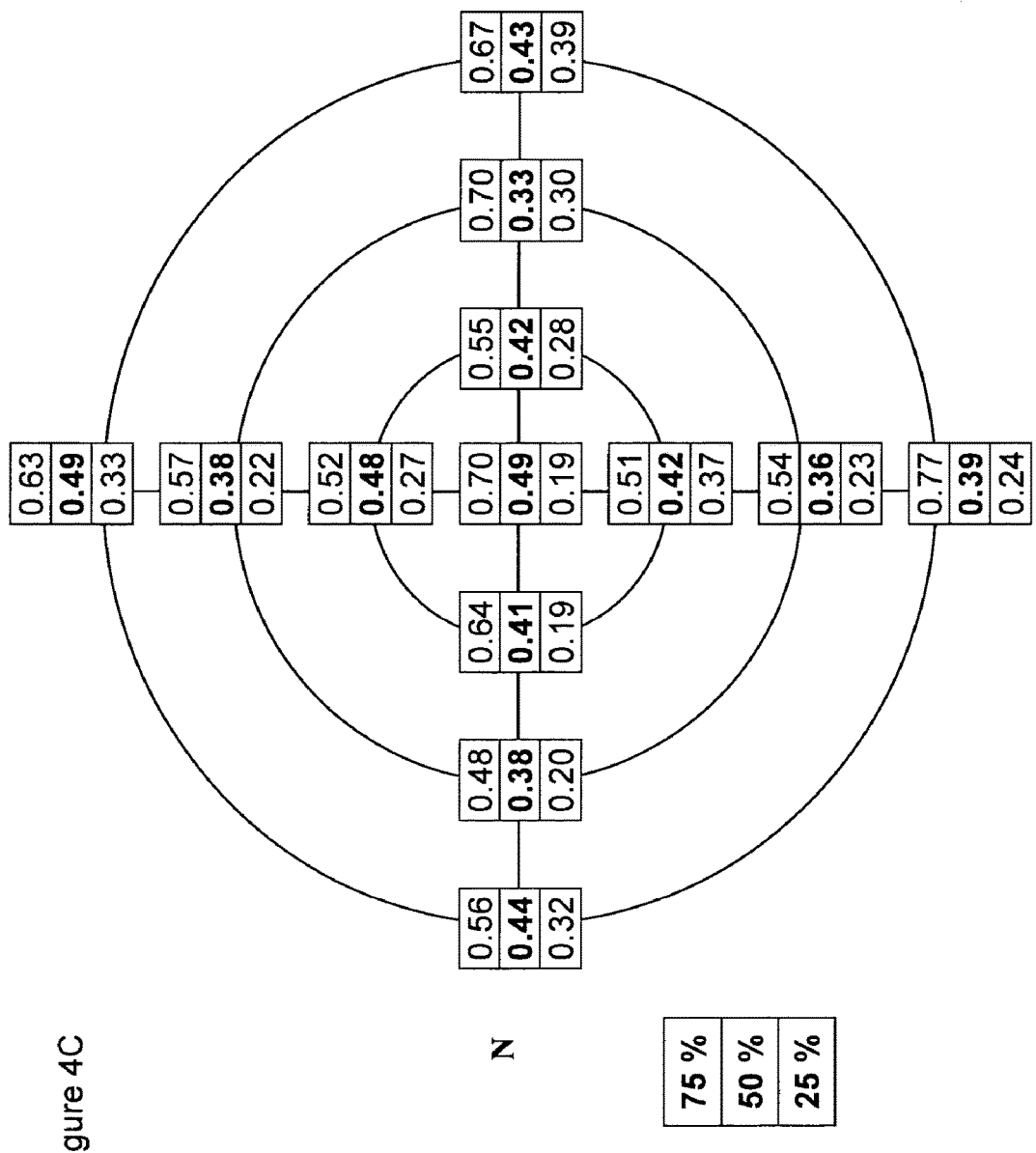

FIG. 4C shows the objective PLR response ratio obtained when comparing the response to the second stimuli with the response to the first stimuli. The visual field map of FIG. 4C shows that the $50^{th}$ percentile ratio is highest at the center of the visual field is 0.5 and gradually reduces as the visual field map extends to the 30° viewing angle. The results summarized and presented in Table 1 below:

TABLE 1

| | | Normal ratio. | | | |
|---|---|---|---|---|---|
| | | Nasal | Temporal | Up | Down |
| Normal | 0° | 0.5 | | | |
| | 10° | 0.41 | 0.45 | 0.48 | 0.43 |
| | 20° | 0.40 | 0.33 | 0.38 | 0.39 |
| | 30° | 0.5 | 0.44 | 0.5 | 0.4 |

The ratio obtained in normal healthy eyes according to the system and method of the present application provides a basis with which individuals with damaged eyes may be compared.

Example 2—Retinitis Pigmentosa Subjects

The system and method described in FIGS. 1-3 was tested on subjects with diagnosed Retinitis Pigmentosa ("RP"). In total 17 eyes were tested from 11 subjects, 4 female and 7 male, with a mean age of 34.3 years. The stimulus tested was as follows: the first stimulus characteristics were a chromatic beam having a wavelength of 480±19 nm, duration of about 1 s (one second), provided three times; inter-stimuli delay of 1023 ms (milliseconds) and intensity of $3.98 \times 10^{-8}$ cd/m$^2$; and the second stimulus characteristics were a chromatic beam having a wavelength of 640±10 nm, duration of about 1 s (one second); inter-stimuli delay of 891 ms (milliseconds) and intensity of $3.98 \times 10^{-8}$ cd/m$^2$.

Figure 5A:
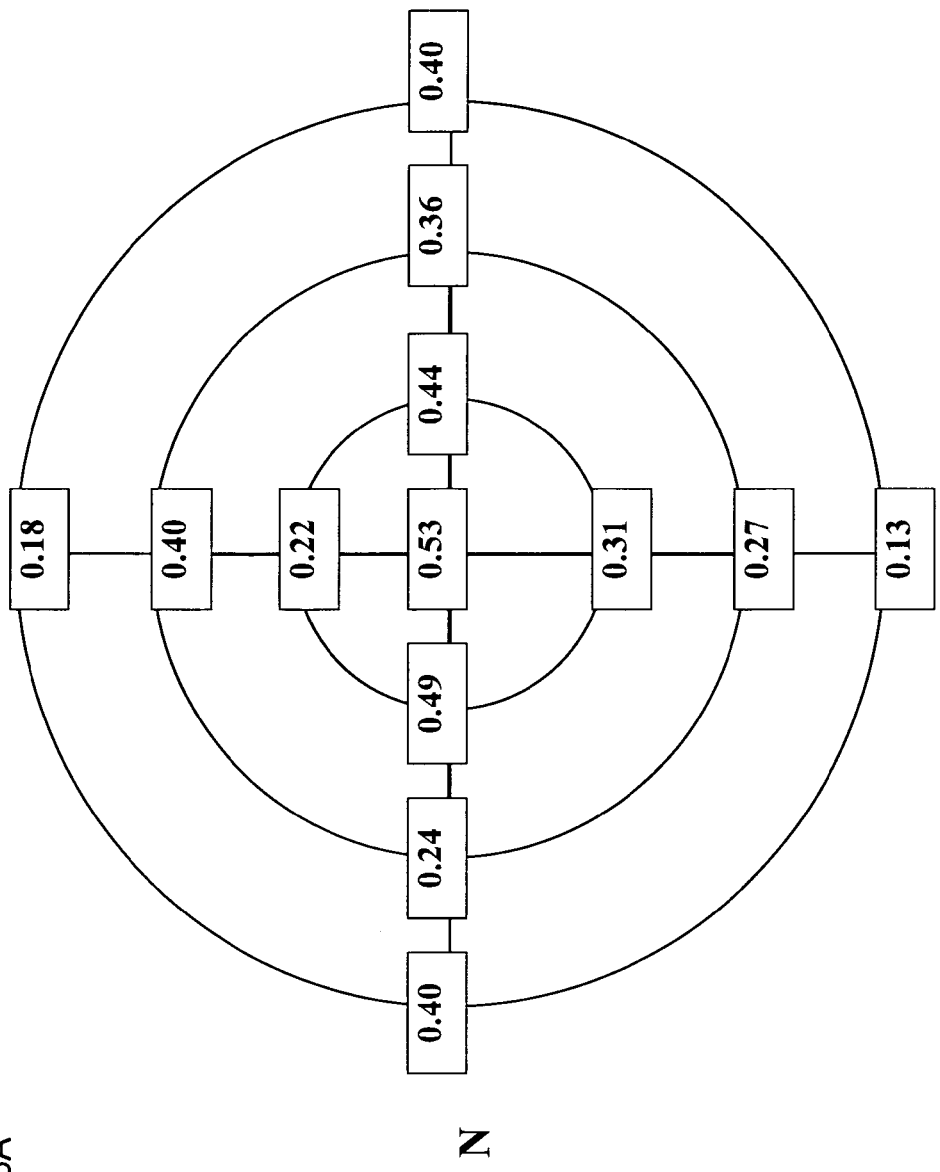
FIG. 5A-C are schematic illustrative visual field diagrams showing results obtained from subjects presenting with retinitis pigmentosa ("RP").
Figure 5B:
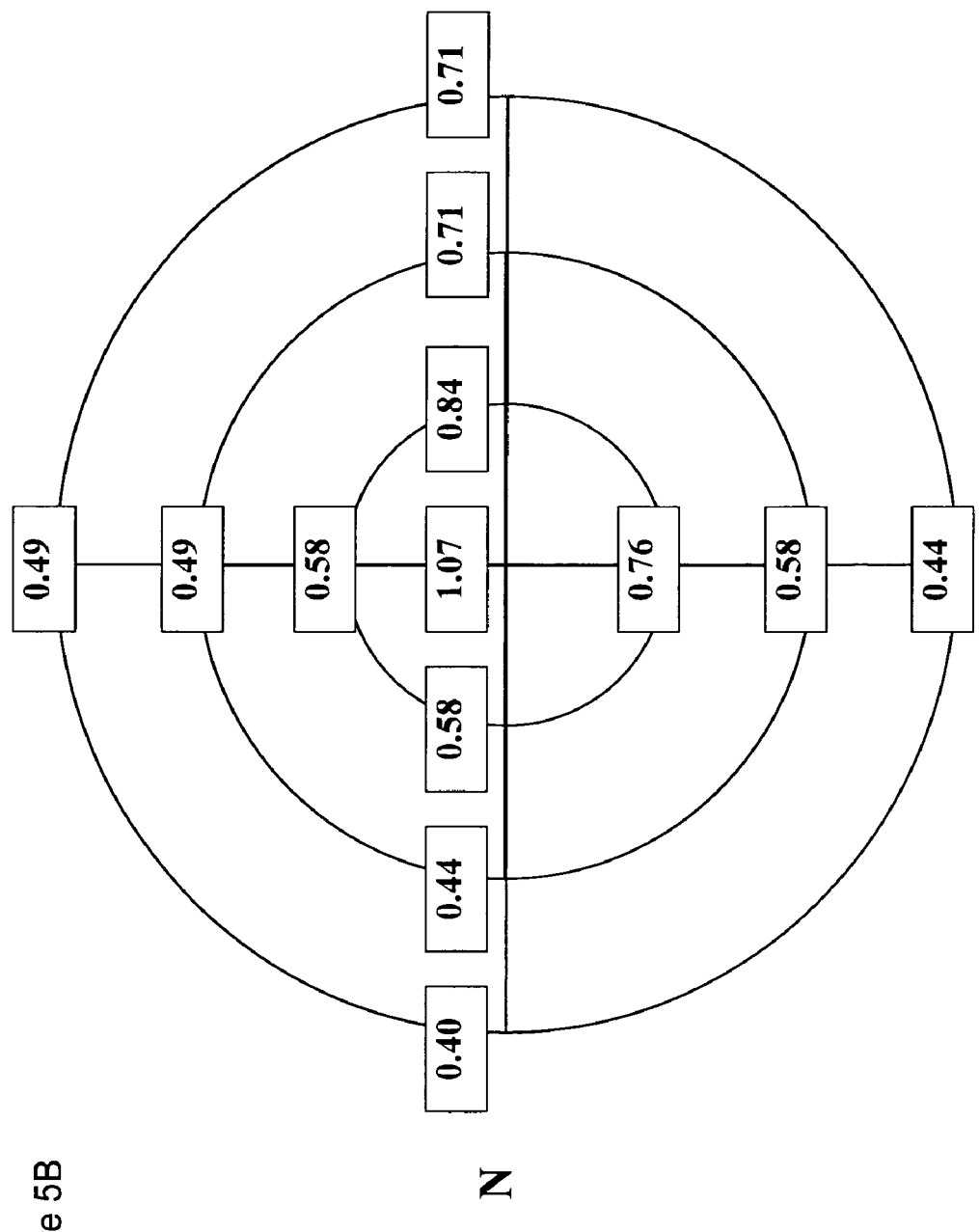
Figure 5C:
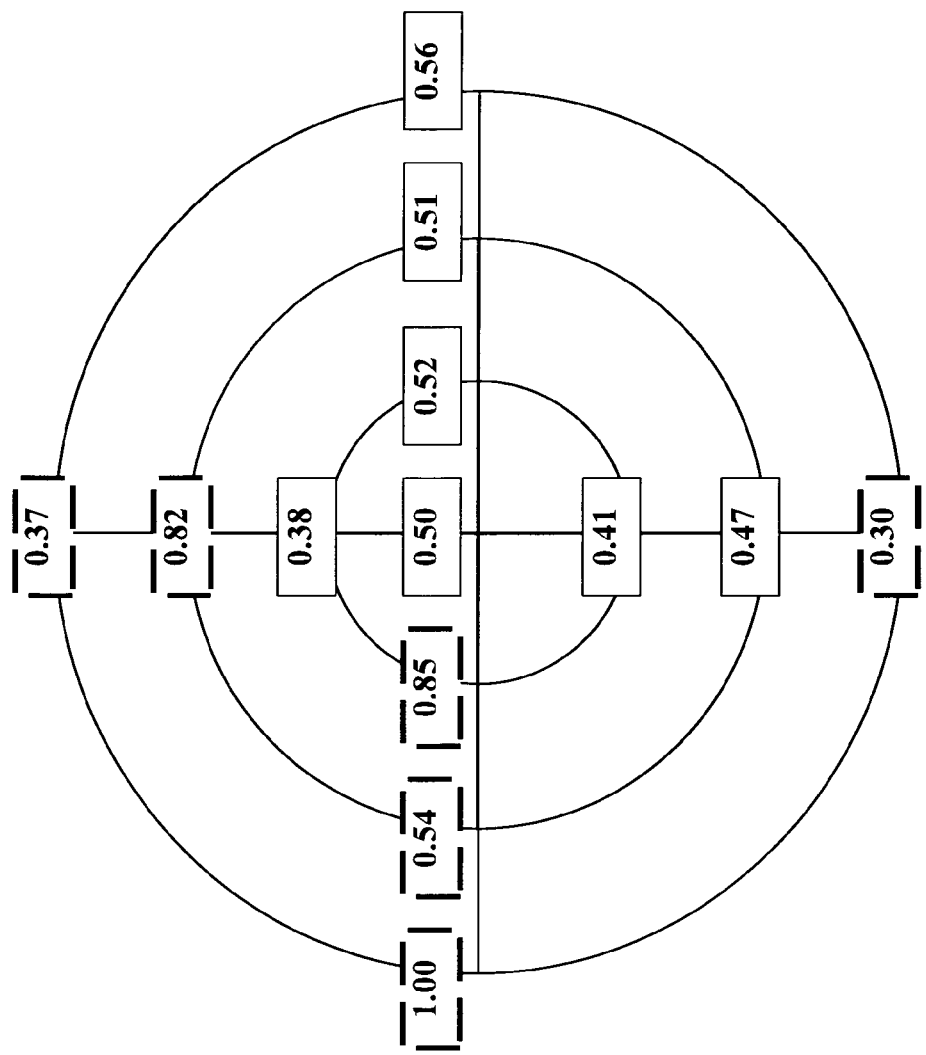

The visual field map was generated for both first and second stimuli in all subjects. An example taken from one subject is provided in FIGS. 5A-D. FIG. 5A shows the objective PLR response obtained with the second stimuli, while FIG. 5B shows the objective PLR response obtained with the first stimuli. The visual field maps obtained and displayed in FIGS. 5A-B were then utilized to calculate a ratio for the tested subject and displayed in FIG. 5C. A comparison of FIG. 5C for a subject diagnosed with RP with that of an otherwise health subject as shown in FIG. 5C clearly identifies the problem areas within the visual field, marked with a bold dashed line, that were shown to be significantly different from the measurement of the normal subjects. Therefore the ratio calculated according to the present invention provides a practitioner with the ability to identify the specific problematic areas within the visual field and possibly to isolate and provide treatment accordingly, not visible with the standard RP full field visual test.

Table 2 below provides a comparative table showing the visual field ratios results of subjects with normal visions versus those diagnosed with RP.

TABLE 2

Normal ratio vs. RP ratio.

|  |  | Nasal | Temporal | Up | Down |
|---|---|---|---|---|---|
| Normal | 0° | 0.5 |  |  |  |
|  | 10° | 0.41 | 0.45 | 0.48 | 0.43 |
|  | 20° | 0.40 | 0.33 | 0.38 | 0.39 |
|  | 30° | 0.5 | 0.44 | 0.5 | 0.4 |
| RP | 0° | 0.5 |  |  |  |
|  | 10° | 0.52 | 0.54 | 0.56 | 0.59 |
|  | 20° | 0.53 | 0.62 | 0.71 | 0.42 |
|  | 30° | 0.69 | 0.64 | 0.54 | 0.91 |

The utility in adapting the ratio provided by the system and method of the present invention as a test for diagnosing subjects with RP is provided in Table 3 below, showing that specificity and sensitivity of the objective ratio test produces promising results.

TABLE 3

Sensitivity and Specificity of Ratio test of Normal vs. RP subjects

|  |  | Subjective VF | |
|---|---|---|---|
| Red/Blue |  | Positive | Negative |
| Pupillometer | Positive | 56 | 14 |
| Based VF | Negative | 15 | 58 |
|  |  | Sensitivity = 78.9% | Specificity = 80.5% |

The average of the PLR ratio in the normal subjects was 0.41+/−0.2 (Average+SD). The average of the PLR ratio measurements of the patients in the seeing area of the visual fields was 0.62+/−0.25 and in the non-seeing area 0.97+0.2. The PLR ratio was significantly different between the normal subject and the RP patients and between seeing areas and non-seeing areas in the visual fields of the RP patients (ANOVA, p<0.001).

Example 3—Glaucoma Patient

The system and method described in FIGS. 1-3 was tested on subjects with diagnosed Glaucoma. In total 5 eyes were tested from 3 subjects, 1 female and 2 male, with a mean age of 66.5 years. The stimulus tested was as follows: the first stimulus characteristics were a chromatic beam having a wavelength of 480±19 nm, duration of about 1 s (one second), provided three times; inter-stimuli delay of 1023 ms (milliseconds) and intensity of $3.98 \times 10^{-8}$ cd/m; and the second stimulus characteristics were a chromatic beam having a wavelength of 640±10 nm, duration of about 1 s (one second); inter-stimuli delay of 891 ms (milliseconds) and intensity of $3.98 \times 10^{-8}$ cd/m$^2$.

Figure 6A:
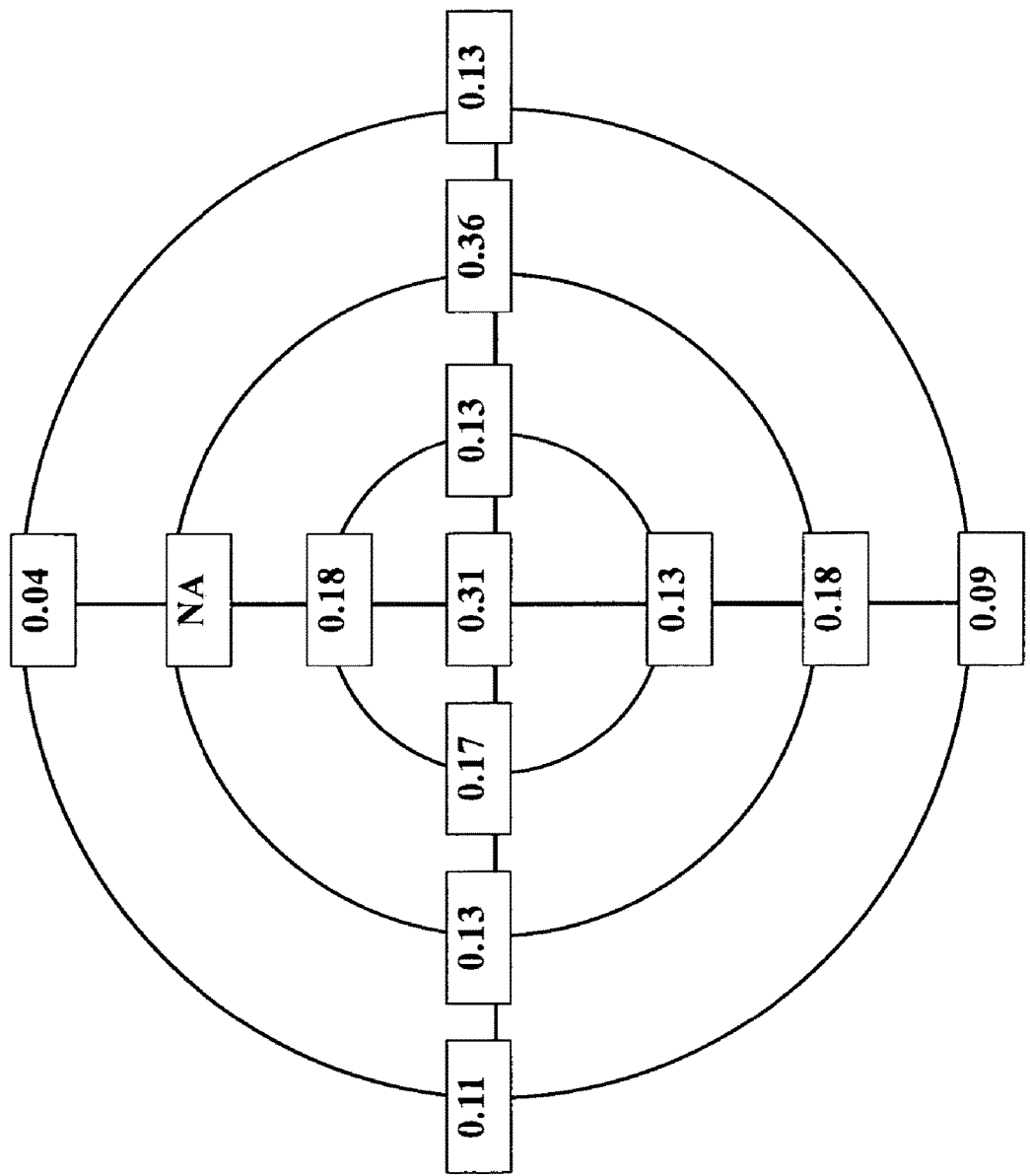
FIG. 6A-D are schematic illustrative visual field diagrams showing results obtained from subjects presenting with glaucoma.
Figure 6B:
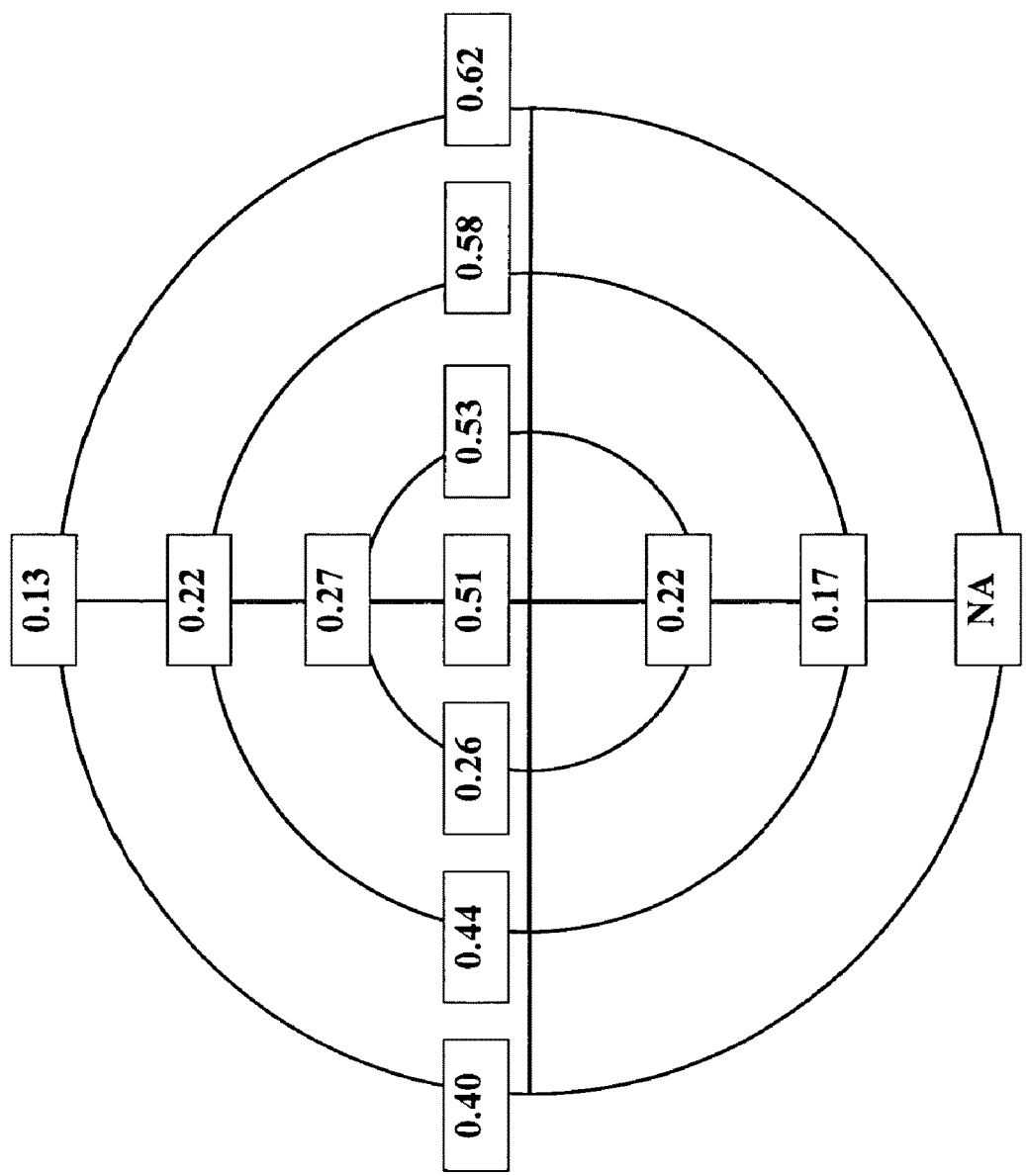
Figure 6C:
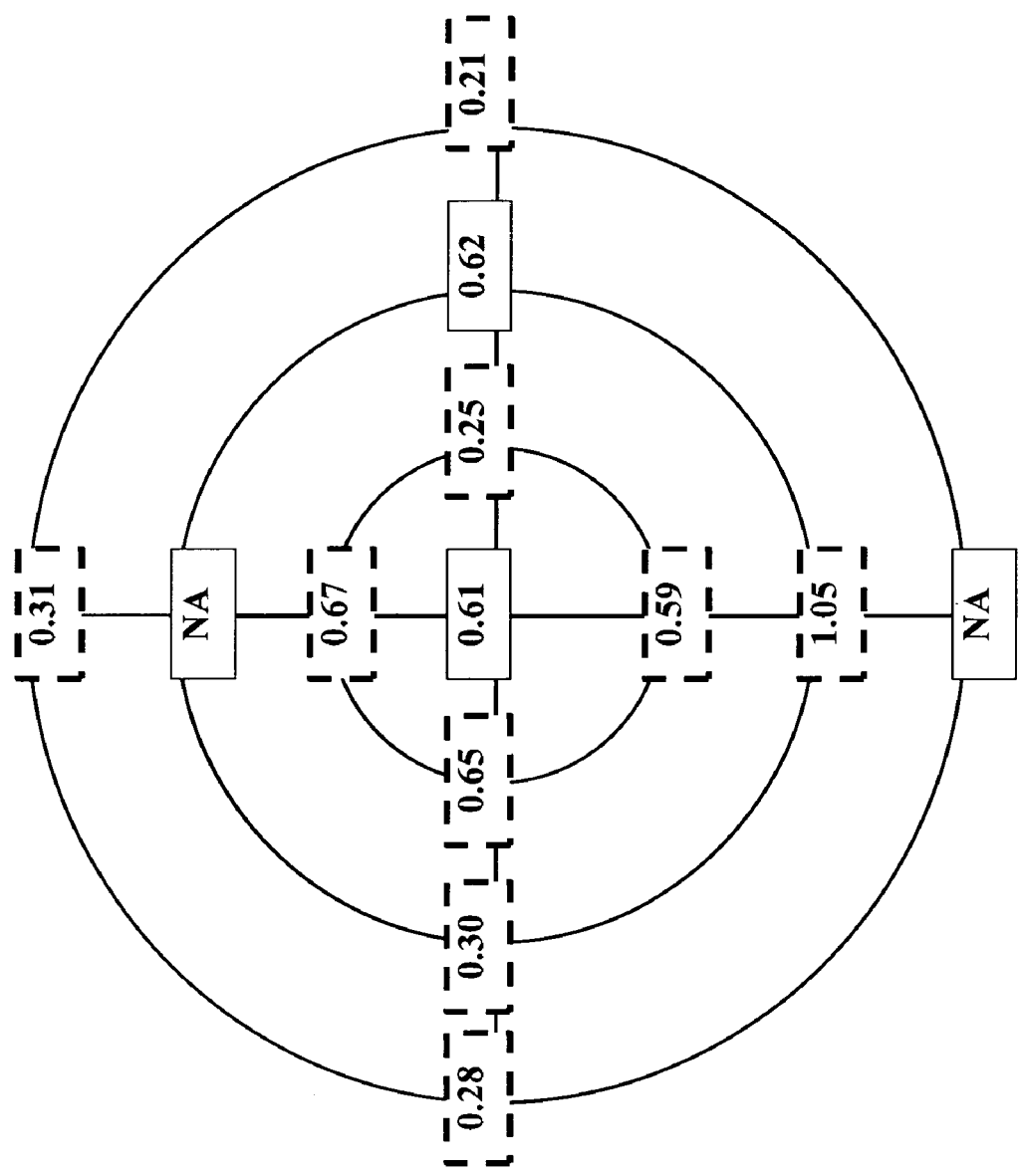

The visual field map was generated for both first and second stimuli in all subjects. An example taken from one subject is provided in FIGS. 6A-D. FIG. 6A shows the objective PLR response obtained with the second stimuli, while FIG. 6B shows the objective PLR response obtained with the first stimuli. The visual field maps obtained and displayed in FIGS. 6A-B were then utilized to calculate a ratio for the tested subject and displayed in FIG. 6C. A comparison of FIG. 6C for a subject diagnosed with Glaucoma with that of an otherwise health subject as shown in FIG. 6C clearly identifies the problem areas within the visual field, marked with a bold dashed line, that were shown to be significantly different from the measurement of the normal subjects, FIG. 4C. Therefore the ratio calculated according to the present invention provides a practitioner with the ability to identify the specific problematic areas within the visual field and possibly to isolate and provide treatment accordingly.

Figure 6D:
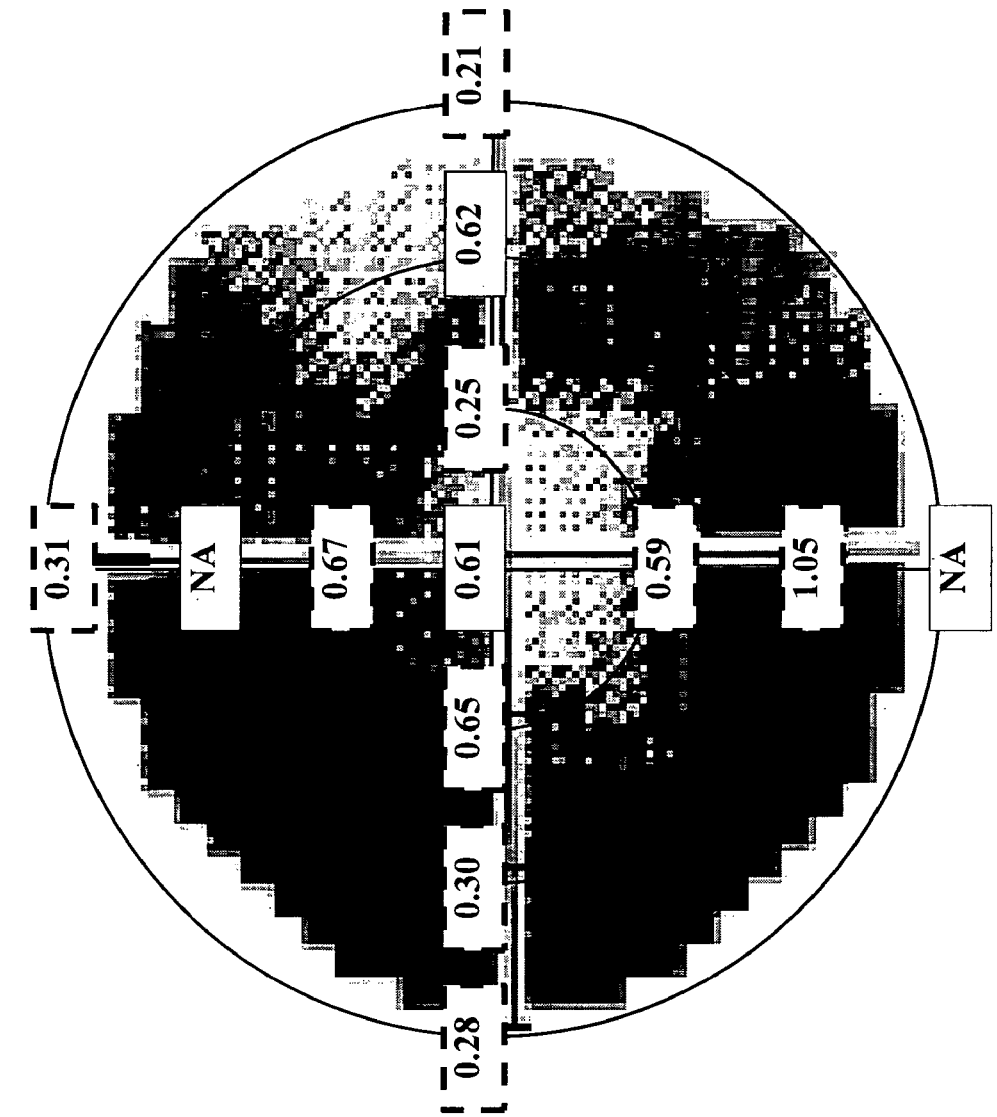

FIG. 6D provides comparative depictions showing the visual field map independently obtained from a glaucoma subject superimposed with the ratio determined according the system and method of the present invention as shown in FIG. 6C. The glaucoma subject's visual map, provided by the gold standard test, is provided as a grayscale image depicting visual sensitivities of the retina in shades of gray. Areas of very poor retinal sensitivity are darkly shaded, and areas of good retinal sensitivity are lightly shaded. The superimposed images, FIG. 6D, of the two methods shows that areas where the ratio is significantly different from the norm is indicative of problem areas as the visual maps correspond to one another. Specifically the lightly shaded area indicating good retinal sensitivity is paralleled in that the ratio determined for those visual field spots is within the norm.

Accordingly, the method and system for determining the ratio of a long wavelength chromatic stimuli to a short wavelength chromatic stimuli provides an improved way of diagnosing and elucidating an underlying problem within the eye anatomy, that provides a method for subjectively testing at least one eye. While the invention has been described with respect to a limited number of embodiments, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, and all suitable modifications and equivalents may be resorted to, falling within the scope of the invention.

Various applications of the present invention will now be described with reference to additional exemplary embodiments, including: (i) a method and apparatus for brain-injury detection; (ii) a portable apparatus for objective chromatic perimetry analysis; (iii) a method and apparatus for objective chromatic perimetry analysis in non-human animals; (iv) a method and apparatus for veterinary objective chromatic perimetry analysis; (v) a method and apparatus for assessing contrast sensitivity (e.g., regarding candidacy for intra-ocular lens (IOL) implantation and/or evaluation of IOL-implantation results); (vi) a method and apparatus for evaluation of zero-gravity brain trauma; (vii) a method and apparatus for evaluation of blue light-filtering intra-ocular lenses (IOLs); (viii) a method and apparatus for evaluating correlation of aging, ipRGC function, and circadian rhythms; (ix) a method and apparatus for mapping photosensitive retinal ganglion cells (RGCs); and (x) a method and apparatus for assessing visual acuity.

Example 4—Retinal Photoreceptor Dystrophy Patients

The system and method described in FIGS. 1-3 was tested on subjects with diagnosed Retinal Photoreceptor Dystrophy. Thirty-two eyes of 17 retinitis pigmentosa (RP) or cone-rod dystrophy patients and 20 eyes of 12 healthy individuals were tested. A computerized infrared video pupillometer was used to record changes in pupil diameter in response to short- and long-wavelength stimuli (peak 485 and 640 nm, respectively; light intensity 40 $cd/m^2$) at 13 different points of the 30° visual field (VF), under background illumination of 2.7 $cd/m^2$. The pupillary response (PR) of patients was compared with PR obtained from normal control participants. In 11 patients, the pupillary responses were also compared with their findings on dark-adapted chromatic Goldmann perimetry.

Significantly reduced pupillary responses were obtained in RP patients in response to the short-wavelength stimulus in nearly all perimetric locations ($P<0.03$). By contrast, in response to the long-wavelength stimulus, RP patients demonstrated significantly reduced PR mostly in peripheral locations ($P\le0.02$). In a cone-rod dystrophy patient, the PR to both long- and short-wavelength stimuli was significantly lower in the scotoma area identified by the dark-adapted chromatic Goldmann perimetry. In all patients that were tested by the chromatic Goldmann, minimal PR was recorded in areas that were nondetected in the chromatic Goldmann perimetry.

This study demonstrates the potential feasibility of using pupillometer-based chromatic perimetry for objectively assessing VF defects and retinal function in patients with retinal dystrophies.

Evaluation of visual field (VF) defects is important for clinical diagnosis and monitoring of various ophthalmologic diseases.

VF is assessed mainly by subjective perimetry techniques, including standard automated perimetry and short-wavelength automated perimetry. Two insurmountable limitations of these methods are the need for patient cooperation and the subjectivity of patients' responses. Therefore, testing of young children, the elderly, and individuals with compromised communication is almost certain to yield unreliable results.

Moreover, patients' responses can be affected by their levels of fatigue, wakefulness, and attentiveness during the long procedure. Hence, constant monitoring and instruction of participants by suitably qualified personnel are needed to obtain reliable results. Furthermore, test-retest variability, particularly in peripheral locations and in regions of VF deficits, makes it difficult to determine whether the VF is worsening over the course of serial examinations.

Frequent examinations are needed and misdiagnosis of early stages is common.

Unfortunately, in routine clinical practice the frequency of VF examinations varies considerably, further emphasizing the need for new technological advances that allow earlier and objective detection of VF defects and their progression with higher levels of certainty than are currently available.

The pupillary light reflex is an objective indicator of retinal and optic nerve functions. Several studies used a pupillometer with achromatic stimulus for objective determination of the visual field. However, a comparison between visual and papillary sensitivity revealed that they are not sufficiently correlated to be of clinical use. A different method of multifocal pupillographic perimetry (TrueField Analyzer; Tektronix, Beaverton, Oreg.) uses white and colored stimuli analyzing both eyes simultaneously. Although this technology is promising, it cannot differentiate between the rod and cone systems.

Kardon et al., using full-field stimuli, developed a protocol for assessing the contribution of rods, cones, and melanopsin ganglion cells to the pupillary response (PR). These studies provided evidence that the PR to different wavelengths, stimulus intensities, and stimulus durations reflects activation of different outer and inner retinal cells. It was suggested that the transient PR to a low-intensity, short-wavelength stimulus reflects rod activity, that the transient PR to a long-wavelength stimulus is predominantly driven by cones, and that a sustained PR to a continuous high-intensity short-wavelength stimulus is derived primarily from the direct intrinsic activation of melanopsin-containing retinal ganglion cells (mRGCs).

These and similar protocols were successfully used to assess the function of outer and inner retinal cells in patients with retinitis pigmentosa (RP) and patients with RPE65 mutations.

However, because these methods use a wide light source that stimulates the entire retina, they are not applicable for multifocal testing to identify VF defects.

In a previous study we demonstrated that a modified Goldmann dark-adapted chromatic perimeter can be used to identify cone or rod VF defects. Here, we tested the possibility of using a novel chromatic perimetry technique in which the retina was stimulated in a multifocal pattern by using a narrow (64 $mm^2$) light beam at different wavelengths.

Use of this narrow beam resulted in generation of an objective VF test. The PR in this modified system (dark-adaptometer; Roland Consult Stasche & Finger GmbH, Brandenburg, Germany) was automatically recorded at various VF locations.

We compared between normal participants and patients with RP or cone-rod dysfunction. We also associated the chromatic pupillometer-based perimetry findings of patients with their electroretinography (ERG), and dark-adapted chromatic Goldmann perimetry recordings.

Twenty eyes of 12 normal healthy age-matched (P ¼ 0.067 compared with patients) volunteers (six males, six females; mean 6 SD age: 38 6 14.4 years; range: 25-65 years) were included in the study. Four participants could not have both eyes tested. Inclusion criteria were normal eye examination, best-corrected visual acuity (BCVA) of 20/20, normal color vision test (Roth-28-hue test), no history of past or present ocular disease, no use of any topical or systemic medications that could adversely influence efferent pupil movements, and normal 24-2 Swedish Interactive Threshold Algorithm (SITA), developed for the Humphrey standard perimeter (Humphrey Field Analyser II, SITA 24-2; Carl Zeiss Meditec, Inc., Jena, Germany).

The study group (eight males and nine females; mean 6 SD age: 48.8 6 15.5 years; range: 27-72 years) comprised 30 eyes of 16 patients with RP and two eyes of a patient with cone-rod dystrophy. Inclusion criteria for RP patients were typical abnormal fundus appearance and a previously recorded ERG that was abnormal under scotopic or photopic conditions or both (in compliance with the protocol of the International Society for Clinical Electrophysiology of Vision, which specifies the absence or diminution of b-wave amplitude below the fifth percentile with prolonged implicit times compared with normal participants). Exclusion criteria were a concurrent ocular disease and any other condition affecting the PR. Data recorded for all patients included sex, diagnosis or genetic defect if known, and ERG responses.

Light stimuli were presented using a Ganzfeld dome apparatus (multifocal dark-adaptometer; Roland Consult Stasche & Finger GmbH) placed 330 mm from the patient's eye, and controlled with a stimulus generator and custom software. The untested eye was occluded. Stimuli were presented from the center, and participants were asked to fixate on a red light-emitting diode fixation light presented from 13 different locations in the VF (central, superior, inferior, temporal, and nasal fields at angles of 10°, 20°, and 30°). Wavelengths of the light stimuli selected for this study were 640 6 5 nm for red light (long wavelength) and 480 6 5 nm for blue light (short wavelength). A light intensity of 40 cd/m$^2$ was chosen after preliminary calibrations that enabled us to identify the minimal stimulus intensity that yielded a substantial PR in peripheral VF locations in five normal participants. Each stimulus was presented using stimulus size V (64 mm$^2$) on a background luminance of 2.7 cd/m$^2$. Stimulus duration was 1000 ms and the interstimulus interval was 10 seconds.

Pupil diameters were recorded in real time by a computerized infrared pupillometer (Roland Consult Stasche & Finger GmbH), which consisted of a monitor with viewing optics for presentation of a light stimulus to the subject. Pupil tracking was performed by an infrared high-resolution camera inside the dark-adaptometer that recorded the PR at a sampling rate of 34 Hz. The software (Roland Consult Stasche & Finger GmbH) searched for the pupil in every image. A correction factor was used to get the diameter in millimeters and pupil diameters were measured with an accuracy of 0.1 mm (Roland Consult Stasche & Finger GmbH).

The subject's eye was inclined at 15° to the center, at the position where the stimulus was presented. The subject had an uninterrupted VF in excess of 30° in all meridians. A recordable PR was obtained in both eyes of all patients except for two, both of whom had difficulty in fixating on most fixation locations in one eye. The subjects were requested to blink several times before the start of the recording and refrain from blinking during the recording. Real-time video imaging of the eye was carefully monitored by the examiner during the test. Tests in which the subject blinked were excluded and the subject was retested.

Percentage pupil contraction at each time point was determined by the formula: % pupil contraction=100 3 [The difference between the highest initial diameter at the beginning of the stimulus and the lowest diameter in response to that stimulus]/[The highest initial pupil diameter], as described by Kardon et al. Previous studies demonstrated that contraction of the pupil is a true PR when the initial pupillary contraction (time at which the maximum acceleration occurs) falls within a definite time window (200-450 ms after stimulus onset). Accordingly, we recorded pupillary contraction only when the initial pupillary contraction was within this time window. All calculations were done by an independent experienced masked technician. The test duration was approximately 5 minutes for each eye. In preliminary studies we repeated each measurement twice in normal participants and found no significant difference between repeated measurements (P>0.05, n=14). Furthermore, in all perimetry locations the PR did not significantly differ between the left and right eye (P>0.16, n=7) in the healthy participant.

Eleven patients were tested for kinetic VF by dark-adapted chromatic Goldmann perimetry. Briefly, a Goldmann perimeter (940-ST; Haag-Streit AG, Liebefeld, Switzerland) was used to map patients' conventional and two-color dark-adapted VFs. Patients were dark adapted for 30 minutes prior to testing. The setting used for stimuli were V3c for the long-wavelength stimulus and 2 log units lower in luminance (V3c) for the short-wavelength stimulus.

Statistical analysis was performed using a commercial software program (SAS for Windows, version 9.2; SAS Institute, Inc., Cary, N.C.; or SPSS for Windows, version 20.0; SPSS, Inc., Chicago, Ill.). For two-eye analysis, comparison between patients and healthy controls for all perimetry locations was performed using a one-way ANOVA with repeated measures (eye side). Since for some of the participants only one eye was examined, the mixed model was applied to address this issue. For single-eye analysis, we compared between the pupillary recordings of the right eye of patients and healthy controls for all perimetry locations using a one-way ANOVA. Agreement between the chromatic pupillometer recordings and the dark-adapted chromatic Goldmann (that yields a yes/no result) was assessed using two-sample t-test and the Mann-Whitney nonparametric test. A value of P<0.05 was considered statistically significant.

All participants easily tolerated the protocol without any discomfort. PR to the short-wavelength stimulus significantly exceeded the PR to the long-wavelength stimulus at all perimetry locations (P<0.01). Thus, the mean percentage pupil contraction in the normal participants in response to the short-wavelength stimulus was (mean±SE) 28.6±0.38%, and only 14.7±0.41% in response to the long-wavelength stimulus (FIGS. 12A, 12B).

Figure 12:
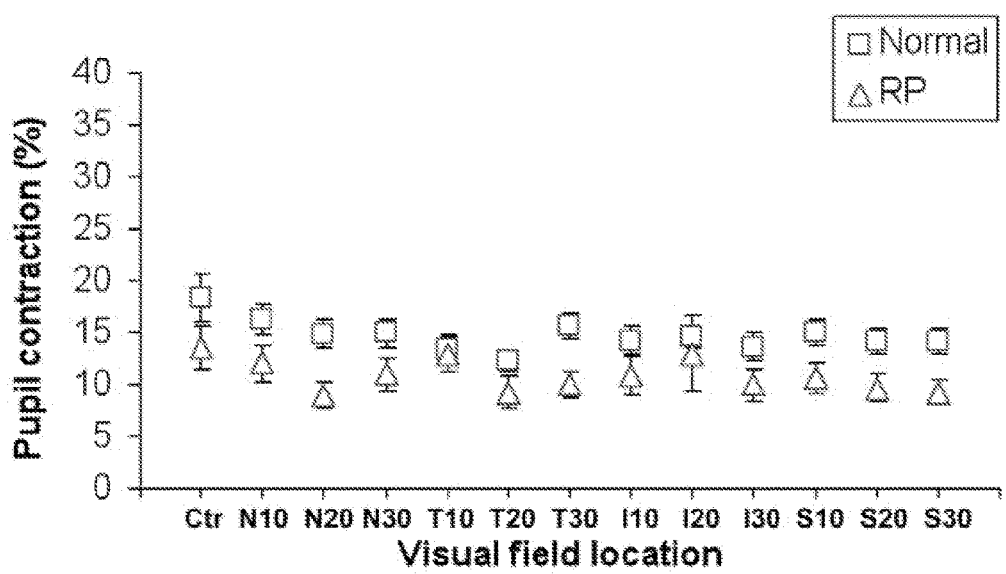
FIG. 12 shows percentage change in pupil diameter in both eyes of RP patients and normal participants in response to both long-wavelength (A) and short-wavelength stimuli (B).
Figure 12:
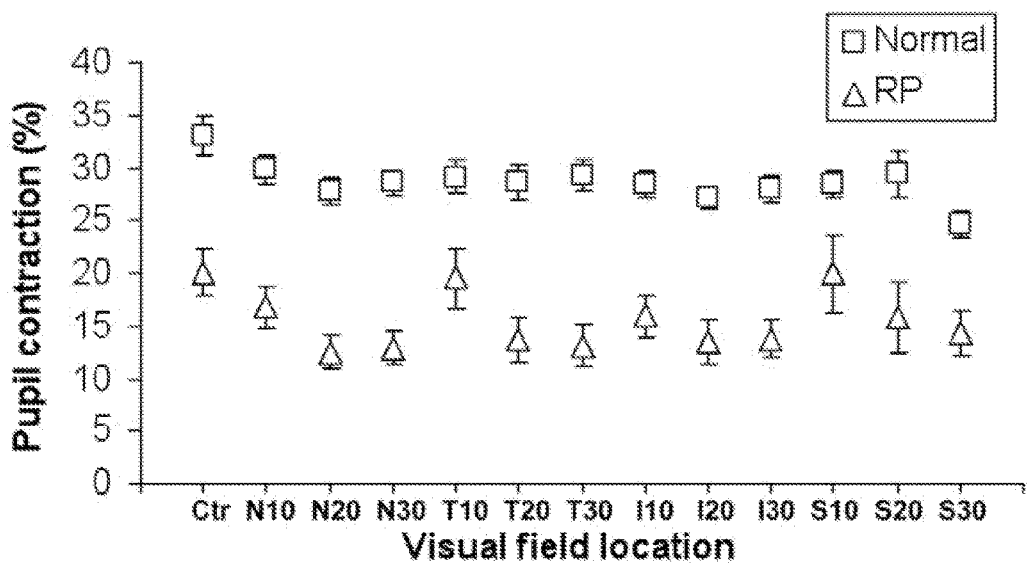
Figure 13:
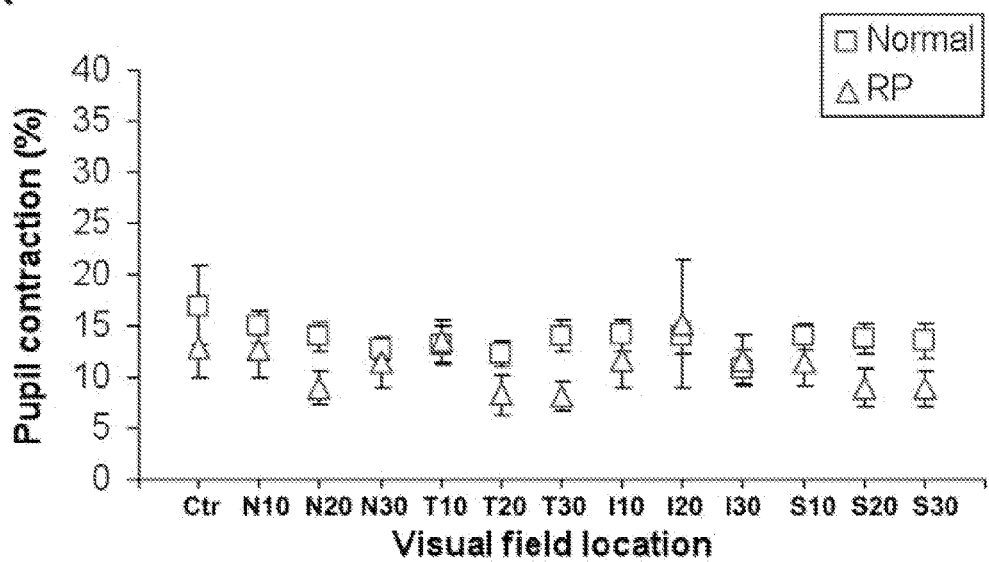
FIG. 13 shows percentage change in pupil diameter in the right eye of RP patients and normal participants in response to both long-wavelength (A) and short-wavelength stimuli (B).
Figure 13:
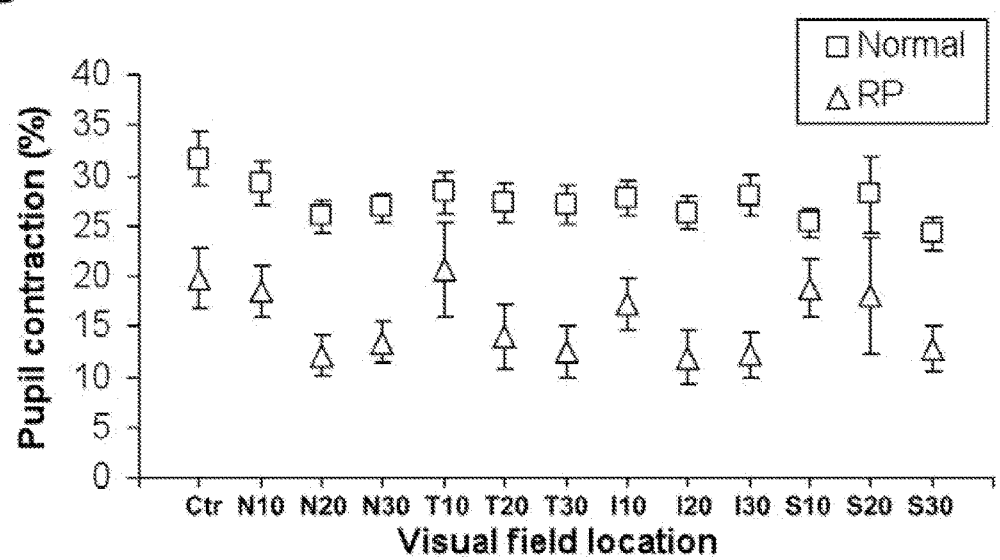

When both eyes were included in the analysis (repeated measures ANOVA), no significant differences in mean PR to the long-wavelength stimulus were observed between RP patients and normal participants in the majority of locations (P>0.05), except nasal at 20°, temporal at 30°, and superior at 30° (P≤0.02, FIG. 12A). Similar results were obtained when the pupillary responses of one eye of patients and normal participants were compared. Thus, the mean PR to the long-wavelength stimulus in RP patients was significantly lower compared with normal participants in only two locations (nasal 20° and temporal 30°, P≤0.04, FIG. 3A).

In contrast, the mean PR to the short-wavelength stimulus exhibited by the RP patients was significantly lower than the PR of control participants in all locations (P<0.03), except temporal 10°, when both eyes were analyzed (FIG. 12B). When only one eye was included in the analysis, the mean PR to the short-wavelength stimulus exhibited by the RP patients was significantly lower than the PR of control participants in a majority of locations (P≤0.011) except temporal 10° and superior at 10° and 20° (FIG. 3B). The lowest responses by RP patients were consistently recorded in peripheral locations (20° and 30°).

Figure 14:
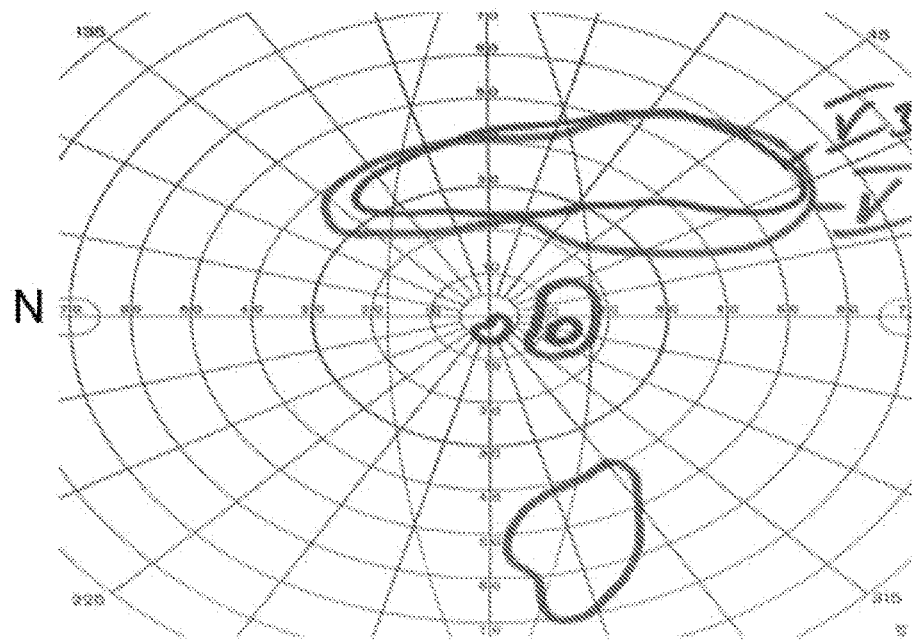
FIG. 14A shows chromatic dark-adapted Goldmann perimetry of the right eye of a study patient.
FIG. 14B shows a comparison of PR of the patient's right eye in response to both short- and long-wavelength stimuli, as a percentage of mean normal values.

To validate the novel chromatic pupillometer-based perimetry technique we compared the chromatic pupillometer recordings of 11 patients with their chromatic dark-adapted Goldmann findings. In a majority of locations the chromatic pupillometer recordings of PR to short-wavelength stimulus were in agreement with the chromatic Goldmann findings both when single-eye and two-eye analyses were performed (P<0.05; FIG. 14A). By contrast, in a majority of locations there was no significant correlation between the PR to long-wavelength stimulus and the chromatic Goldmann recordings. In all patients tested, minimal pupillary responses were recorded in areas that were nondetected in the dark-adapted chromatic Goldmann. To illustrate the pattern of recorded PR values compared with the results of chromatic Goldmann VF testing, the individual reports on three patients, two with RP and one with cone-rod dystrophy, are presented here.

Figure 14B:
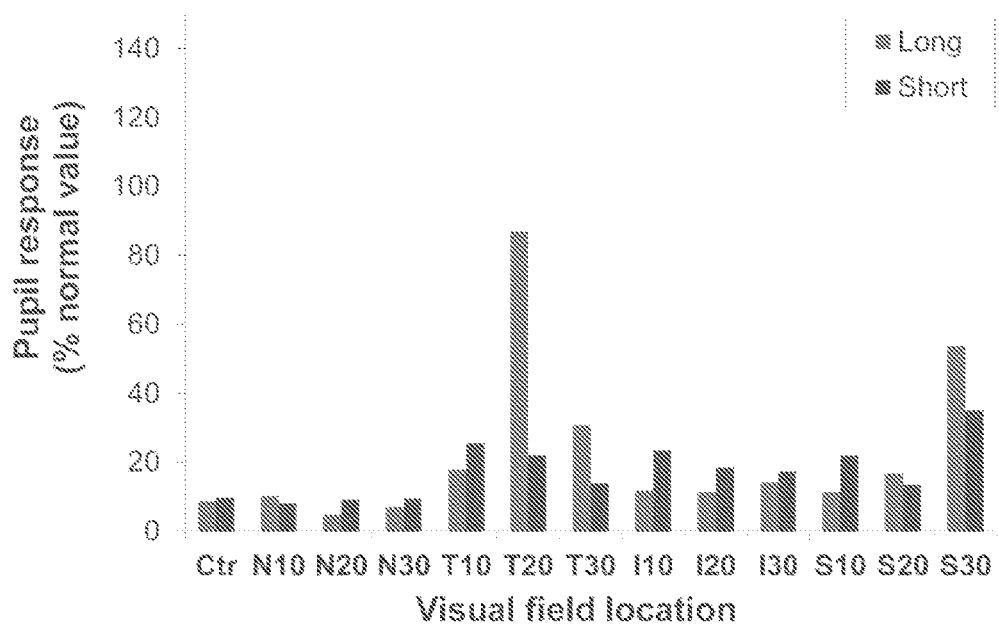
Figure 15:
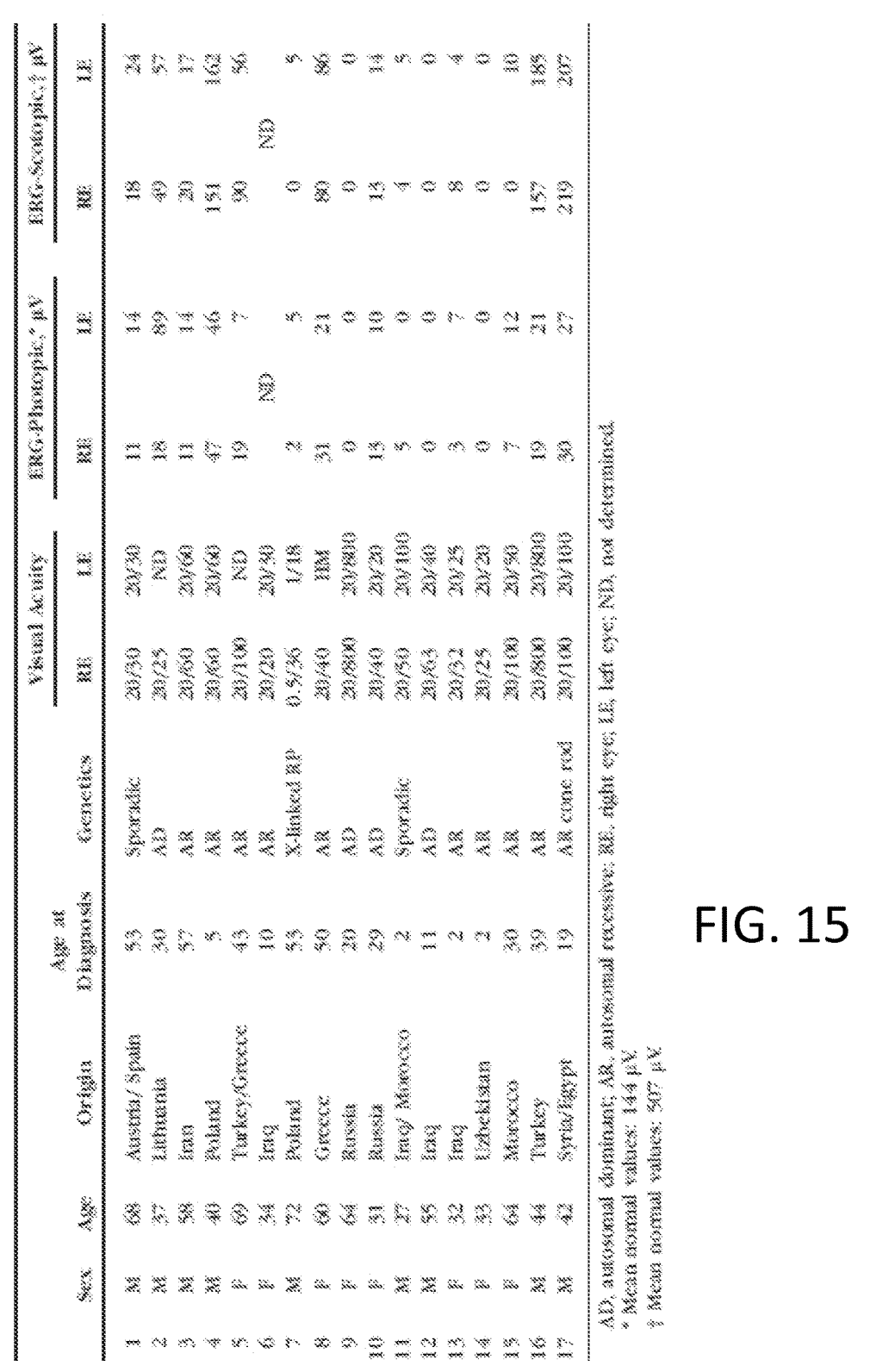

RP Patient #1: A 68-year-old white male with isolated RP had a BCVA of 20/30 in both eyes. Fundus examination demonstrated pigment epithelial atrophy, arteriolar narrowing, and bone spicules and clumps in the midperiphery of both eyes. This patient had significant ERG and VF loss (FIGS. 14A and 15). The PR of the right eye of this patient to both the long- and the short-wavelength stimuli in a majority of VF locations, was lower by over 3-fold compared with the mean PR of the right eye in the normal group (FIG. 14B). In most of the tested perimetry locations there was an agreement between the pupillometer-based perimetry and the chromatic Goldmann perimetry. Thus, the pupillometer-based perimetry showed that the PR to the long-wavelength stimulus was highest at temporal 20° and superior 30° (FIG. 4B). These locations corresponded to the areas where the long-wavelength stimulus was detectable by the chromatic Goldmann perimetry (FIG. 4A). In areas where the long-wavelength stimulus was not detected by the chromatic Goldmann (10° superior, and all inferior and nasal locations), the PR response was lower than 15% of mean normal values. Similarly, the highest pupillary responses to the short-wavelength stimulus were recorded at 30° superior and at 10° and 20° temporal, in agreement with the areas where the short-wavelength stimulus was detected by chromatic Goldmann (FIGS. 4A, 4B). The lowest PR to the short-wavelength stimulus (<10% of normal mean values) was obtained in locations that were not detected by the chromatic Goldmann (center and all nasal locations). Lower correspondence was observed in areas that were on the isopters of the chromatic Goldmann VF (temporal 10° in the long-wavelength and superior 20° for both wavelength stimuli).

Figure 16A:
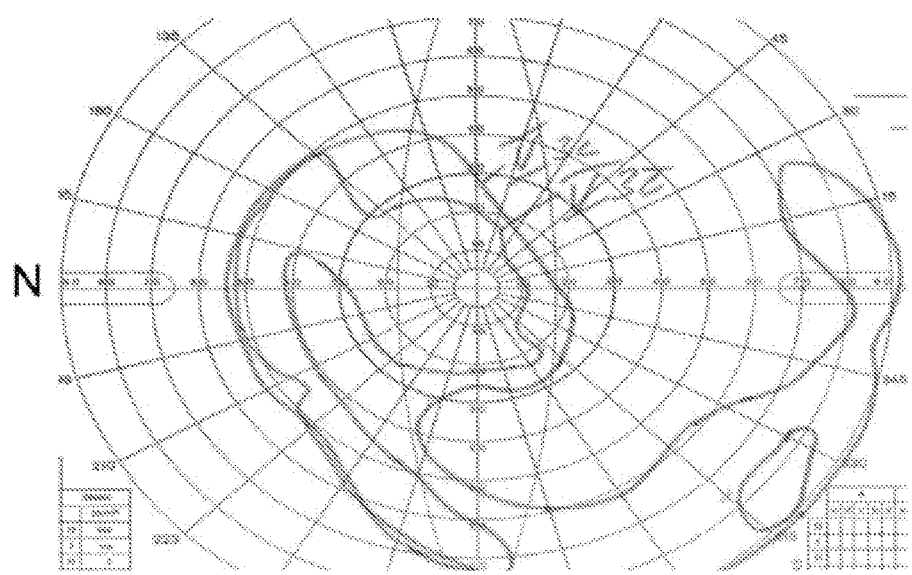
FIG. 16A shows a chromatic Goldmann perimetry of the right eye.
Figure 16B:
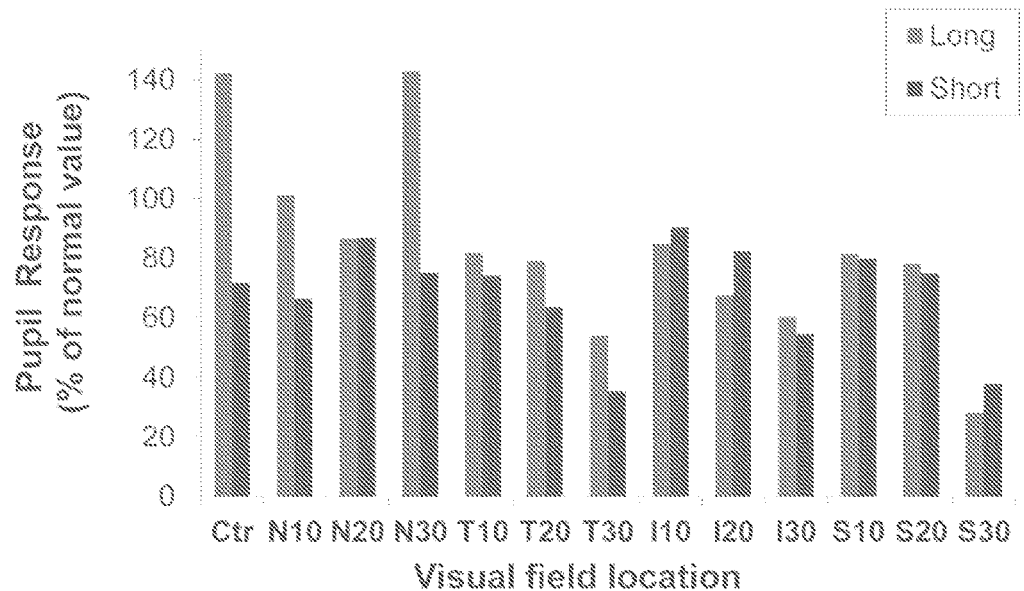
FIG. 16B shows a comparison of PR of the patient's right eye in response to both short- and long-wavelength stimuli, as a percentage of mean normal values.

RP Patient #2: A 37-year-old white male with autosomal dominant RP had a BCVA of 20/20 in both eyes. Fundus examination demonstrated pigment epithelial atrophy and bone spicules in his right eye. ERG responses were abnormal (FIG. 15) and chromatic Goldmann perimetry demonstrated characteristic constriction (FIG. 16A). In most of the locations tested there was an agreement between the pupillometer-based perimetry and the chromatic Goldmann perimetry. Thus, the PR to the long wavelength stimulus (FIG. 5C) was 75% or higher of the mean response of the right eye in normal participants at the center, at 10° and 20° in all locations, and at 30° nasal. These locations corresponded to areas where the long-wavelength stimulus was detectable on chromatic Goldmann perimetry (FIG. 16B). By contrast, in areas where the long-wavelength stimulus was nondetectable by the chromatic Goldmann or close to the isopter (30° temporal, inferior, and superior), minimal pupillary responses were recorded (54%, 60%, and 28% of mean normal values, respectively). Similar agreement was observed in the PR to the short-wavelength stimulus. In areas where the short-wavelength stimulus was detectable by chromatic Goldmann perimetry (at the center, all nasal locations, inferior 10° and 20°, and superior 10° and 20°), the recorded PR was maximal (>66% of mean normal values). The lowest pupillary responses were recorded in areas where the short-wavelength stimulus was not detectable on chromatic Goldmann perimetry (temporal 20° and 30°, superior 30°, and inferior 30°). Lower correspondence was observed in nasal 30° for the short wavelength stimulus, which was on the isopter of the chromatic Goldmann VF.

Figure 17A:
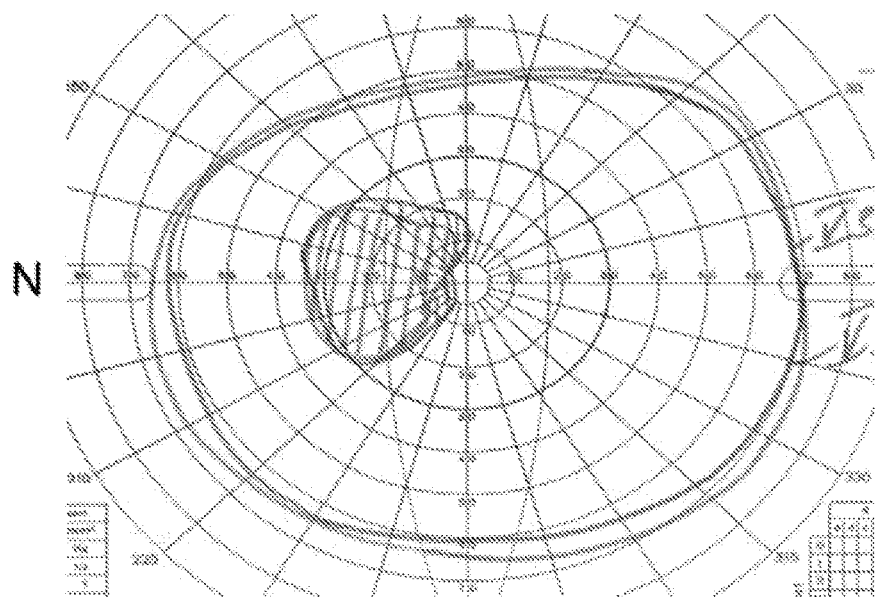
FIG. 17A shows a chromatic Goldmann perimetry of the right eye.
Figure 17B:
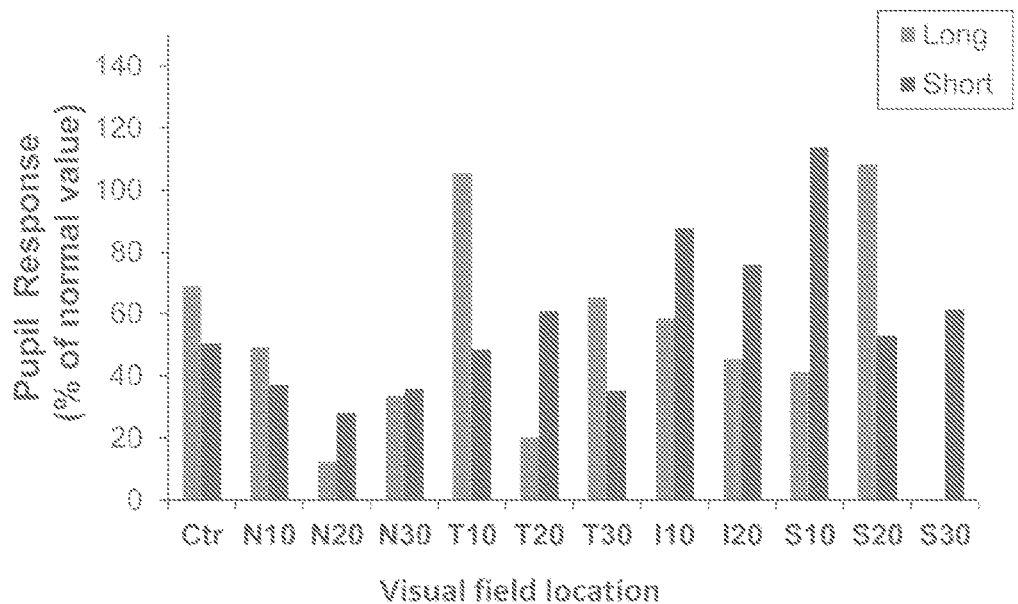
FIG. 17B shows a comparison of PR of the patient's right eye in response to both short- and long-wavelength stimuli, as a percentage of mean normal values.

Cone-Rod Dystrophy Patient #17: A 42-year-old male with autosomal recessive cone-rod dystrophy had a BCVA of 20/100 at both eyes. Fundus examination demonstrated macular pigment epithelial atrophy and chromatic Goldmann perimetry revealed a dense central scotoma and temporal parafoveal shifting of fixation (FIG. 17A). ERG responses were abnormally reduced, especially under conditions of light adaptation (FIG. 15). In his responses to both the short- and the long-wavelength stimuli, this patient demonstrated an agreement in most perimetry locations between the pupillometer-based perimetry and the chromatic Goldmann perimetry. Thus, the PR to the long-wavelength stimulus (FIG. 17B) was highest (>58% of mean normal values) in areas where the long-wavelength stimuli were detectable by chromatic Goldmann perimetry (center, 10° and 30° temporal, 10° inferior, and 20° superior). The PR to the long-wavelength stimulus was minimal (<34% of mean normal values) in areas that were nondetectable on the chromatic Goldmann (20° and 30° nasal). Lower correlation was observed in 10° nasal and 20° temporal. The 30° superior and inferior locations in this patient were not measurable, probably because of his difficulty in using a parafoveal fixation on peripheral inferior and posterior targets. An agreement between the two perimetry tests was also demonstrated in response to the short-wavelength stimulus (FIG. 17B). In areas where the shortwavelength stimulus was detectable by the chromatic Goldmann (center, 10° and 20° temporal, 10° and 20° inferior, and 30° superior), the patient exhibited maximal PR (>48% of mean normal values), whereas in areas where the short wavelength stimulus was undetectable in the chromatic Goldmann (all nasal locations), minimal PR was recorded (<37% of mean normal values). Lower correlation was observed in 10° superior that is on the isopter and at 30° temporal for the short-wavelength stimulus.

In this study we successfully used the PR to multifocal chromatic stimulus as an objective mean to perform perimetry.

RP patients exhibited significantly reduced mean PR to the short-wavelength stimulus at most locations, whereas their mean responses to the long-wavelength stimulus were similar to those of normal participants at central locations but were significantly reduced at peripheral locations. Studies from the groups of Kardon and Stieger demonstrated that transient PR to a low-intensity, short-wavelength stimulus reflects rod activity and that transient PR to a long-wavelength stimulus is predominantly driven by cones. In retinitis pigmentosa patients, the loss of rod function exceeds the reduction of cone function and VF loss typically begins with peripheral VF constriction. These findings suggest that the PR to short-wavelength stimulus measured by our chromatic pupillometer may be mediated by rods, whereas the PR to long-wavelength stimulus measured here may be mediated by cones. A clinically applicable protocol for assessing these cell contributions to the PR can be measured by a pupillometer as described herein, to enable both the objective detection of affected areas and the identification of the damaged photoreceptor cells underlying the defect in these locations.

When both eyes were analyzed, the only measurement in which the PR to short-wavelength stimulus in RP patients was not significantly lower than that in normal participants was at the temporal 10° location. This might be explained by recent optical coherence tomographic findings in RP patients showing increased outer macular thickness in the nasal quadrant, which corresponds to the temporal 10° location. In cone-rod dystrophy, the deficit in the cones far exceeds that in rods. In the cone-rod dystrophy patient described here, the decline in PR to both the long- and the short-wavelength stimuli was similar in the scotoma area, unlike our RP patients, in whom the decline in response to the short-wavelength stimulus was more pronounced, suggesting that the new perimetry method may assist in diagnosis of diseases affecting different retinal cells.

To validate the new chromatic perimetry technique we decided to compare the novel pupillometer method with an established perimetry technique. We chose the chromatic dark adapted Goldmann because it uses multifocal chromatic short and long-wavelength stimuli for perimetry determination and monitoring of patients with retinal dystrophies. We observed a good agreement between the chromatic pupillometer-based perimetry and the malfunctioning areas identified by the dark-adapted chromatic Goldmann perimetry. Furthermore, a correlation was observed between the two methods in a majority of locations in response to the short-wavelength stimulus. Our findings that the PR to a long-wavelength stimulus did not correlate in a majority of locations with the chromatic dark-adapted Goldmann, could be explained by the differences between the two methods: the Goldmann is a threshold-subjective kinetic test that yields a binary qualitative recording (yes/no result). By contrast the chromatic pupillometer is a suprathreshold, objective quantitative test. Hence, it is likely that the pupillometer can detect reduced retinal function to suprathreshold stimuli in a numeric manner. Since the response to the long-wavelength stimulus was less affected in RP patients, this difference between the two systems was more profound. In some cases the lower agreement could be explained by PR measurements in areas corresponding to the chromatic Goldmann VF isopters.

Our findings that similar results were obtained using two-eye and single-eye analyses provide further evidence for the validity of the new perimetry method. Minor differences between the results of the two analyses could be explained by the smaller sample size using a single-eye analysis. The prototype instrument used in this study was constructed for proof of concept and uses only a single central stimulus. Thus, some minimal cooperation on the part of the participants was still needed for fixation on targets. In some cases, the need for a patient to fixate on a location correlating with a scotoma could explain a reduced correspondence between the pupillometry-based perimetry and the Goldmann perimetry findings. For example, in the cone-rod dystrophy patient, who had difficulty fixating at central locations because of a central scotoma, we found relatively less correspondence between the Goldmann and the pupillometry-based test results, specifically in more peripheral locations. We believe that this reduced correspondence may be due to the central location of the stimulus and the limited ability of this patient to fixate on peripheral VF locations using parafoveal fixation. This can be overcome by asking participants to look forward, and stimuli will be individually introduced at different VF locations. A second limitation of the current study was the use of the short-wavelength stimulus at 40 cd/m$^2$. Based on the findings of Kardon et al, this light intensity can exert a pupillary response both in rods and in mRGCs. However, since transient PR was recorded, the contribution of rods probably exceeded that of mRGCs.

Furthermore, the pathology of RP patients is caused primarily by degeneration of the photoreceptors, and the defect in mRGCs is less significant, suggesting that the difference in PR to the short-wavelength stimulus between the RP patients and the normal participants was largely due to rod degeneration. In an attempt to discriminate between responses of mRGCs and the rods, the PR to short-wavelength stimuli cam be tested at different intensities to establish a protocol for differential cell-type contribution to PR, enabling a chromatic pupillometer to determine the functionality of inner and outer retinal cells at different locations in the retina.

Example 5—Retinal Dystrophy and Glaucoma Patients

The system and method described in FIGS. 1-3 was tested on subjects with diagnosed Retinal Dystrophy and subjects with Glaucoma.

Evaluation of visual field (VF) defects is important for clinical diagnosis and monitoring of various ophthalmological diseases. VF is conventionally assessed mainly by subjective perimetry techniques, including standard automated perimetry and shortwavelength automated perimetry. Two insurmountable limitations of these methods are the need for patient cooperation and the subjectivity of patients' responses. Therefore, testing of young children, the elderly, and individuals with compromised communication is almost certain to yield unreliable results. Moreover, patients' responses can be affected by their levels of fatigue, wakefulness, and attentiveness during the long procedure. Hence, constant monitoring and instruction of participants by suitably qualified personnel are needed in order to obtain reliable results. Furthermore, test-retest variability, in particular in peripheral locations and in regions of VF deficits, makes it difficult to determine whether the VF is worsening over the course of serial examinations. Frequent examinations are needed and misdiagnosis of early stages is common. Unfortunately, in routine clinical practice the frequency of VF examinations varies considerably, further emphasizing the need for new technological advances that allow earlier and objective detection of VF defects and their progression with higher levels of certainty than are currently available.

The pupillary light reflex (PLR) is an objective indicator of retinal and optic nerve functions. Several studies used a pupillometer with achromatic stimulus for objective determination of visual field. However, a comparison between visual and papillary sensitivity revealed that they are not well enough correlated to be of clinical use. Using full-field stimuli, the group of Prof. Kardon developed a protocol for assessing the contribution of rods, cones and melanopsin ganglion cells to the pupillary response (PR). These studies provided evidence that the PR to different wavelengths, stimulus intensities and stimulus durations reflects activation of different. It was suggested that the transient PR to a low intensity, short-wavelength stimulus reflects rod activity, that the transient PR to a long-wavelength stimulus is predominantly driven by cones, and that a sustained PR to a continuous high-intensity short-wavelength stimulus is derived primarily from the direct intrinsic activation of melanopsin-containing retinal ganglion cells (mRGCs). These and similar protocols were successfully used to assess the function of outer and inner retinal cells in patients with retinitis pigmentosa (RP) and patients with RPE65 mutations. However, because these methods employ a wide light source that stimulates the entire retina, they are not applicable for multifocal testing to identify VF defects.

We developed a novel perimetry based on measuring the PR to chromatic stimuli in a multifocal pattern by using a narrow (64 mm$^2$) light beam at different wavelengths. The PR's were recorded using a modified system (dark adaptometer, Roland Consult Stasche & Finger GmbH, Germany) that automatically recorded at various VF locations.

Here we present the use of the chromatic pupillometer for evaluating VF in retinitis pigmentosa and glaucoma patients.

The RP study included 20 eyes of 12 normal healthy age-matched (P=0.067 compared with patients) volunteers (6 males, 6 females; mean±SD age: 38±14.4 years; range: 25-65 years) and 30 eyes of 16 patients with RP (8 males and 9 females; mean±SD age: 48.8±15.5 years; range: 27-72 years). The glaucoma study included 22 eyes of 14 patients (8 males, 6 females, mean±SD age: 69.5±11.6; range 50-77) and 38 eyes of 22 aged-matched (p=0.64 compared with patients) healthy participants (8 males, 14 females, mean±SD age: 47±7.07; range 47-85). Inclusion criteria for healthy participants were normal eye examination, best-corrected visual acuity (BCVA) of 20/20, normal color vision test (Roth-28-hue test), no history of past or present ocular disease, no use of any topical or systemic medications that could adversely influence efferent pupil movements, and normal 24-2 Swedish Interactive Threshold Algorithm (SITA), developed for the Humphrey standard perimeter (Humphrey Field Analyser II, SITA 24-2; Carl Zeiss Meditec, Inc., Jena, Germany). Inclusion criteria for RP patients were typical abnormal fundus appearance and a previously recorded ERG that was abnormal under scotopic or photopic conditions or both (in compliance with the protocol of the International Society for Clinical Electrophysiology of Vision, which specifies the absence or diminution of b-wave amplitude below the fifth percentile with prolonged implicit times compared with normal participants). Inclusion criteria for Glaucoma patients were optic disc abnormalities and visual filed loss consistent with glaucomatous damage at least in one eye. Exclusion criteria were a concurrent ocular disease and any other condition affecting the PR. Data recorded for all patients included sex, diagnosis or genetic defect if known, and ERG responses for the RP patients.

Light stimuli were presented using a Ganzfeld dome apparatus (multifocal dark-adaptometer; Roland Consult Stasche & Finger GmbH) placed 330 mm from the patient's eye, and controlled with a stimulus generator and custom software. The untested eye was occluded. Stimuli were presented from the center, and participants were asked to fixate on a red light emitting diode fixation light presented from 13 different locations in the VF (central, superior, inferior, temporal, and nasal fields at angles of 10°, 20°, and 30°). Wavelengths of the light stimuli selected for this study were 640±5 nm for red light (long wavelength) and 480±5 nm for blue light (short wavelength). Each stimulus was presented using stimulus size V (64 mm$^2$) on a background luminance of 2.7 cd/m$^2$. Stimulus duration was 1 sec and the inter-stimulus interval was 10 seconds.

Pupil diameters were recorded in real time by a computerized infrared pupillometer (Roland Consult Stasche & Finger GmbH), which consisted of a monitor with viewing optics for presentation of a light stimulus to the subject. Pupil tracking was performed by an infrared high-resolution camera inside the dark-adaptometer that recorded the PR at a sampling rate of 34 Hz. The software (Roland Consult Stasche & Finger GmbH) searched for the pupil in every image. A correction factor was used to get the diameter in millimeters and pupil diameters were measured with an accuracy of 0.1 mm (Roland Consult Stasche & Finger GmbH). The subject's eye was inclined at 15° to the center, at the position where the stimulus was presented. The subject had an uninterrupted VF in excess of 30° in all meridians. A recordable PR was obtained in both eyes of all patients except for two, both of whom had difficulty in fixating on most fixation locations in one eye. The subjects were requested to blink several times before the start of the recording and refrain from blinking during the recording. Real-time video imaging of the eye was carefully monitored by the examiner during the test. Tests in which the subject blinked were excluded and the subject was retested.

Percentage pupil contraction at each time point was determined by the formula: % pupil contraction=100*[The difference between the highest initial diameter at the beginning of the stimulus and the lowest diameter in response to that stimulus]/[The highest initial pupil diameter], as described by Kardon et al. All calculations were done by an independent experienced masked technician. The test duration was approximately 5 minutes for each eye.

The RP patients were tested for kinetic VF by dark-adapted chromatic Goldmann perimetry. Briefly, a Goldmann perimeter (940-ST; Haag-Streit AG, Liebefeld, Switzerland) was used to map patient's conventional and two-color dark adapted VFs. Patients were dark adapted for 30 minutes prior to testing. The setting used for stimuli were V3c for the long-wavelength stimulus and 2 log units lower in luminance (V3c) for the short-wavelength stimulus.

Statistical analysis was performed using a commercial software program (SAS for Windows, version 9.2; SAS Institute, Inc., Cary, N.C.; or SPSS for Windows, version 20.0; SPSS, Inc., Chicago, Ill.). For two-eye analysis, comparison between patients and healthy controls for all perimetry locations was performed using a one-way ANOVA with repeated measures (eye side). Since for some of the participants only one eye was examined, the mixed model was applied to address this issue. For single-eye analysis, we compared between the pupillary recordings of the right eye of patients and healthy controls for all perimetry locations using a one-way ANOVA. Agreement between the chromatic pupillometer recordings and the dark-adapted chromatic Goldmann (that yields a yes/no result) was assessed using two-sample t-test and the Mann-Whitney nonparametric test. Correlation between the chromatic pupillometer recordings and Humphrey VF was assessed by Pearson Chi Square Test. A value of P<0.05 was considered statistically significant.

Figure 18:
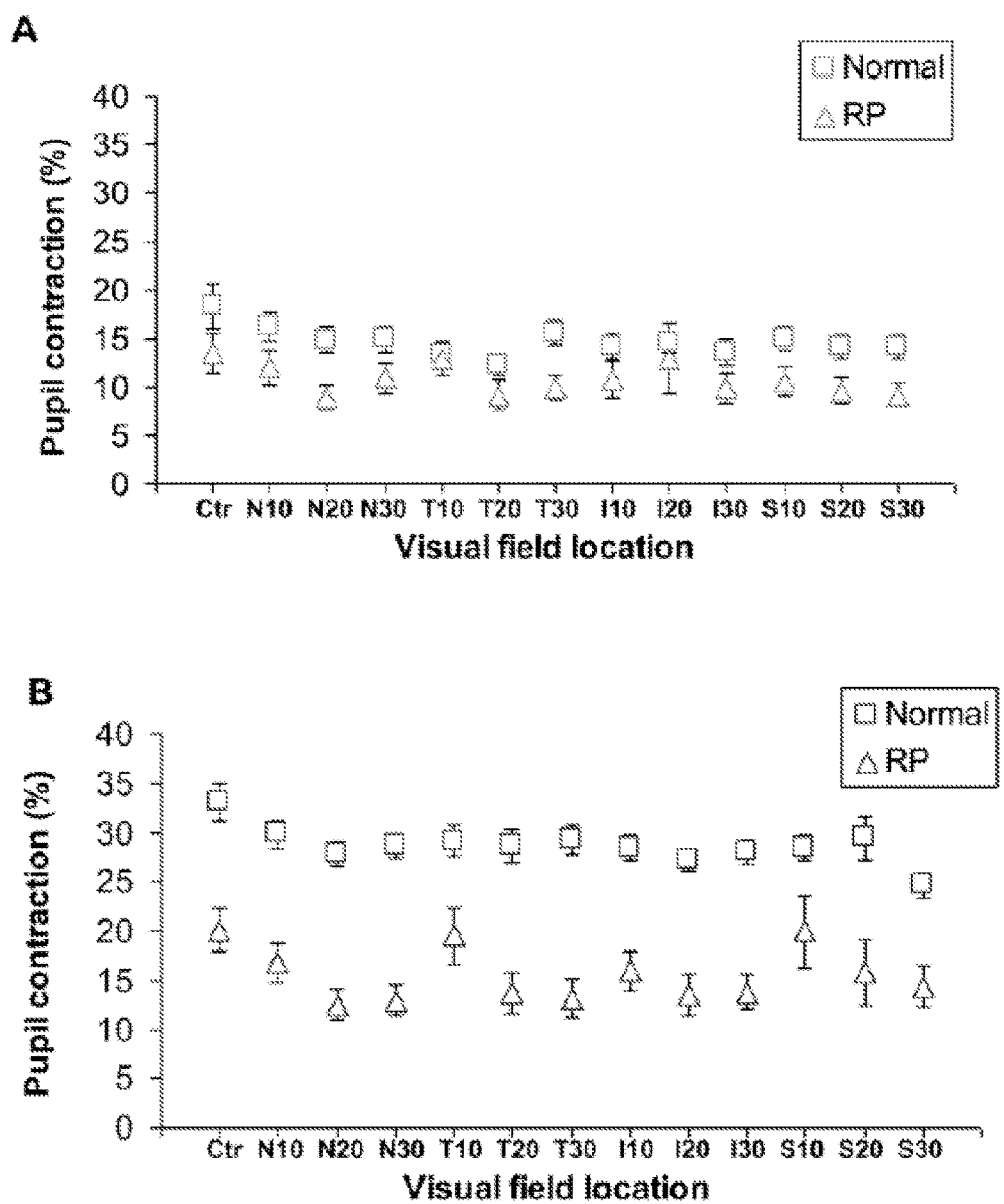
FIG. 18 shows percentage change in pupil diameter in both eyes of RP patients and normal participants in response to long-wavelength (A) and short-wavelength stimuli (B).

RP patients have significantly reduced pupillary responses to short-wavelength stimulus in nearly all perimetric locations RP patients demonstrated a significantly lower mean PR to the short-wavelength stimulus at 40 cd/m² compared with control participants in all perimetry locations (P<0.03), except temporal 10°. The lowest PR of RP patients were consistently recorded in peripheral locations (20° and) 30°. By contrast, in response to the long-wavelength stimulus at 40 cd/m², RP patients demonstrated significantly reduced PR mostly in peripheral locations (P≤0.02, FIG. 18). Pearson correlation analysis revealed a significant agreement between the chromatic pupillometer recordings and chromatic Goldmann in RP patients in most locations in response to the short wave length stimulus (p<0.05, FIG. 19). The correlation between the two perimetry techniques was lower in the response to the long wave length stimulus. In all patients tested, minimal pupillary responses were recorded in areas that were non-detected in the dark-adapted chromatic Goldmann. A representative RP patient is demonstrated in FIGS. 20A and 20B. This was a 68-year-old white male with isolated RP.

Figure 20A:
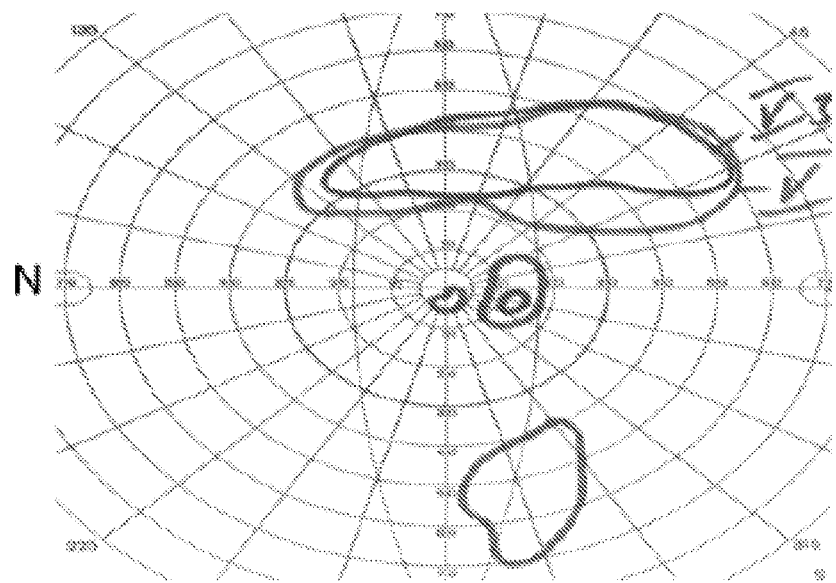
FIG. 20A shows a chromatic dark-adapted Goldmann perimetry of the right eye.
Figure 20B:
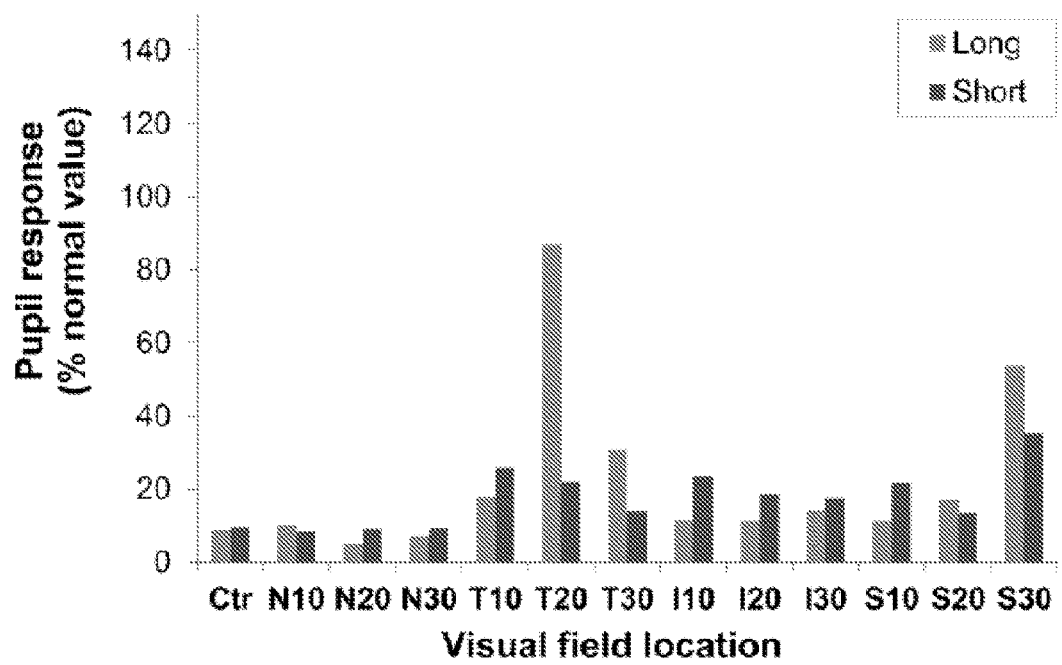
FIG. 20B shows a comparison of PR of the patient's right eye in response to both short- and long-wavelength stimuli, as a percentage of mean normal values.

Fundus examination demonstrated pigment epithelial atrophy, arteriolar narrowing, and bone spicules and clumps in the midperiphery of both eyes. BCVA was 20/30 in both eyes and significant ERG and VF loss were demonstrated (data not shown and FIG. 20A). In most of the VF locations the PR of this patient to both long- and short wavelength stimuli was lower by over 3-fold compared with the mean PR of the right eye in the healthy participant group (FIG. 20B). In most of the tested perimetry locations there was an agreement between the pupillometer-based perimetry and the chromatic Goldmann perimetry. Thus, the PR to the long-wavelength stimulus was highest at temporal 20° and superior 30° (FIG. 20B). These locations correspond to the areas where the long-wavelength stimulus was detectable in the chromatic Goldmann perimetry (FIG. 20A). In areas where the long-wavelength stimulus was not detected in the chromatic Goldmann (10° superior, and all inferior and nasal locations), the PR response was lower than 15% of mean normal values. The highest pupillary responses to the short-wavelength stimulus were recorded at 30° superior and at 10° and 20° temporal, in agreement with the areas where the short-wavelength stimulus was detected in chromatic Goldmann perimetry (FIGS. 20A and 20B). The lowest PR to the short-wavelength stimulus (<10% of normal mean values) was obtained in locations that were not detected in the chromatic Goldmann (center and all nasal locations).

Lower correspondence was observed in areas that were on the isopters of the chromatic Goldmann VF (temporal 10° in the long-wavelength and superior 20° for both wavelength stimuli).

Glaucoma patients have significantly reduced pupillary responses to short- and long-wavelength high intensity stimulus in nearly all perimetric locations.

Figure 21:
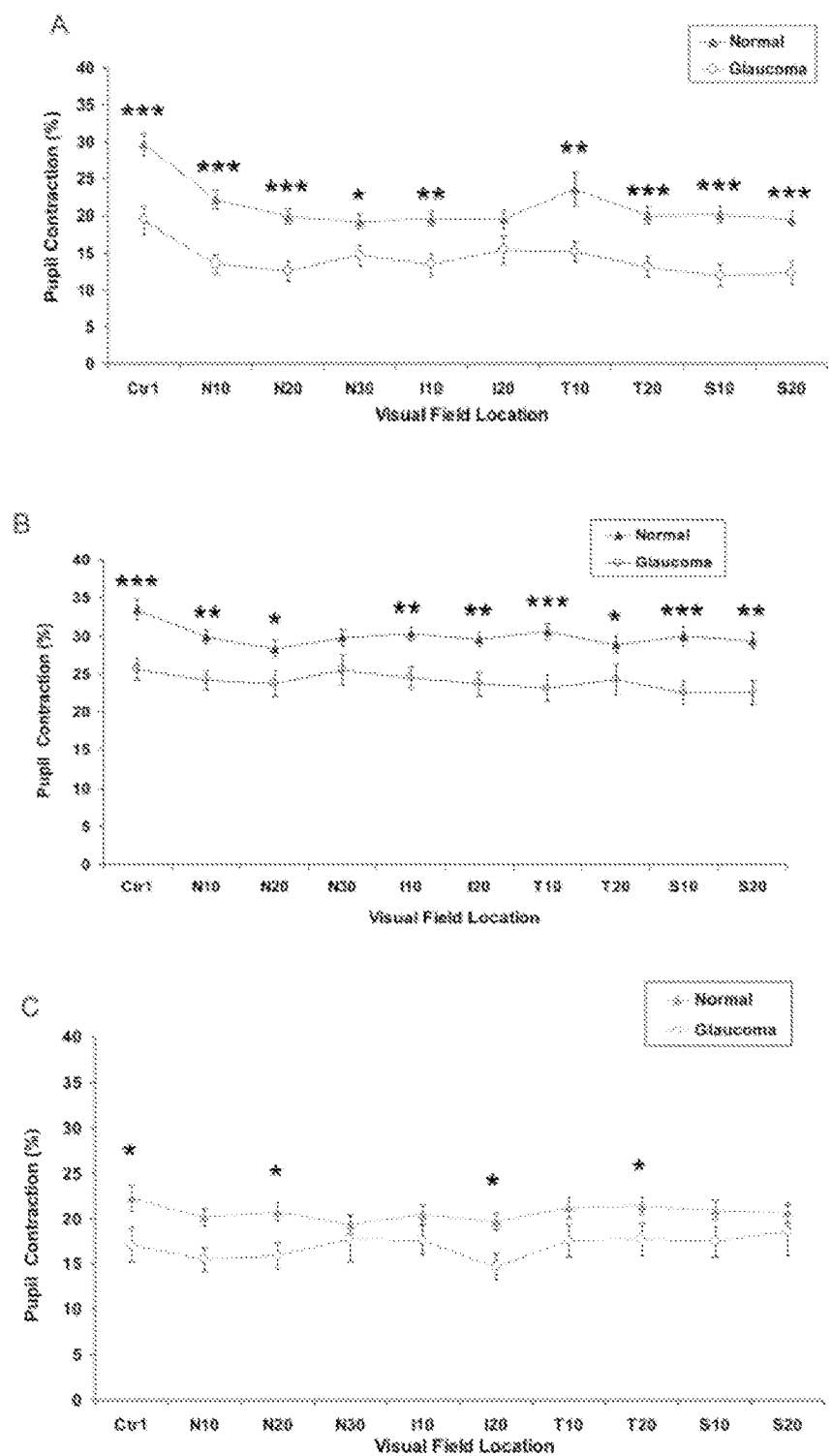
FIG. 21A shows percentage change in pupil diameter in both eyes of glaucoma patients and healthy participants in response to long-wavelength at 100 cd/m2 (A); short-wavelength stimuli at 100 cd/m$^2$ (B); and short-wavelength stimuli at 40 cd/m$^2$ (C).

Next we evaluated the visual field defects in patients with glaucoma using the prototype chromatic pupillometer. Thirty-eight eyes of 22 healthy individuals and 22 eyes of 14 glaucoma patients were tested. The PR was measured in 11 locations for the short-wavelength stimulus at two light intensities (40 cd/m² and 100 cd/m²) and red stimulus at 100 cd/m². Significantly reduced pupillary responses were recorded in glaucoma patients in response to high intensity short and long-wavelength stimuli in nearly all perimetric locations (P<0.05, FIGS. 21A and 21B). By contrast, in response to the short-wavelength stimulus at 40 cd/m², glaucoma patients demonstrated significantly reduced PR only in locations that correlate with glaucoma pathology (central and 20°, FIG. 3C). In a majority of locations the chromatic pupillometer recordings of PR to the different stimulus were in agreement with the Humphrey-based perimetry (FIG. 22).

Our studies demonstrate the feasibility of using pupillometer-based chromatic perimetry for objectively assessing visual field defects in patients with glaucoma and retinal dystrophies. The chromatic pupillometer prototype successfully detected optic neuropathy in glaucoma and defects in outer retina cells (rods and cones) with high sensitivity.

The RP patients exhibited significantly reduced mean PR to the short-wavelength stimulus at most locations, whereas their mean responses to the long-wavelength stimulus were similar to those of normal participants at central locations but were significantly reduced at peripheral locations. Studies from the groups of Kardon and Stieger demonstrated that transient PR to a low-intensity, short-wavelength stimulus reflects rod activity and that transient PR to a long-wavelength stimulus is predominantly driven by cones. In retinitis pigmentosa patients, the loss of rod function exceeds the reduction of cone function and VF loss typically begins with peripheral VF constriction. These findings suggest that the PR to short-wavelength stimulus at low intensity measured by our chromatic pupillometer may be mediated by rods, whereas the PR to long-wavelength stimulus measured here may be mediated by cones. A clinically applicable protocol can be developed for assessing these cell contributions to the PR measured by our chromatic pupillometer. This will enable both the objective detection of affected areas and the identification of the damaged photoreceptor cells underlying the defect in these locations.

The glaucoma patients exhibited significantly reduced mean PR to high-intensity (100 cd/m²) short- and long-wavelength stimulus at most locations, whereas their PR to lower-intensity (40 cd/m²) short-wavelength stimulus was significantly reduced in locations that correlate with glaucoma pathology. These findings suggest that using low intensity short wavelength stimulus may show isolated areas of defect. However, high intensity stimuli showed larger area of defect.

One possible implication of these findings could be that higher intensity light stimuli enables the early detection of glaucoma defects.

To validate the new chromatic perimetry technique we compared the novel pupillometer method with two established perimetry technique: Goldmann's and Humphrey's. We chose the chromatic dark adapted Goldmann's for the RP study because it uses multifocal chromatic short and long-wavelength stimuli for perimetry determination and monitoring of patients with retinal dystrophies. We observed a good agreement between the chromatic pupillometer-based perimetry and the malfunctioning areas identified by the two conventional perimetry techniques. Furthermore, a correlation was observed between the pupillometer and the two methods in a majority of locations in response to the short-wavelength stimulus. Our findings that the PR did not correlate in all areas with the Goldmann and Humphrey, could be explained by the differences between the pupillometer and these two subjective methods: the Goldmann and Humphrey are threshold-subjective tests. By contrast the chromatic pupillometer is a suprathreshold, objective quantitative test. Hence, it is likely that the pupillometer can detect reduced retinal response to suprathreshold stimuli.

Since the response to the long-wavelength stimulus was less affected in RP patients, a lower agreement with the Goldmann test was observed. In some cases the lower agreement could be explained by PR measurements in areas corresponding to VF isopters.

The results presented here are highly promising for use of the multifocal chromatic PR as an objective parameter of retinal and optic nerve function in disease conditions.

The prototype instrument used in this study was constructed for proof of concept and uses only a single central stimulus. Thus, some minimal cooperation on the part of the participants was still needed for fixation on targets. In some cases, the need for a patient to fixate on a location correlating with a scotoma could explain a reduced correspondence between the pupillometry-based perimetry and the Goldmann perimetry findings. This limitation may be overcome by asking participants to look forward, and stimuli will be individually introduced at different VF locations. This novel chromatic pupillometer may enable sensitive and objective characterization of VF defects and may be used to diagnose and monitor patients with optic nerve damage and photoreceptor dystrophies.

Example 6—Red Vs. Blue Stimulus—Central Points

Figure 23:
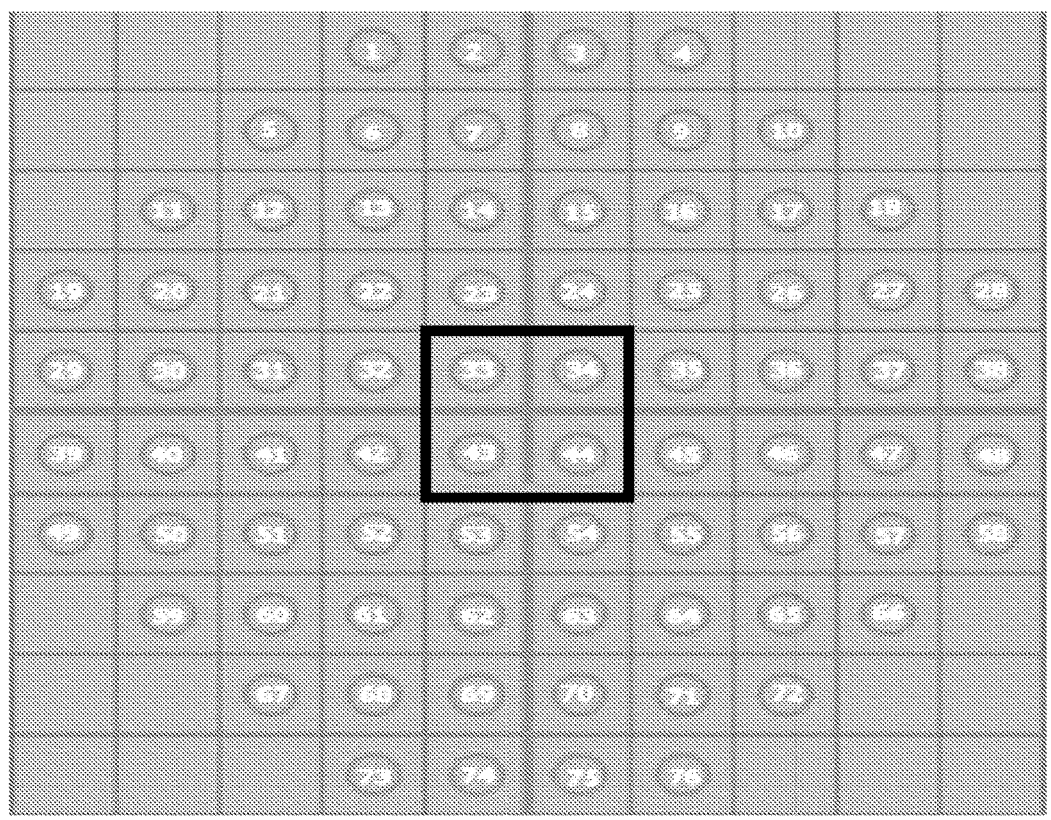
FIG. 23 shows a 76-point visual field (18°) used for testing, with the four central targets highlighted.

The system and method described in FIGS. 1-3 was tested on subjects having healthy eyes. Eighteen eyes of healthy volunteers (aged 26-68, AVG±SD 37.6±15.9), including 8 females and 10 males, were tested. Inclusion criteria were (i) healthy eyes, (ii) no ophthalmic disorders, and (iii) no use of topical or systemic medications that could affect pupil contraction. Pupil responses to short and long wavelengths at increasing light intensities were tested at 4 central targets of a 76-point visual field (FIG. 23).

Figure 24A:
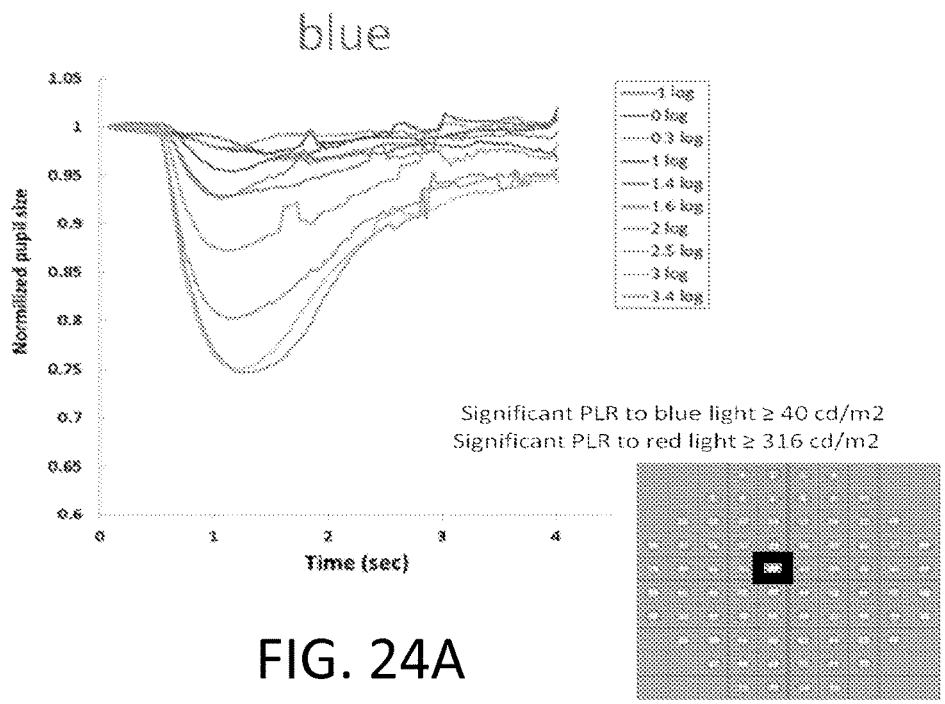
FIG. 24A shows normalized pupil size over time, for blue stimulus, in red vs. blue stimulus testing using central targets.
Figure 24B:
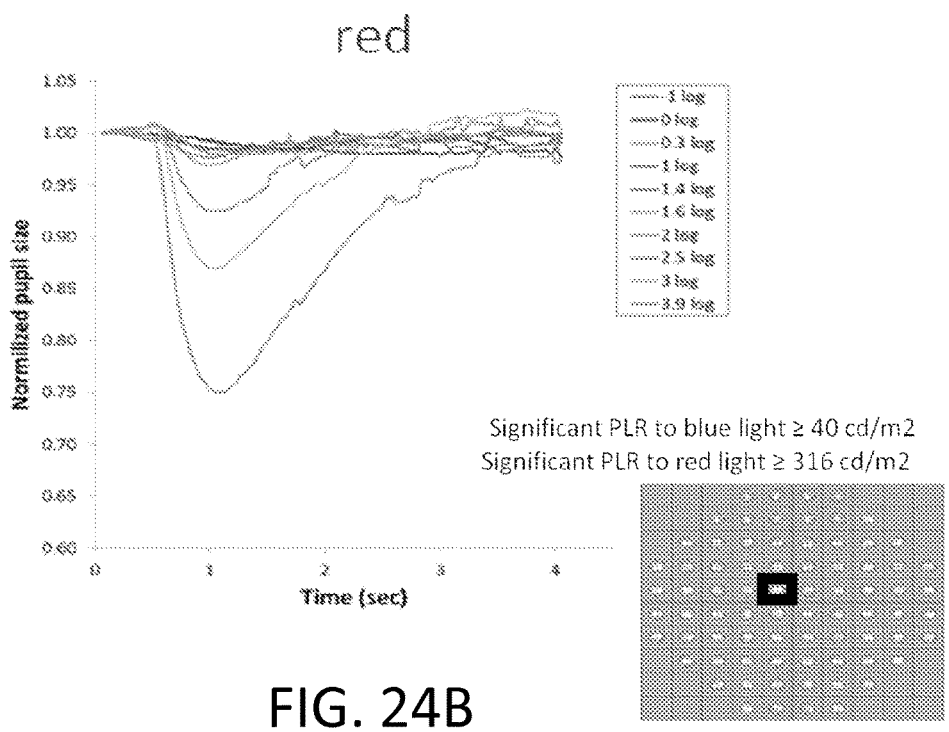
FIG. 24B shows normalized pupil size over time, for red stimulus, in red vs. blue stimulus testing using central targets.
Figure 25A:
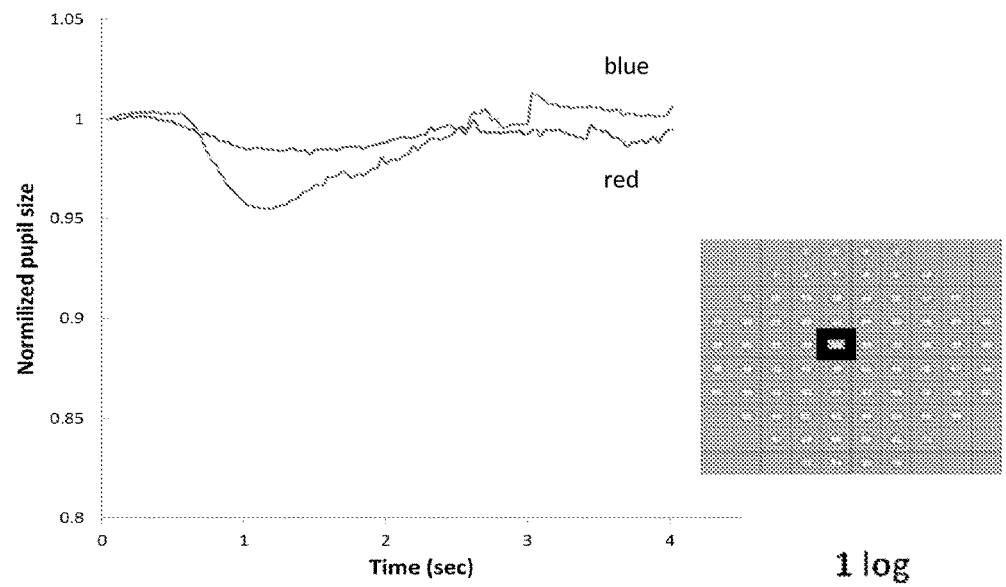
FIG. 25A shows normalized pupil size over time, for blue stimulus, in red vs. blue stimulus testing using central targets.
Figure 25B:
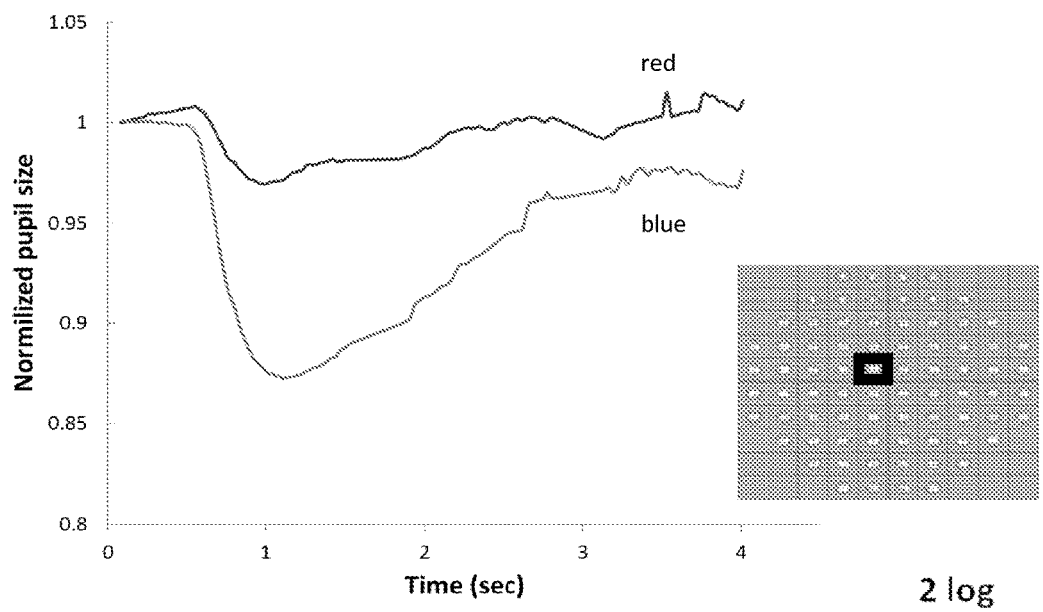
FIG. 25B shows normalized pupil size over time, for red stimulus, in red vs. blue stimulus testing using central targets.
Figure 25C:
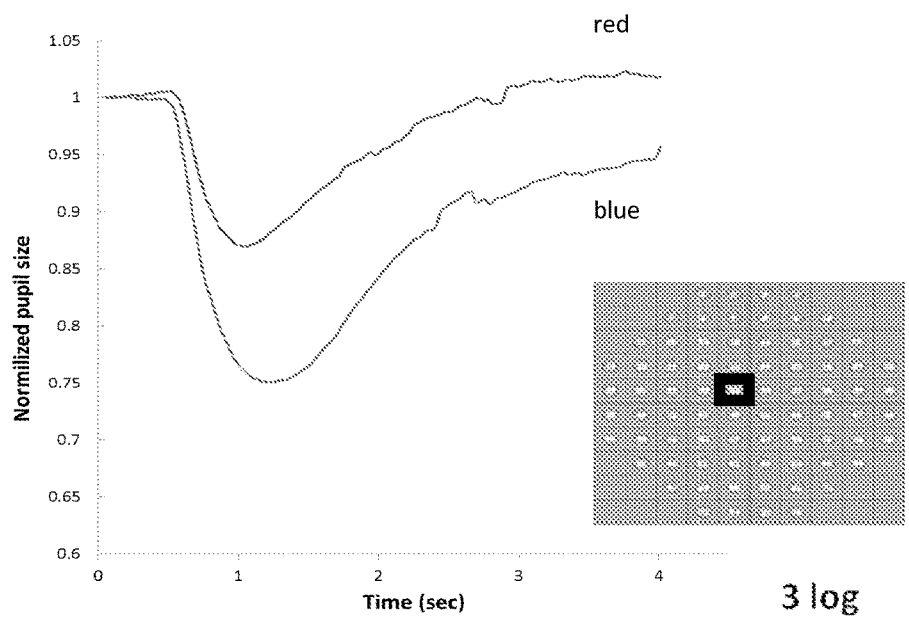
FIG. 25C shows normalized pupil size over time, for blue stimulus, in red vs. blue stimulus testing using central targets.
Figure 25D:
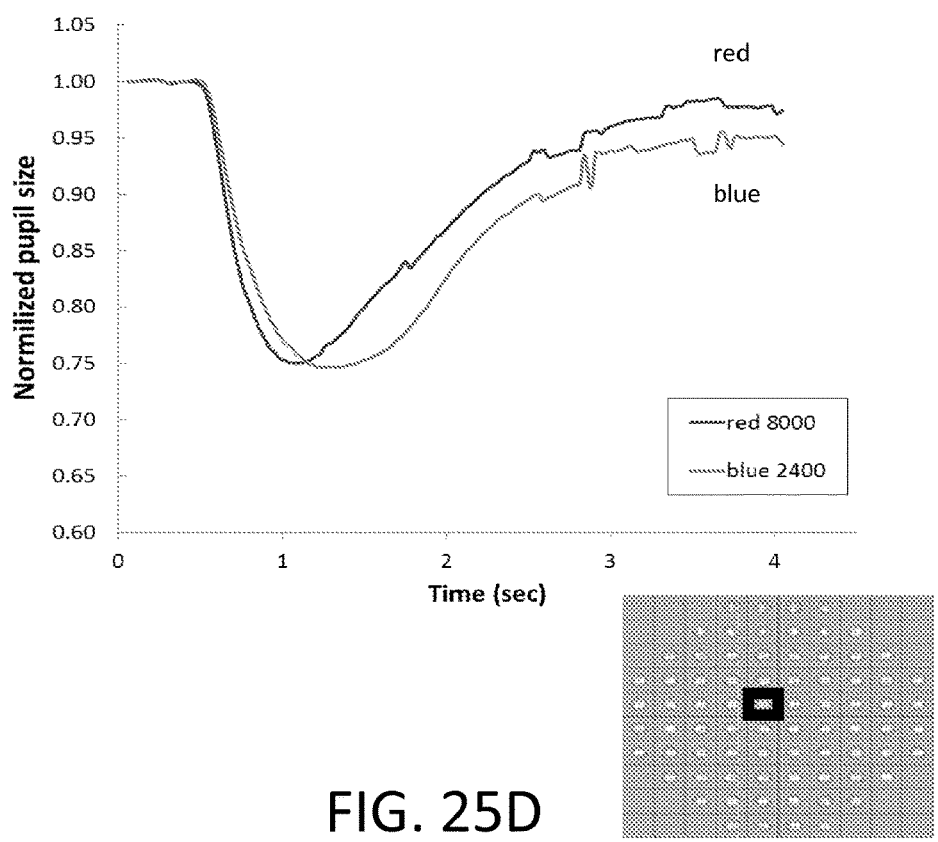
FIG. 25D shows normalized pupil size over time, for red and blue stimulus, in red vs. blue stimulus testing using central targets.
Figure 26A:
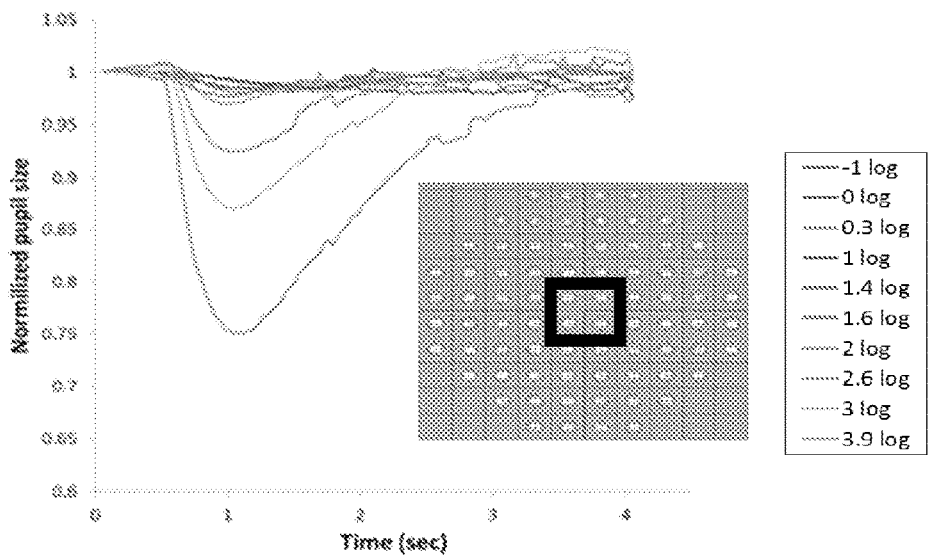
FIGS. 26A-26D show normalized pupil size over time, for red stimulus at four central points, in red vs. blue stimulus testing using central targets.
Figure 26B:
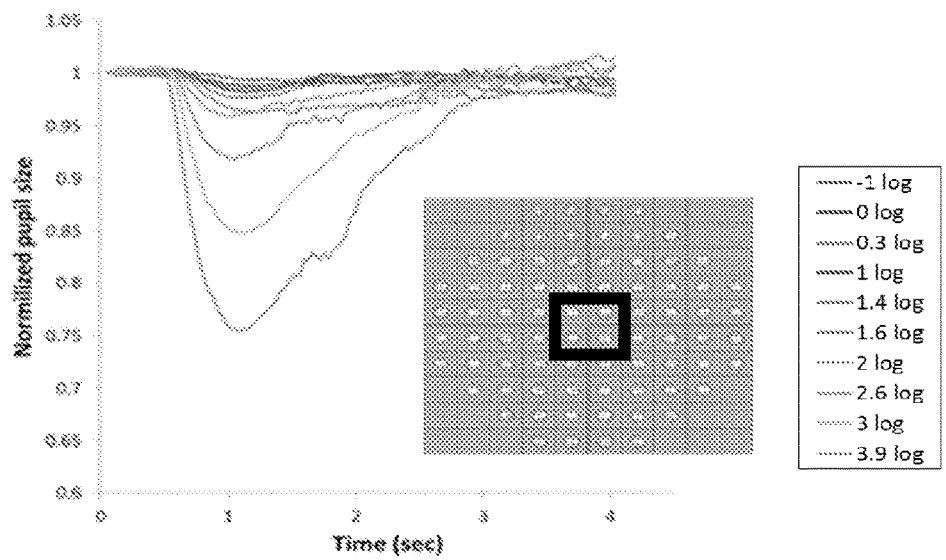
Figure 26C:
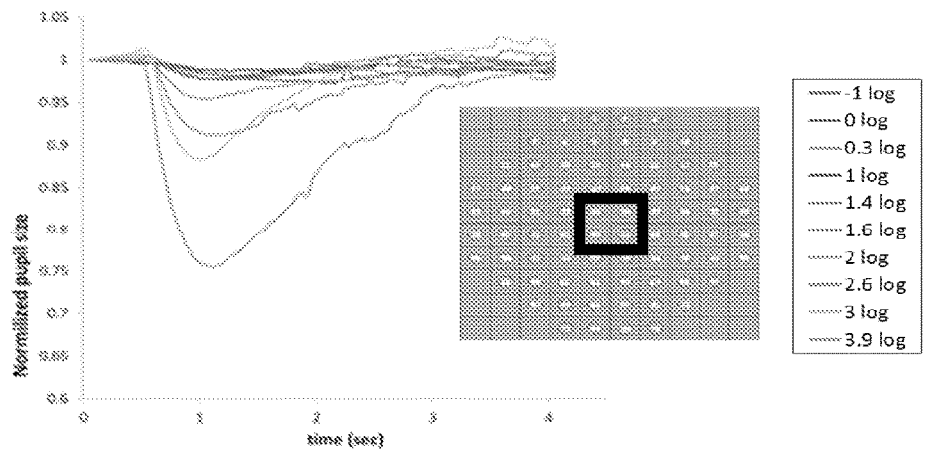
Figure 26D:
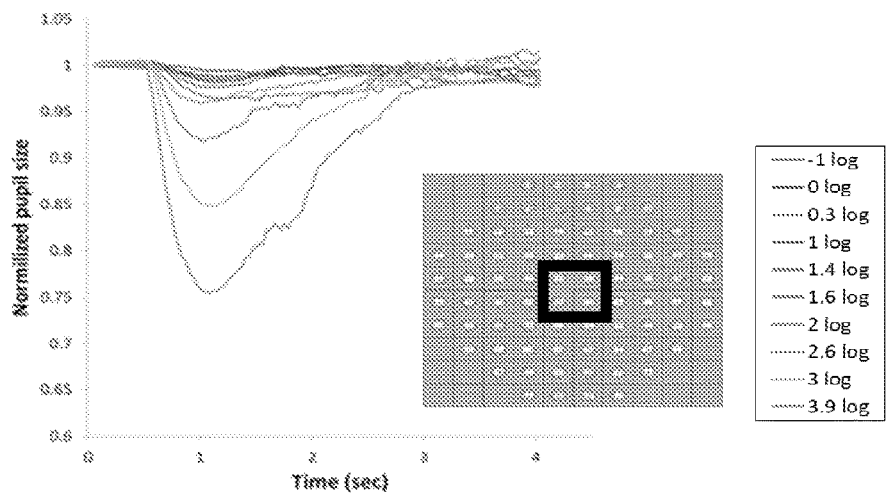
Figure 27A:
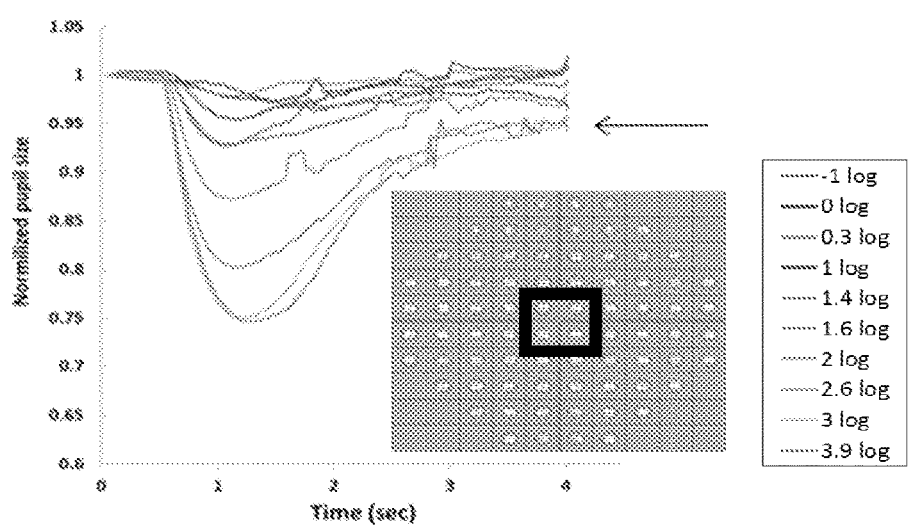
FIGS. 27A-27D show normalized pupil size over time, for blue stimulus at four central points, in red vs. blue stimulus testing using central targets.
Figure 27B:
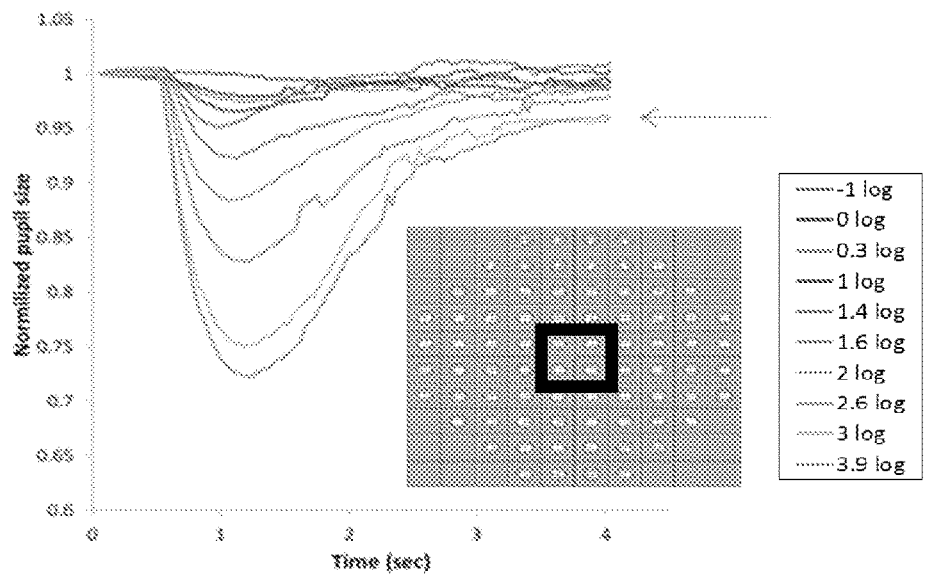
Figure 27C:
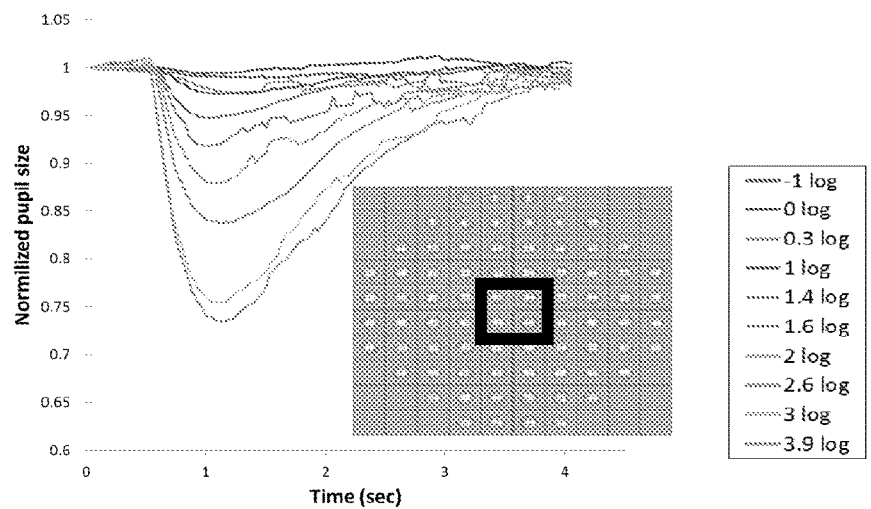
Figure 27D:
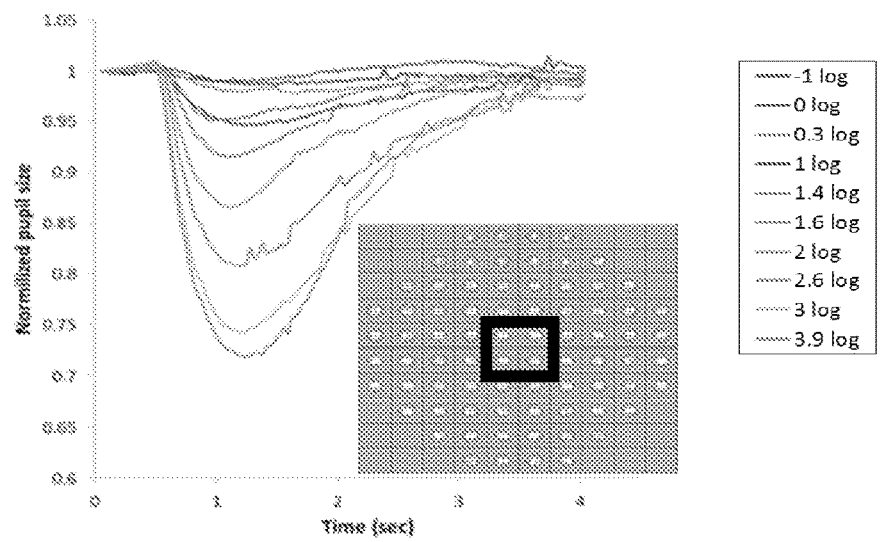

As shown in FIGS. 24A and 24B, the results indicate that the PLR to long wavelength stimulus is smaller and the pupil recovers faster compared to the short wavelength stimulus.

FIGS. 25A, 25B, 25C, and 25D show results indicating the PLR to red stimulus is smaller and has a faster recovery compared to the blue stimulus.

FIGS. 26A-26D show normalized pupil size over time, for red stimulus at four central points, and FIGS. 27A-27D show normalized pupil size over time, for blue stimulus at four central points.

The conditions for substantial pupillary responses to red and blue light from small targets (2 mm) have been established through this test. The PLR to red stimulus is smaller and has a faster recovery compared to the blue stimulus. Additionally, the sustained response to strong (>1000 $cd/m^2$) blue stimulus in upper central targets suggests a possible involvement of the ipRGC pathway.

Example 7—Red vs. Blue Stimulus—Full Field

The system and method described in FIGS. 1-3 was tested on the right eyes of seventeen healthy volunteers (aged 26-77). Pupil responses to short and long wavelengths at increasing light intensities were tested using a full 76-point visual field.

In the test, each subject's non-tested eye was covered by a patch. After a 5-minute dark adaptation, a stimulus having a 1-second duration was provided. The pupil size was tracked for four seconds. The chromatic stimuli used were: Red (1000 $cd/m^2$, 640 nm), and Blue (200 $cd/m^2$, 482 nm).

Figure 28:
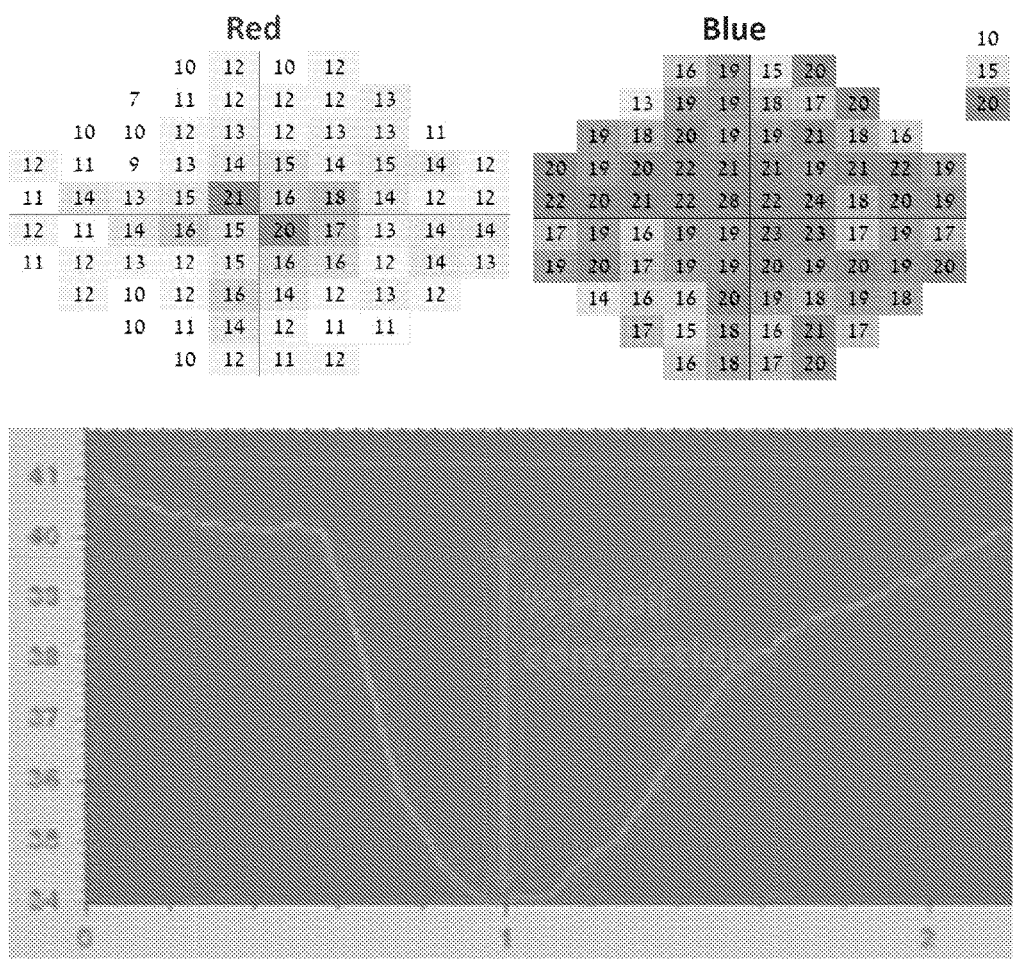
FIGS. 28 and 29 show percentage of pupil contraction for red and blue stimulus, in full-field red vs. blue stimulus testing.
Figure 29:
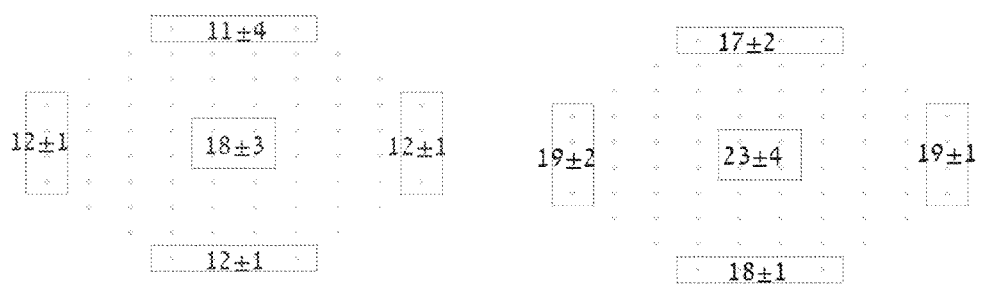
Figure 29:
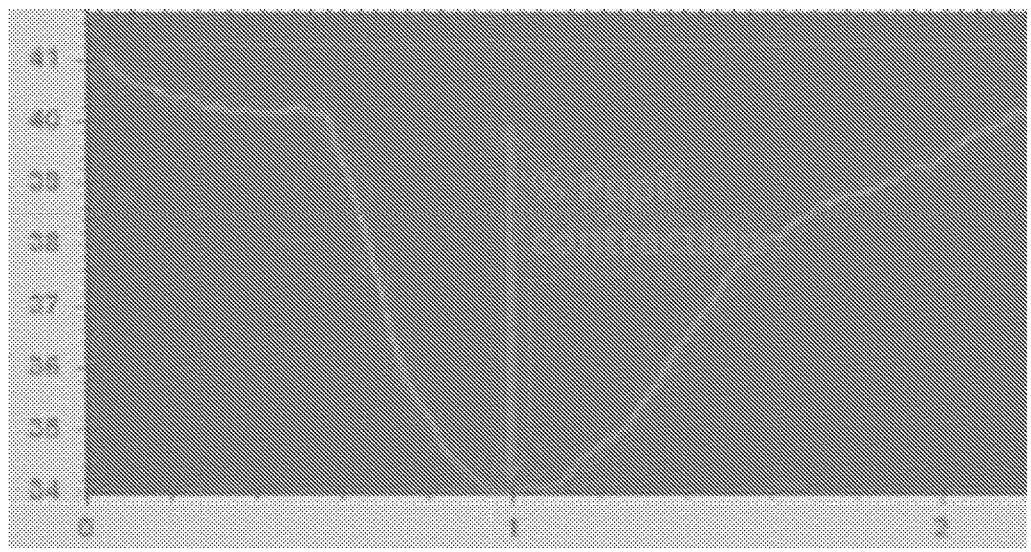
Figure 30:
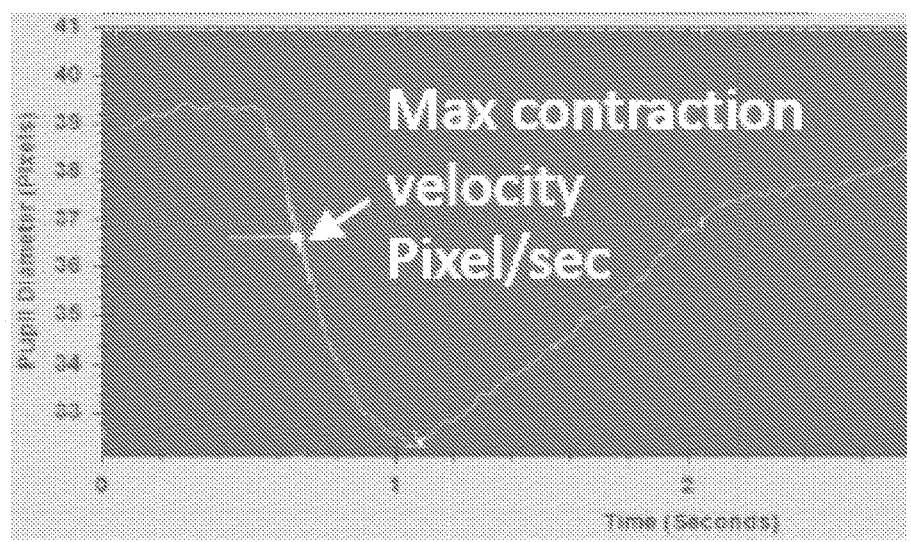
FIGS. 30 and 31 show maximal contraction velocity for red and blue stimulus, in full-field red vs. blue stimulus testing.
Figure 31:
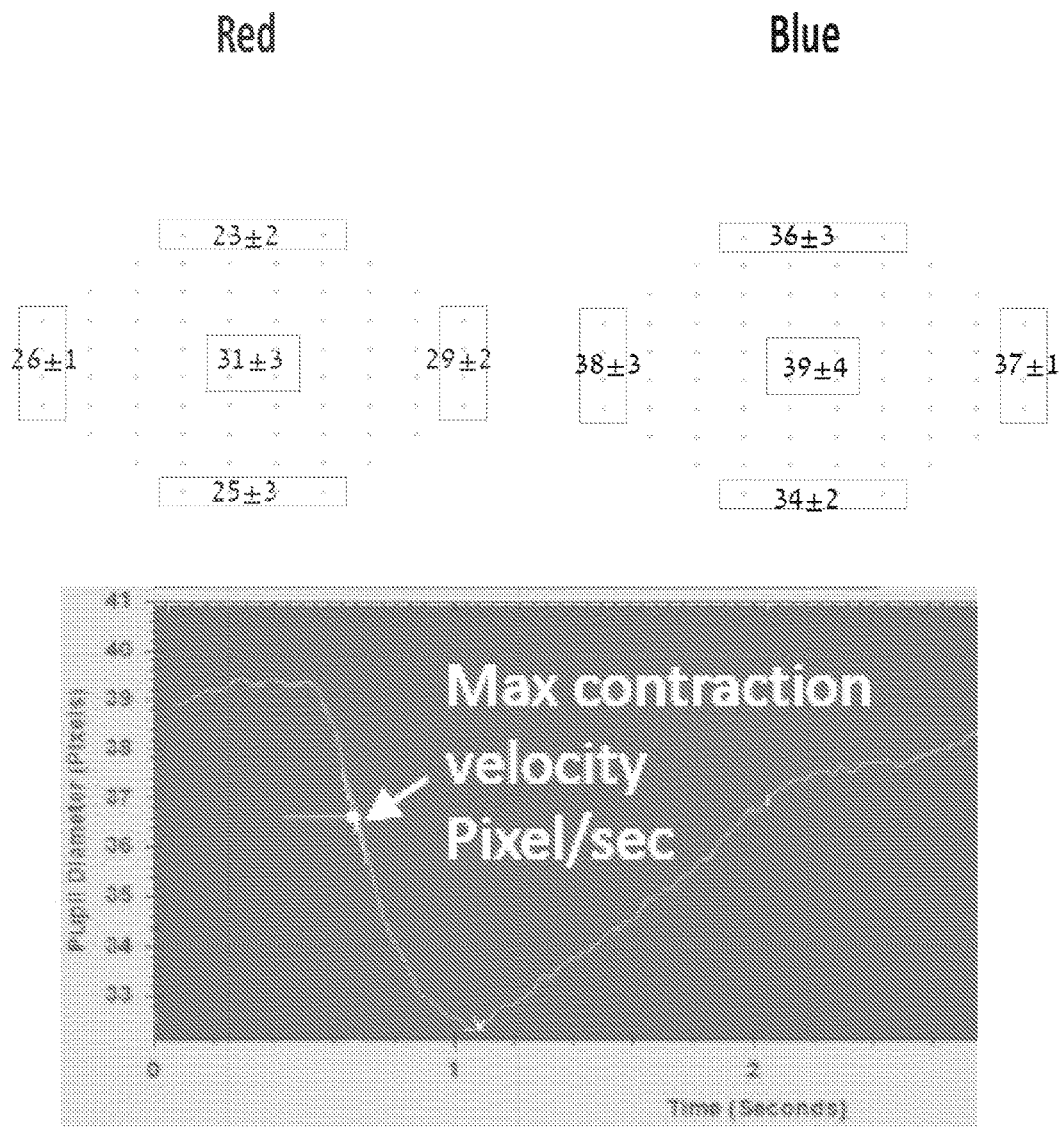
Figure 32:
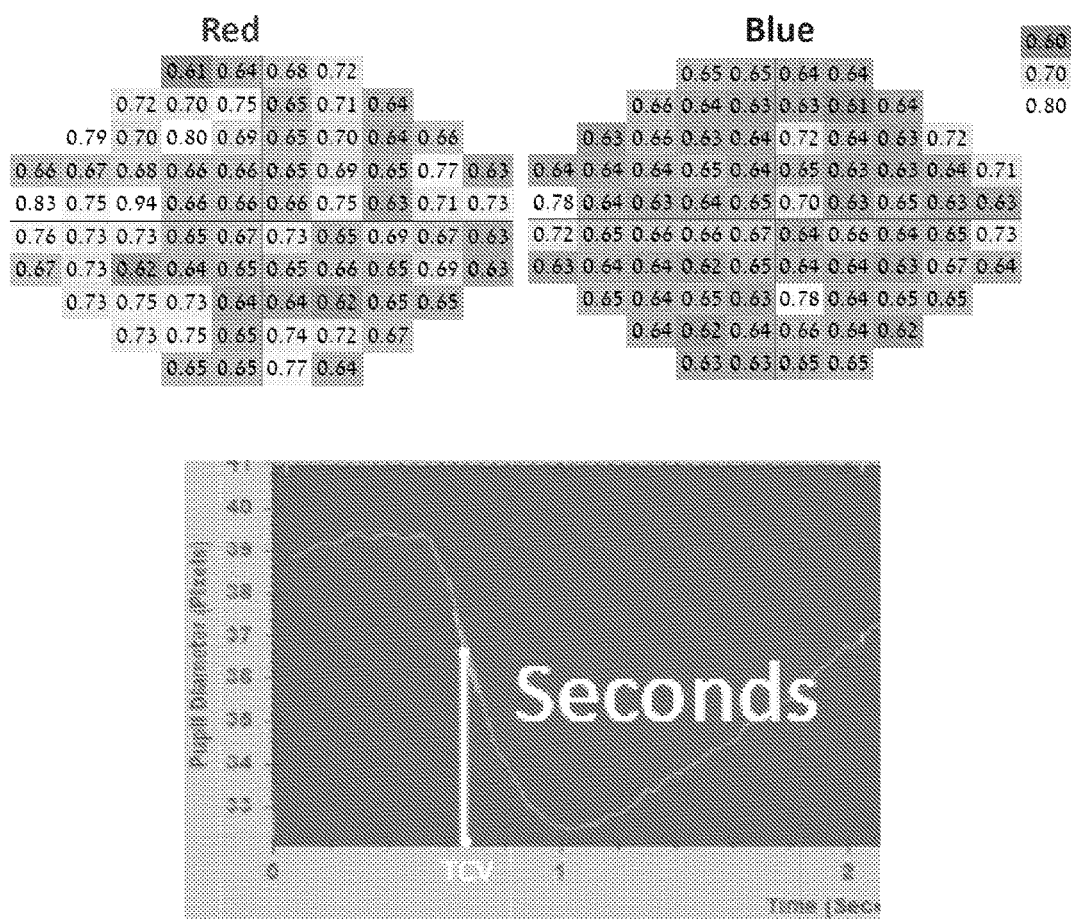
FIGS. 32 and 33 show the time of maximal contraction velocity for red and blue stimulus, in full-field red vs. blue stimulus testing.
Figure 33:
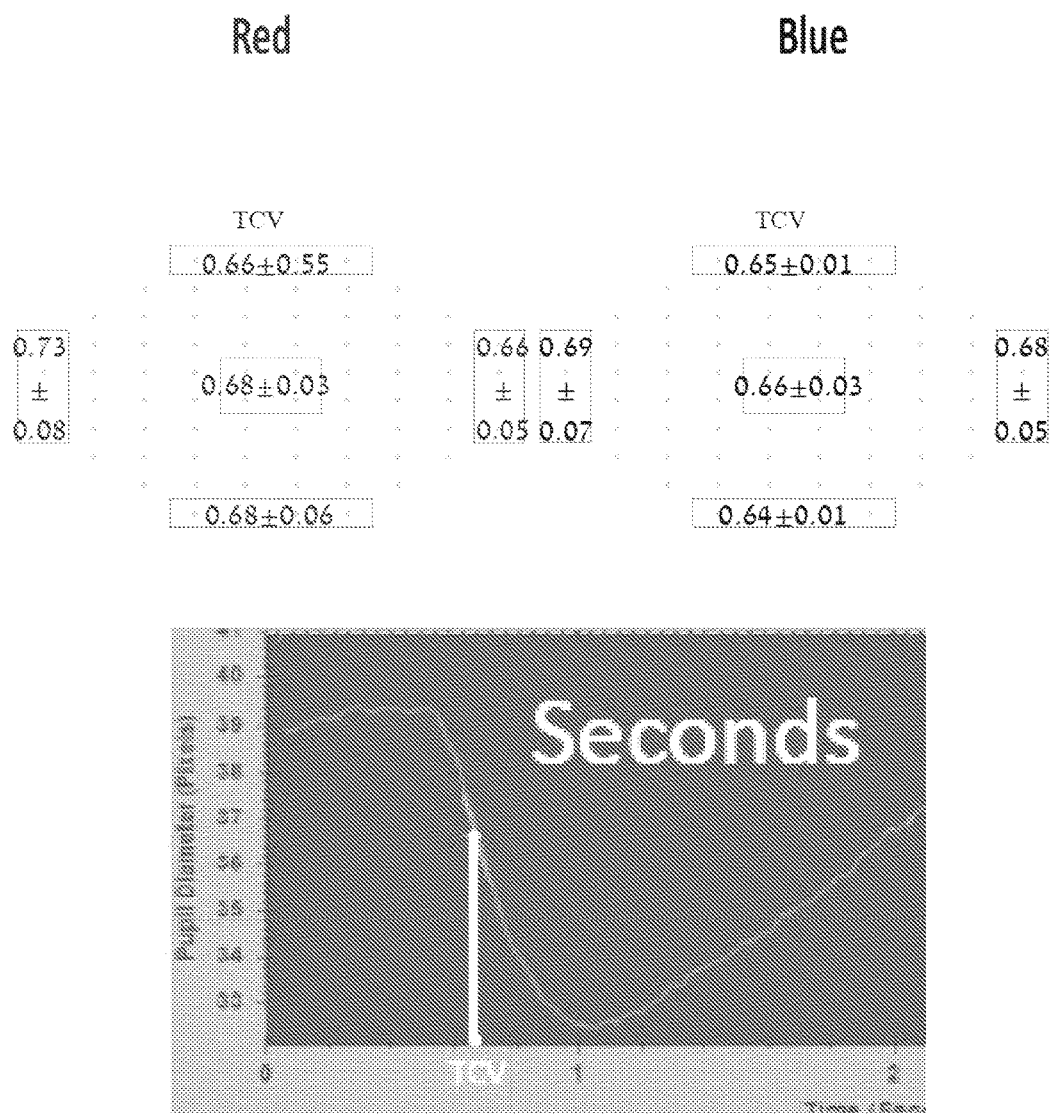

As shown in FIG. 28, a higher percentage of contraction was recorded in response to the blue stimulus, compared to the red stimulus. FIG. 29 shows that the highest pupil response was measured in the center of the visual field. FIG. 30 shows that the mean maximal contraction velocity recorded in response to the blue stimulus is higher than that in response to the red stimulus. FIG. 31 shows that the maximal contraction velocity was higher in the center than at the periphery in response to the red stimulus, and that the maximal contraction velocity was uniform in response to the blue stimulus. FIG. 32 shows that the maximal velocity is recorded on earlier time points in response to the blue stimulus, compared to the red stimulus. FIG. 33 shows that the time of maximal contraction velocity is relatively uniform throughout the visual field.

It can therefore be concluded that, for normal, healthy subjects, (i) there is a stronger pupil response to blue stimulus than to red stimulus, (ii) the percentage of pupil contraction and maximal velocity were higher, and the time of maximal contraction velocity was shorter, in the center of the visual field than in the periphery in response to both colors, and (iii) the time of maximal contraction velocity was relatively uniform in response to the blue stimulus.

Example 8—Response Consistency in Serial Testing

Figure 34A:
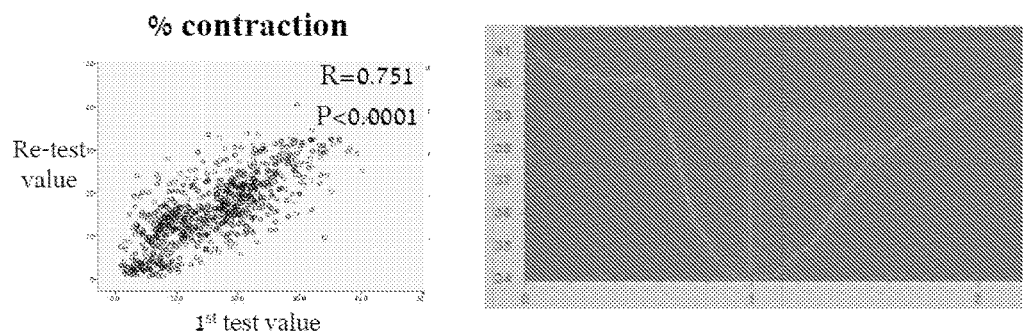
FIG. 34A shows a correlation assessment for percentage of pupil contraction, in serial testing for response consistency.
Figure 34B:
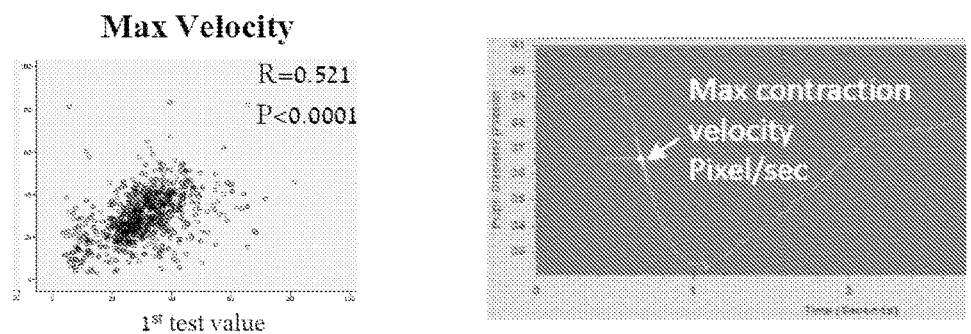
FIG. 34B shows a correlation assessment for maximal contraction velocity, in serial testing for response consistency.
Figure 34C:
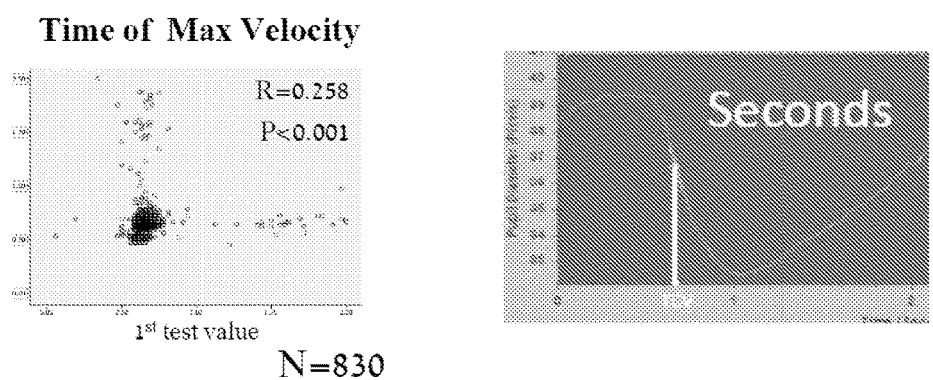
FIG. 34C shows a correlation assessment for the time of maximal contraction velocity, in serial testing for response consistency.

The system and method described in FIGS. 1-3 was tested on the eyes of eleven healthy volunteers. Pupil responses to short and long wavelengths at increasing light intensities were tested using a full 76-point visual field. Two volunteers were tested over 24 hours, seven volunteers were tested over 4 months, and two volunteers were tested over a year. Correlation was assessed using a Spirman correlation analysis. The results are shown in FIGS. 34A, 34B, and 34C.

It can be concluded from these results, from re-testing in normal, healthy subjects, that there is (i) a high correlation in repeated testing of the percentage of contraction and maximal contraction velocity in response to blue and red stimuli, and (ii) a lower but significant correlation in time of maximal contraction velocity in response to both colors.

Example 9—Retinitis Pigmentosa Patients

The system and method described in FIGS. 1-3 was tested on the eyes of eleven Retinitis Pigmentosa (RP) patients and seventeen healthy age-matched volunteers. Pupil responses to short and long wavelengths at increasing light intensities were tested using a full 76-point visual field. A comparison was made between the RP patients and the healthy controls in response to red stimuli at 1000 $cd/m^2$ and blue stimuli at 200 $cd/m^2$. The chromatic pupillometer recordings were compared with dark-adapted chromatic Goldmann results. A one-way Anova analysis was used to compare the visual field of RP and healthy subjects.

Figure 35:
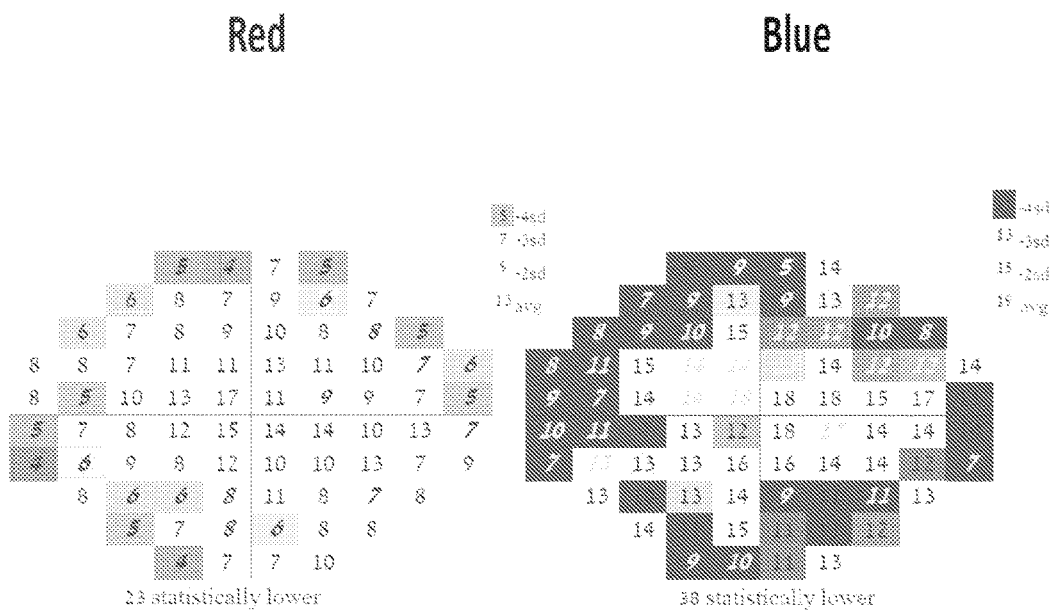
FIG. 35 shows maximal contraction velocity for red and blue stimulus, in RP testing.
Figure 35:
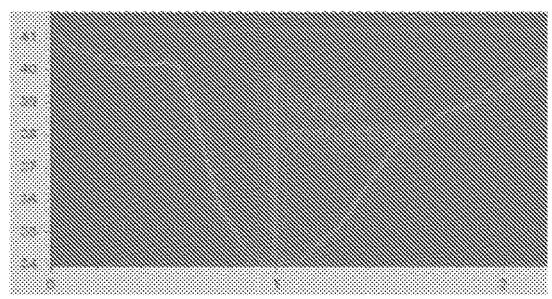
Figure 36:
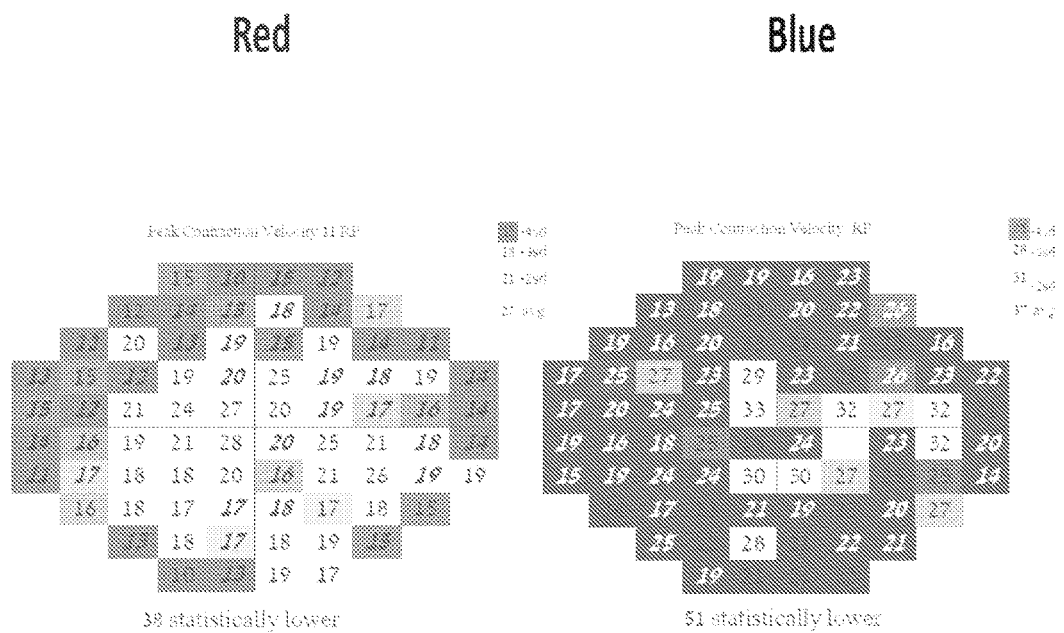
FIG. 36 shows peak contraction velocity for red and blue stimulus, in RP testing.
Figure 36:
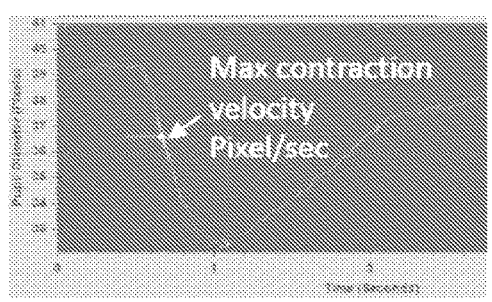
Figure 37:
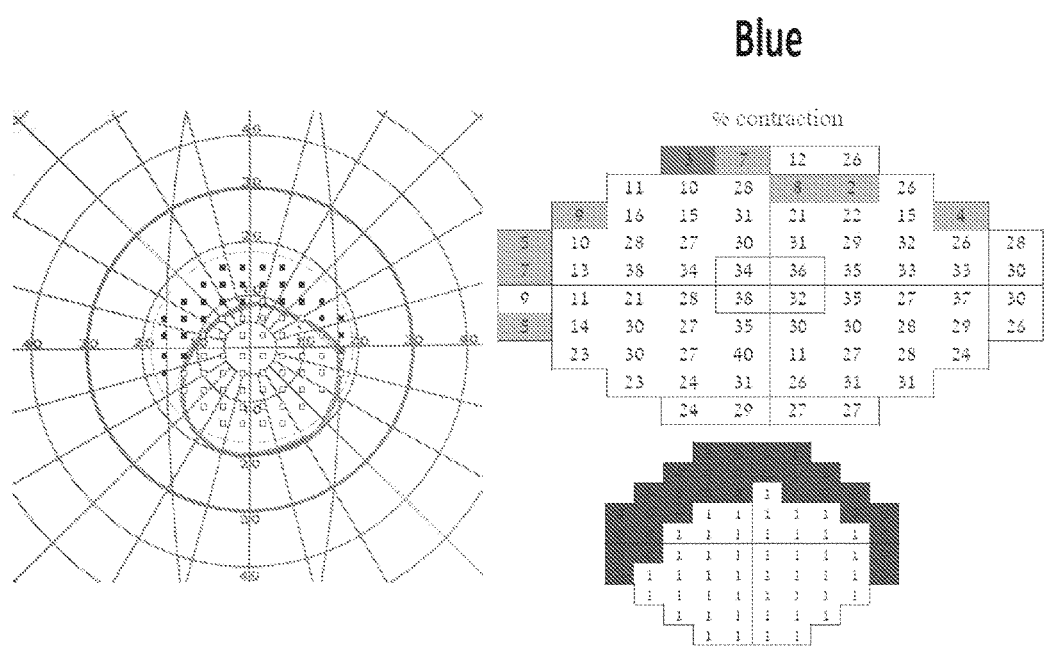
FIG. 37 shows testing results from a selected RP patient, in RP testing.
Figure 38:
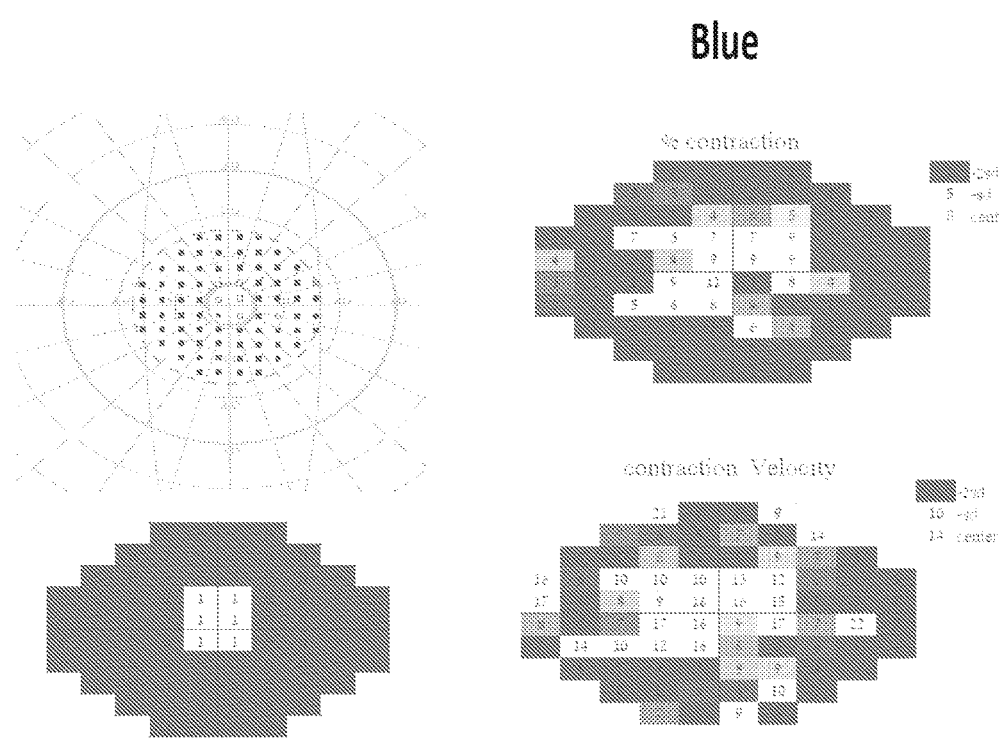
FIGS. 38 and 39 show testing results from another selected RP patient, in RP testing.
Figure 39:
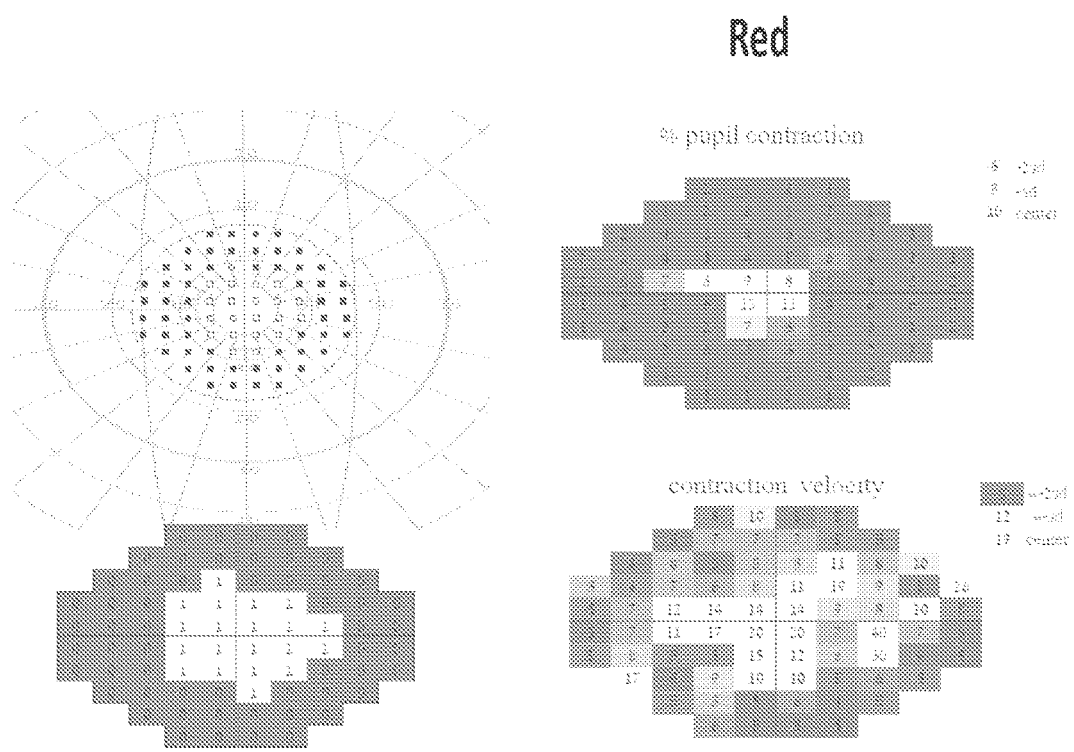

FIG. 35 shows that RP patients demonstrated a reduced percentage of maximal constriction mostly in peripheral locations. FIG. 36 shows that RP patients demonstrated a significantly reduced maximal contraction velocity in the majority of locations in response to blue stimulus. (FIG. 37 shows results from one selected RP patient, and FIGS. 38 and 39 show results from another selected RP patient.)

Example 10—Best Disease (Vitelliform Macular Dystrophy) Patients

Figure 40:
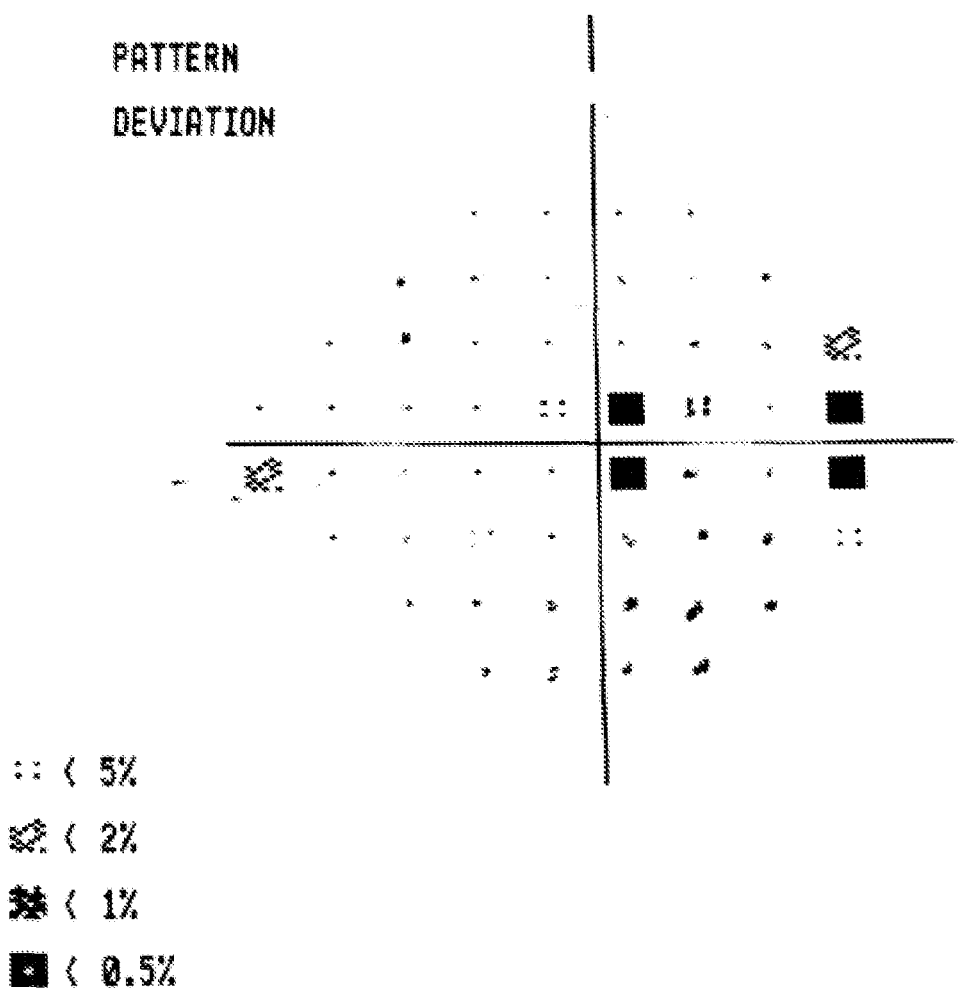
FIG. 40 shows pattern deviation for the development of scotoma in Best disease.

Best disease (Vitelliform Macular Dystrophy) is an autosomal dominant disease that affects the retinal pigment epithelium (RPE) at a very young age. The disease is characterized by lipofuscin accumulation in the RPE. Atrophic changes of the RPE or scarring secondary to subretinal neovascular membranes with hemorrhage cause loss of central visual acuity in patients with this disease. Typically, patients will present with an early central scotoma. More dense scotomas will likely develop as the disease progresses (FIG. 40).

The system and method described in FIGS. 1-3 was tested on the eyes of 4 Best disease patients (ages 22-55) and seventeen healthy volunteers (ages 26-77). Pupil responses to short and long wavelengths at increasing light intensities were tested using a full 76-point visual field. A comparison was made between the patients and the healthy controls for all perimetry locations using a one-way Anovea analysis. In the patients, subjective visual field (Humphrey) was compared with chromatic pupillometer results.

Figure 41:
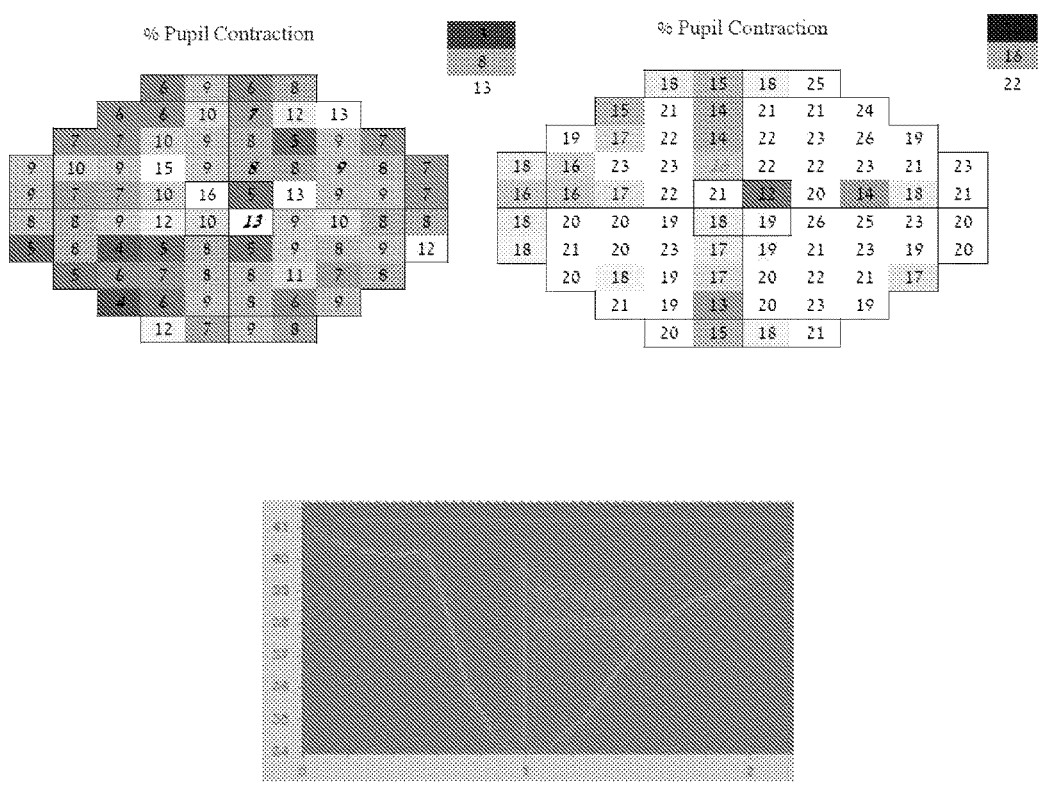
FIG. 41 shows percentage of pupil contraction for red and blue stimulus, in Best disease testing.
Figure 42:
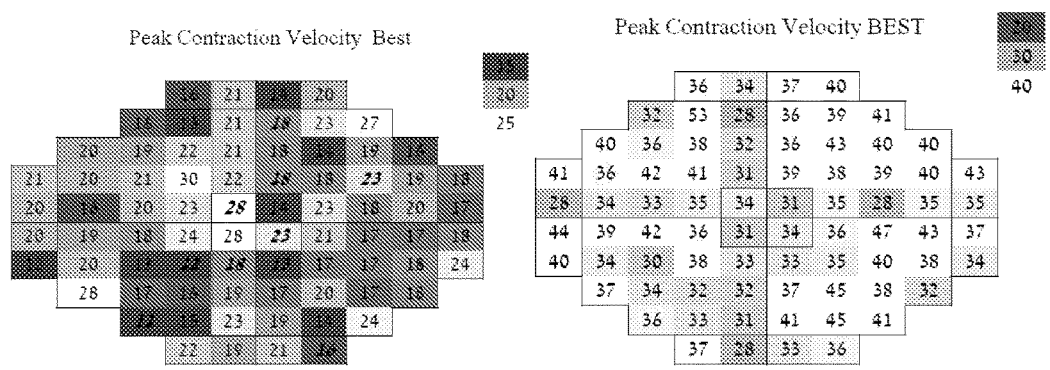
FIGS. 42 and 43 show maximal contraction velocity for red and blue stimulus, in Best disease testing.
Figure 42:
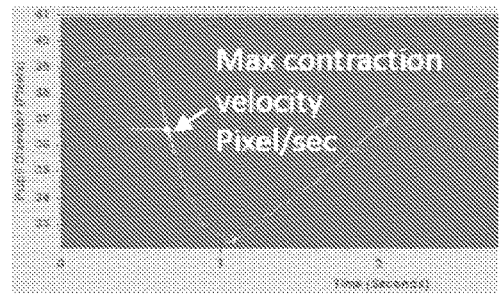
Figure 43:
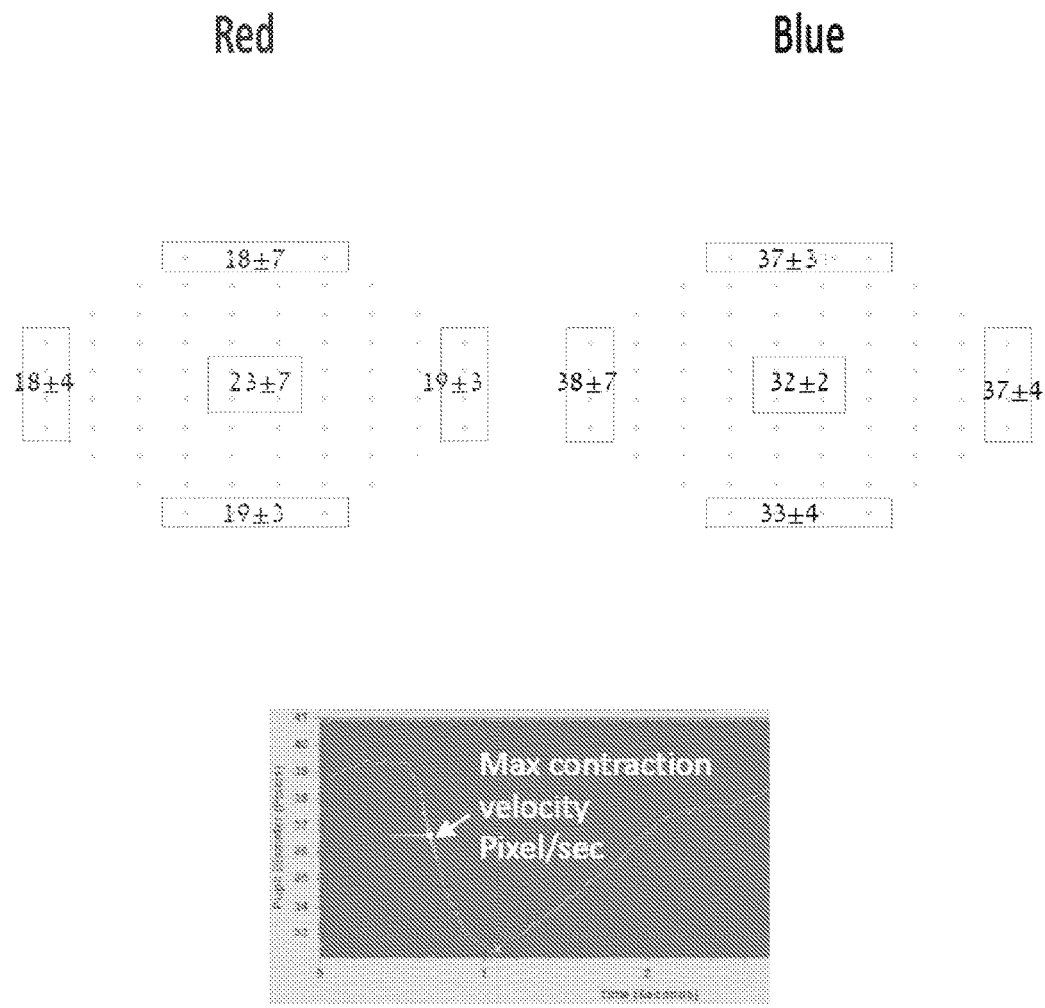
Figure 44:
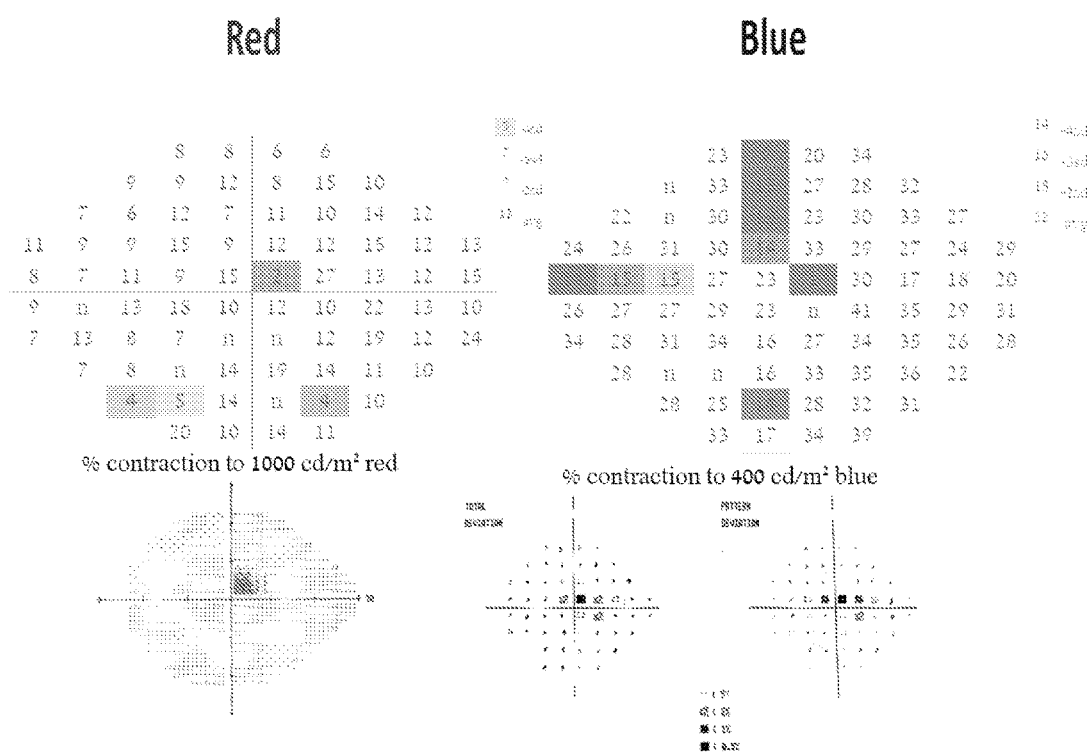
FIG. 44 shows testing results from a selected Best disease patient, in Best disease testing.

As shown in FIG. 41, the percentage of pupil contraction was lower at nearly all locations in response to the red stimulus. As shown in FIG. 42, the maximal contraction velocity for Best patients was lower at nearly all locations in response to the red stimulus. As shown in FIG. 42, the velocity contraction in response to the blue stimulus was lower in the center. (FIG. 44 shows test results from one selected Best patient.)

In the Best patients, larger regions with abnormally reduced pupillary responses were detected in response to the red stimuli as compared with the blue stimuli. An agreement was observed between the Humphrey's perimetry and the perimetry obtained by pupillary responses. From the study, it can be concluded that (i) pupillometer-based chromatic perimetry is feasible for objective assessment of visual field defects and retinal function in patients with Best vitelliform macular dystrophy, (ii) perimetry testing based on pupillary responses to red stimuli is more sensitive and may enable earlier detection of visual field defects in patients with central macular lesions, (iii) there is a good correlation between PLR and visual field, (iv) RP & Best patients demonstrated a correlation between the pathology and the visual field obtained by the chromatic pupillometer, (v) the chromatic pupillometer demonstrated reliable and consistent objective results, and (vi) there is a high test-retest correlation in the parameters of percentage contraction and maximal contraction velocity.

Exemplary Embodiments 1, 2, and 3

Method and Apparatus for Brain-Injury Detection, Portable Binocular Apparatus for Objective Chromatic Perimetry Analysis, and Portable Monocular Apparatus for Objective Chromatic Perimetry Analysis By using a device and/or method consistent with certain embodiments of the invention, severe traumatic brain injury may be quickly and accurately detected, particularly in the field, using a portable chromatic pupillometer.

Briefly, traumatic brain injury (TBI) is a nondegenerative, noncongenital insult to the brain from an external mechanical force, possibly leading to permanent or temporary impairment of cognitive, physical, and psychosocial functions, with an associated diminished or altered state of consciousness. Blows to the head, blast injuries, and vehicle collisions are common causes for combat-related TBIs. TBI and its related disabilities are a leading cause of death and disability worldwide. Patients with TBI may experience unnecessary delays in diagnosis, and therefore treatment, due to a lack of a reliable and sensitive method to diagnose TBI severity, which can lead to worse outcomes, such as death. However, there is no reliable and sensitive method for diagnosis of TBI severity in the field. Anomalous pupillary responses correlate with poor overall prognosis, and recent clinical studies demonstrated that changes in pupillary responsiveness precede changes in brain volume, suggesting that measurement of pupillary response may be used for early detection of changes in TBI severity. Currently, assessment of a pupil's shape and size is done using a flashlight. This current assessment is a full-field stimulus assessment, not a quantitative assessment, and is characterized by a large inter-examiner variability and lack of a uniform standard, limiting the ability to use this vital element in a systematic and reliable fashion, disregarding different elements that affect pupil constriction, such as different photoreceptors' ganglion cells, as well as disregarding the possibility that early TBI can affect part of the visual pupillary path. Early detection can be significantly affected when only some of those elements are reduced, while others remain normal. In this embodiment, a chromatic multifocal pupillometer is disclosed that enables the objective and accurate measurement of pupillary response to chromatic light at different wavelengths and light intensities and at different visual field locations. Using such a multifocal pupillometer, visual field defects were successfully mapped in retinal dystrophy and optic neuropathy patients and the causative defected neural cells. A significantly reduced pupillary response in patients with optic nerve damage was demonstrated.

Accordingly, a portable version of such a device can be used to quantitatively measure the pupillary response to chromatic light in both eyes simultaneously. This binocular multifocal chromatic pupillometer monitors TBI by examining the pupillary response to multifocal chromatic stimuli in intracranial pressure (ICP)-monitored severe TBI patients. In one method for confirming efficacy, pupillary responses are evaluated at admittance to Intensive Care Unit (ICU), prior to insertion of ICP and to computed tomography (CT) scans, 3 times a day during the first week following injury and with every change in ICP (more than 5 mmHg lasting for more than 15 min). It is expected that the pupillometer will enable the detection of changes in brain injury severity in correlation with changes in ICP and in CT scan results. Moreover, the pupillometer may further detect changes in the severity of the brain injury earlier than ICP.

The chromatic multifocal binocular design of a pupillometer provides accurate quantitative results, as well as early detection of pupil size asymmetries, leading to non-invasive and early diagnosis of deterioration in brain volume and better patient care, and non-invasive, user-friendly, and easy application for children, elderly, bedridden, and non-cooperative subjects, and the like. As time is everything in the decision to evacuate patients with brain damage, a portable chromatic pupillometer will enable fast triage and treatment of TBI patients in the field, e.g., during battles, terrorist attacks, use of chemical warfare, or the like. This will lead to improved patient outcome, will save lives and reduce the high costs of rehabilitation.

By way of background, TBI is a signature injury of combats and tenor attacks. Up to 25% of all ground troops may suffer some type of TBI injury following combat due to blast injuries, vehicle collisions, or blows to the head. A large numbers of traumatic brain injured veterans require medical treatment and rehabilitation following wars. In Europe, an overall average TBI incidence rate derived from estimates of hospitalized patients plus deaths is about 235 per 100,000 and in China, severe TBI accounts for approximately 20% of brain injuries. The U.S. Centers for Disease Control and Prevention (CDC) estimate that more than 1.7 million Americans sustain TBI each year. Of these, approximately 1.36 million (80%) require emergency department visits, 275,000 (16%) are hospitalized, and 52,000 (3%) die.

The brain damage can be focal, confined to one area of the brain, or diffuse involving more than one area of the brain. Currently, TBI is graded as mild, moderate, or severe on the basis of the Glasgow Coma Scale (GCS). Moderate brain injury is defined as a Glasgow Coma Scale score of 9 to 12. These patients recover the fastest within the first six months and more gradually after that and may carry life-long disabilities. In severe injury (GCS 3-8) the subject is comatose, unable to open their eyes or follow commands. Mortality rates are highest in the severe category of TBI. Studies involving about 6000 severe TBI patients (GCS≤8) observed mortality rates ranging from 20% to as high as 39%. These patients may never regain consciousness if they do survive and have the least chance of return to full pre-injury function.

TBI is a major contributor to community rehabilitation costs in trauma care. According to the CDC, 5.3 million Americans (2% of the population) are living with some degree of disability from a prior TBI. These patients have a long-term or lifelong need for help to perform activities of daily living as a result of TBI. In the US, the direct and indirect costs of TBI are estimated at $60 billion.

There are several interventions which might increase favorable outcomes in TBI patients including early drainage of CSF using a cerebral ventriculostomy catheter (EVD); therapeutic hypothermia; barbiturate coma; and surgical decompression. Unnecessary delays in the diagnosis and treatment of brain damage in patients who can benefit from evacuation procedures can lead to worse brain injury, outcome and, sometimes, unnecessary death. Unfortunately, it is not practical to have neuroimaging (e.g. computerized axial tomography or magnetic resonance imaging) available in all ambulances or field units and there is no reliable, sensitive, and specific method for in-field identification of severe TBI. Certain embodiments of the invention involve the use of a portable device that accomplishes detection of severe TBI, e.g., in the field and in emergency departments, based on changes in pupillary response to chromatic light.

The pupillary reflex is controlled by different neuroanatomical pathways. Changes in pupillary response can reflect the integrity and functionality of these pathways, and assessment of pupil shape and size is part of the routine neurological examination for brain injuries. Since the pupillomotor nuclei are located in the dorsal midbrain, and the efferent oculomotor nerve run from the midbrain to the superior orbital fissure, abnormal pupillary responses and pupil size asymmetries (anisocoria) can be used for assessing the onset of descending transtentorial herniation and brainstem compression. In addition, blood flow imaging revealed that pupillary changes are highly correlated with brainstem oxygenation and perfusion/ischemia. Numerous studies demonstrated a strong correlation between pupil size asymmetries and anomalous pupillary responses detected at the bedside of the patient, and poor overall prognosis. Furthermore, neurological worsening is usually detected by the attending staff based on changes in pupillary symmetry or pupillary reactivity. It has been reported that, in 73% of patients who had episode of neurological deterioration, the deterioration was declared on the basis of pupillary changes. In that study, the mortality rate in patients with pupillary abnormalities was 62%, whereas only 20% of patients had fatal outcomes when neurological deterioration was not accompanied by changes in pupils. Importantly, it has been shown that patients who undergo prompt intervention (i.e., surgery, hyperventilation, hyperosmolar therapy) after a new pupillary abnormality have improved recovery potential.

The pupil's response to light can be evaluated in different types of injuries. There are afferent and efferent pupillary defects. Afferent pupillary defects can be caused by defects in the photoreceptors' rods or cones, or ganglion cells. The pupils show relative afferent pupillary defects when the optic nerve of one eye is more injured than that of the other eye. Currently, changes in pupillary size and response are visually assessed as part of the clinical routine using a flashlight. These assessments are characterized by a large inter-examiner variability due to their subjectivity, crude impression, inaccurate amplitude and time measurements, different lighting conditions in patients' rooms, differences in flashlight stimulus intensity, distance and orientation of the flashlight and the patients' eyes, and the variability in examiners' visual acuity. The lack of a uniform standard for assessment of the pupils and the unavailability of an objective and quantitative means to measure pupillary function limits the ability to assess one of the most vital elements of the neurological examination in a systematic and reliable fashion.

Hence there is a need for an accurate quantitative method for pupil assessment, as earlier detection of changes in pupillary function, not detectable to the naked eye, may predict deterioration or improvement in brain volume, and patient outcomes could potentially be improved by modifications in patient care if an earlier warning of pending deterioration could be obtained. Moreover, the multifocal nature of a system consistent with embodiments of the invention provides more accurate relative afferent defect comparing sectors of fibers of the optic nerve, and not all total fibers between each eye, thereby enabling a more sensitive method for measuring small relative afferent pupillary defects. In addition, the option of stimulating selective photoreceptors or ganglion cells allows, on one hand, more information, and, on the other hand, more sensitive detection. Additional multifocal non-relative pupillary defects would also be possible to diagnose in case both eyes are injured.

Another application of pupil measurement is the efferent pupillary defect, which can be caused by pressure on the occulomotor nerve (III). In this scenario, the pupillary response of the other eye will be normal when applying the stimulus to the injured side, and all three responses (i.e., red, blue, and bright blue) would be equally affected.

Several quantitative pupillometer devices using non chromatic white light stimulus and testing single eyes have been developed and used primarily in research settings either because the devices have been relatively cumbersome or because they have not been easily adaptable to the clinical environment of the critically ill patient. Nevertheless, these studies reported a trend of inverse relationship between decreasing pupil reactivity and increasing intracranial pressure (ICP), a common monitoring method for TBI. ICP is typically measured using probes that are inserted into one of the lateral ventricles or the brain parenchyma. Raised ICPs (>20 mmHg) is an important secondary insult in brain-injured patients and result more frequently in poor neurological outcomes and death. Therefore ICP monitoring is invaluable in directing therapy for the brain-injured patient. Importantly, it has been reported that in some cases pupillary changes were detected 16 hours prior to the time of peak ICP, suggesting that a pupillometer device that could track and classify pupillary changes in a more sensitive and accurate manner may enable early evaluation of patients with suspected intracranial pathology and elevated ICPs, before imaging studies are completed and ICP monitors are placed.

In one embodiment, the present invention provides a chromatic multifocal pupillometer that enables the objective and accurate measurement of pupillary response to chromatic light at different wavelengths and light intensities and at different visual field locations. Previous studies demonstrated that the pupillary response to different wavelengths, stimulus intensities and stimulus durations reflects activation of different outer and inner retinal cells. It was suggested that the transient pupillary response to a low-intensity, short-wavelength stimulus reflects rod photorecptor activity, that the transient pupillary response to a long-wavelength stimulus is predominantly driven by cone photoreceptors, and that a sustained pupillary response to a continuous high-intensity short-wavelength stimulus is derived primarily from the direct intrinsic activation of the optic nerve melanopsin ganglion cells. Using our multifocal pupillometer we successfully mapped visual field defects in retinal dystrophy patients and the causative defected cells. Employing short and long-wavelength stimuli at low intensity we discriminated the between visual field defects due to damage in different photoreceptor cells (rod or cones, respectively). Using short-wavelength stimuli at high intensity we successfully identified visual field defects due to damage in the optic nerve. It is reasonable to assume that increased ICP would change the pupil reaction to light in a small area of the visual field at early stages and later more neural fibers would be involved. Eventually, with increase in TBI severity, a full field stimulus would be required for evoking the pupillary reflex. Stimulation of part of the neural fibers of the pupillary reflex would probably enable early diagnosis of the effected perimetry fibers and may enable to the identification of affected and non affected areas.

Certain embodiments of the invention employ a portable pupillometer that enables the measurement of changes in pupillary response to chromatic light in both eyes simultaneously in severe TBI patients. The chromatic multifocal design of this pupillometer enables more accurate results due to multiple measurements and enables insight to be gained on the location of the damage due to the use of multifocal stimulus, using a non-invasive method. Furthermore, the binocular design of the device enables early and quick detection of pupil size asymmetries, leading to early diagnosis of increased pressure on one side of the brain and possibly early triage and intervention.

Based on successful preliminary test results, as described in further detail below, a small portable variation of the pupillometer used during the testing has been designed. Using the portable device, pupillary responses to chromatic light stimuli are monitored at 5 different visual field locations in severe TBI patients, and the correlation between changes in pupillary responses and changes in ICP in these patients can be observed, to demonstrate the feasibility of using this chromatic multifocal pupillometer for triage and monitoring patients with acute head injury.

In one exemplary embodiment of a multifocal chromatic pupillometer, light stimuli were presented 30 mm from the patient's eyes, and controlled with a stimulus generator and custom-built software. Stimuli were presented from the center and 4 other locations in the visual field (superior, inferior, temporal and nasal fields at angle of 20°). Light stimuli were at 640±5 nm for red light (long wavelength, intensity 15 cd/m$^2$) and 480±5 nm for blue light (short wavelength, at 15 and 100 cd/m$^2$). Each stimulus was presented using stimulus size V (64 mm$^2$) on a background luminance of 2.7 cd/m$^2$. Stimulus duration was 1 second, and the inter-stimulus interval was 10 seconds. Pupil diameters were recorded in real time by a computerized infrared pupillometer, which included a monitor with viewing optics for presentation of a light stimulus to the subject. Pupil tracking was performed by an infrared camera that recorded the pupillary response at a sampling rate of 34 Hz. This system captured images of the subject's eye and percent of pupil contraction at each time point, determined by the following formula: Percent pupil contraction=100×[The difference between the highest initial diameter at the beginning of the stimulus and the lowest diameter in response to that stimulus]/[The highest initial pupil diameter]. Previous studies have demonstrated that contraction of the pupil is a true pupillary reflex when the initial pupillary contraction (time at which the maximum acceleration occurs) falls within a definite time window (200-450 ms after stimulus onset). Accordingly, pupillary contraction was recorded only when the initial pupillary contraction was within this time window.

Figure 7A:
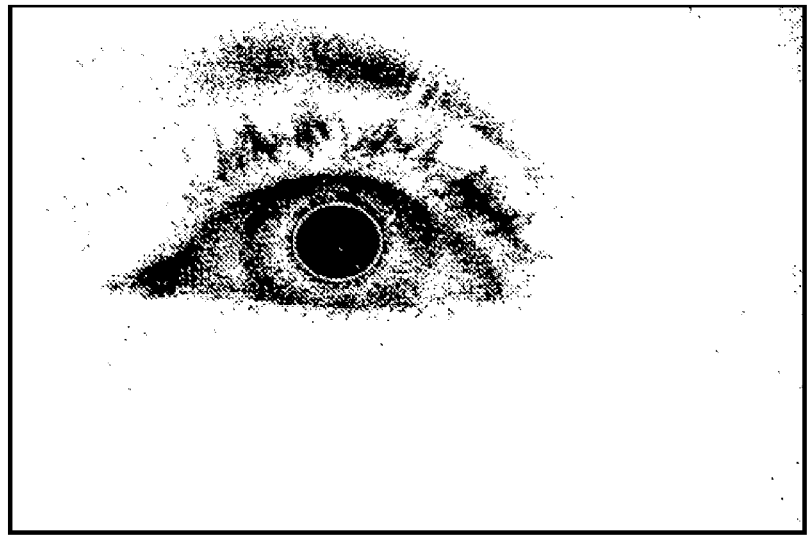
FIGS. 7A and 7B show an example of a pupil tracking from a normal subject, where
Figure 7B:
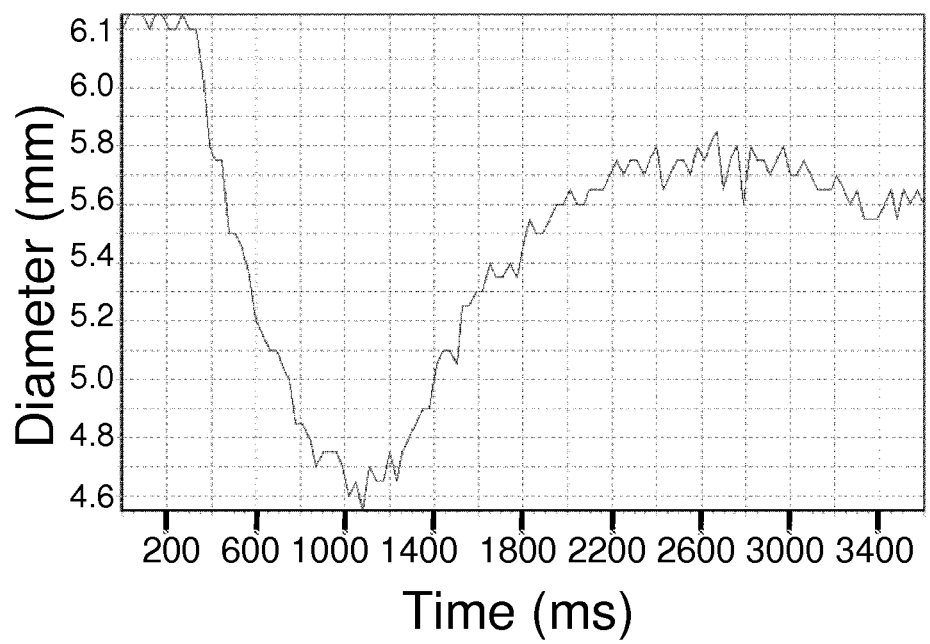

FIGS. 7A and 7B show an example of a pupil tracking from a normal subject. FIG. 7A shows an infrared video image of a pupil while being recorded with the pupil tracking system. FIG. 7B shows an example of pupil recordings from the chromatic multifocal pupillometer. The x-axis presents the time scale in milliseconds, and the y-axis records the pupil diameter in millimeters.

Figure 8A:
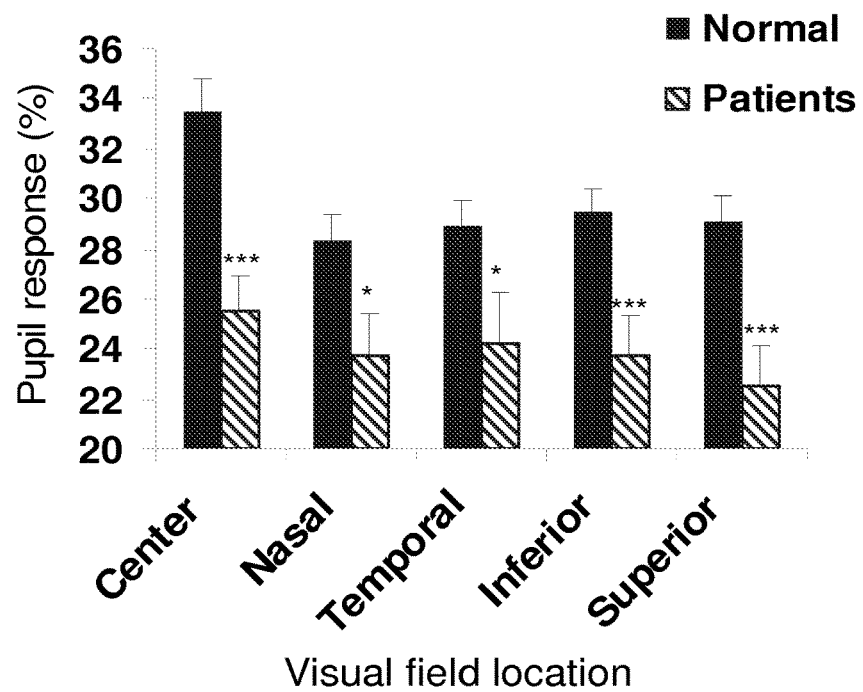
FIGS. 8A-8C show study results of the pupillary response of patients with optic nerve damage and normal subjects, evaluated using the chromatic pupillometer.
Figure 8B:
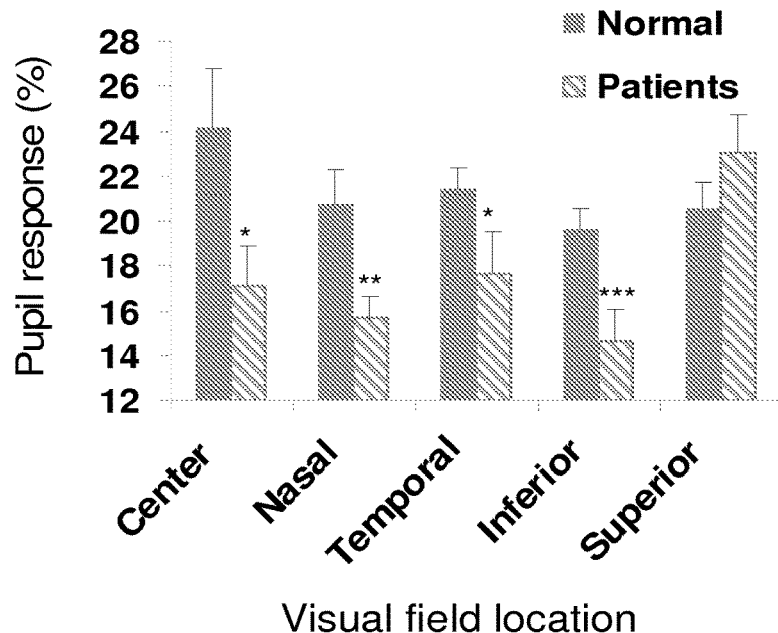
Figure 8C:
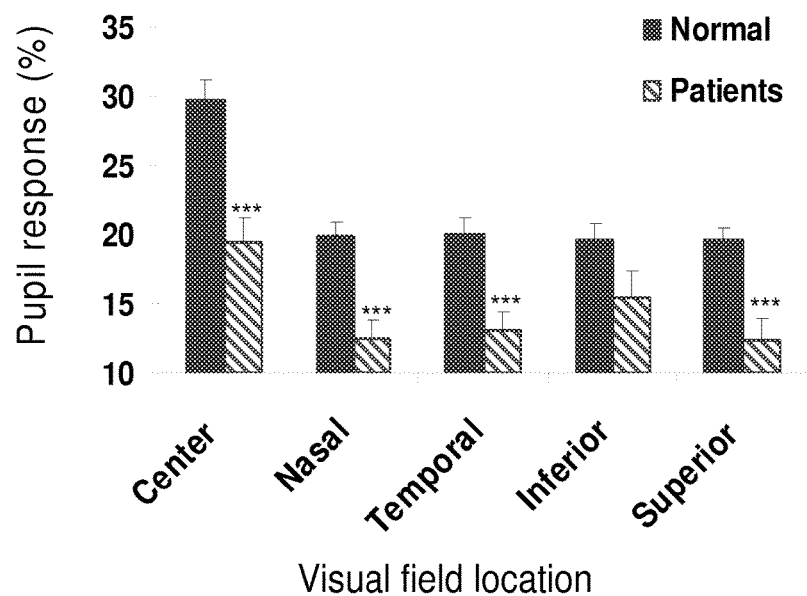

It can be seen in FIGS. 8A-8C that patients with optic nerve damage demonstrate reduced pupillary response to chromatic light stimuli. The pupillary response of 22 eyes of 11 patients and 38 eyes of 19 normal subjects was evaluated using the chromatic pupillometer. The percentages of change in pupil size in response to blue light stimuli at 100 cd/m$^2$ (FIG. 8A) and blue (FIG. 8B) and red (FIG. 8C) light stimuli at 15 cd/m$^2$ were measured at the center of visual field as well as the indicated peripheral locations at 20°. Patients with optic nerve damage showed significantly reduced pupillary responses in all perimetric locations under testing conditions that emphasized optic nerve cell contribution (short-wavelength stimuli at high intensity, P<0.05, FIG. 8A) and in most perimetric locations under conditions that emphasized rod and cones contribution (p<0.05, FIGS. 8B-C). These preliminary findings clearly demonstrate the ability to monitor changes in pupillary responses in normal subjects and in patients with neurological defects, and serves as the basis for the use of portable chromatic pupillometer to monitor pupil changes in TBI patients.

FIGS. 9A-9H show various views of an exemplary portable binocular pupillometer 900 consistent with one embodiment of the invention. It should be understood that some components are omitted in FIGS. 9A-9H for clarity, and that components omitted from FIGS. 9A-9H are similar or identical to those described above with respect to the system of FIGS. 1A and 1B.

Figure 9A:
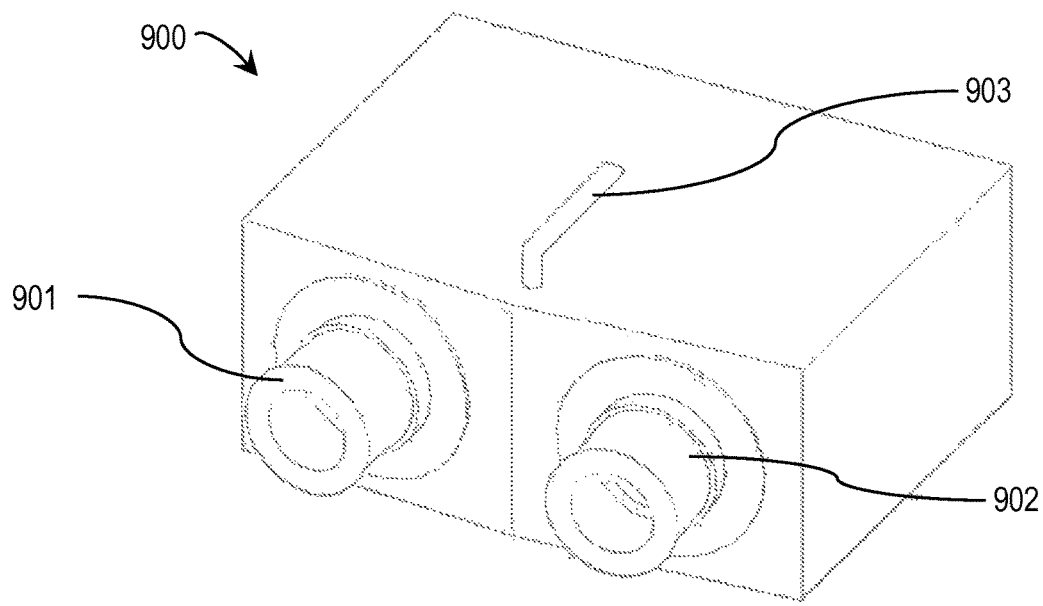
FIG. 9A shows a front perspective view of an exemplary portable binocular pupillometer consistent with one embodiment of the invention.

FIG. 9A shows a front perspective view of the binocular pupillometer 900, which includes a left ocular 901 and a right ocular 902, and an eye cover handle 903.

Figure 9B:
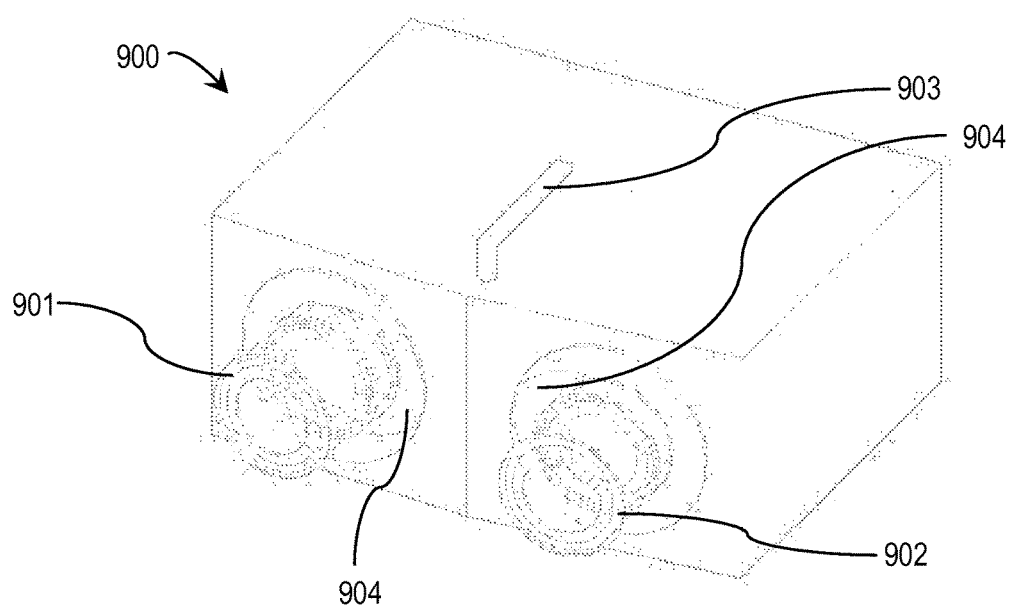
FIG. 9B shows the adjustable eye positioning function of the binocular pupillometer of FIG. 9A, adjusted for a wide view.
Figure 9C:
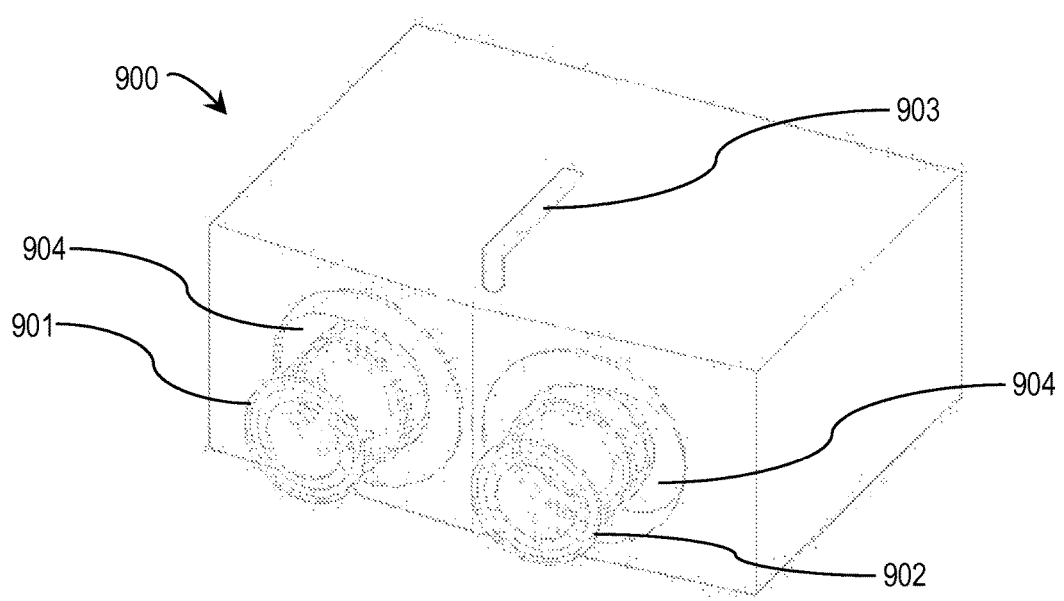
FIG. 9C shows the adjustable eye positioning function of the binocular pupillometer of FIG. 9A, adjusted for a narrow view.

FIG. 9B shows that each of oculars 901 and 902 is slidably disposed in a respective elongated horizontally-formed aperture 904 so as to permit the distance between oculars 901 and 902 to be adjustable. In FIG. 9B, oculars 901 and 902 are adjusted for a wider view. FIG. 9C shows oculars 901 and 902 adjusted for a narrower view.

Figure 9D:
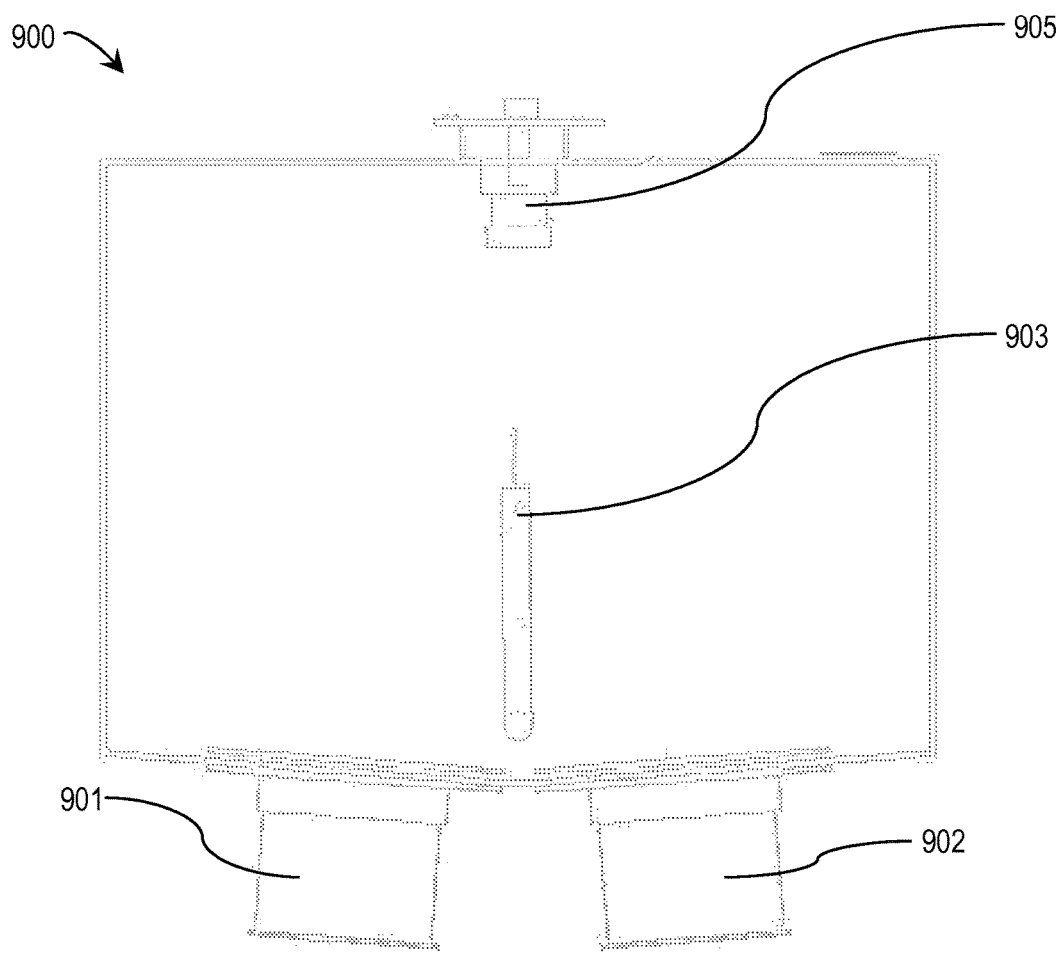
FIG. 9D shows a top plan "X-ray" view of the binocular pupillometer of FIG. 9A.

FIG. 9D shows an "X-ray" top plan view of pupillometer 900, including wide-angle lens camera 905 disposed inside pupillometer and eye cover handle 903 protruding through the top surface (not shown) of pupillometer 900.

Figure 9E:
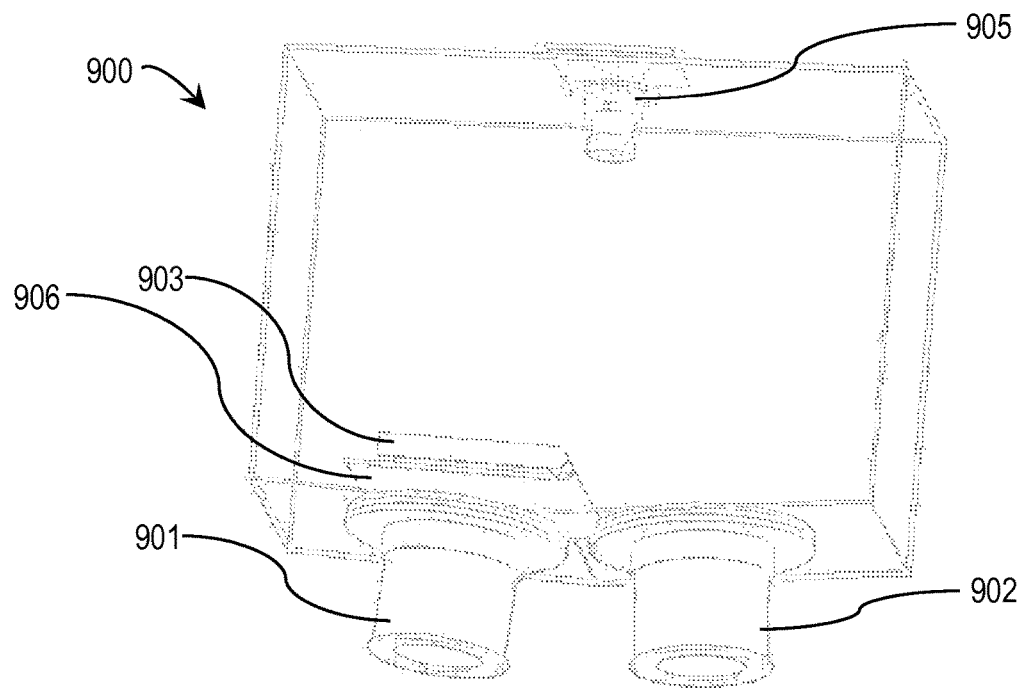
FIG. 9E shows a top perspective "X-ray" view of the binocular pupillometer of FIG. 9A covering the left eye.
Figure 9F:
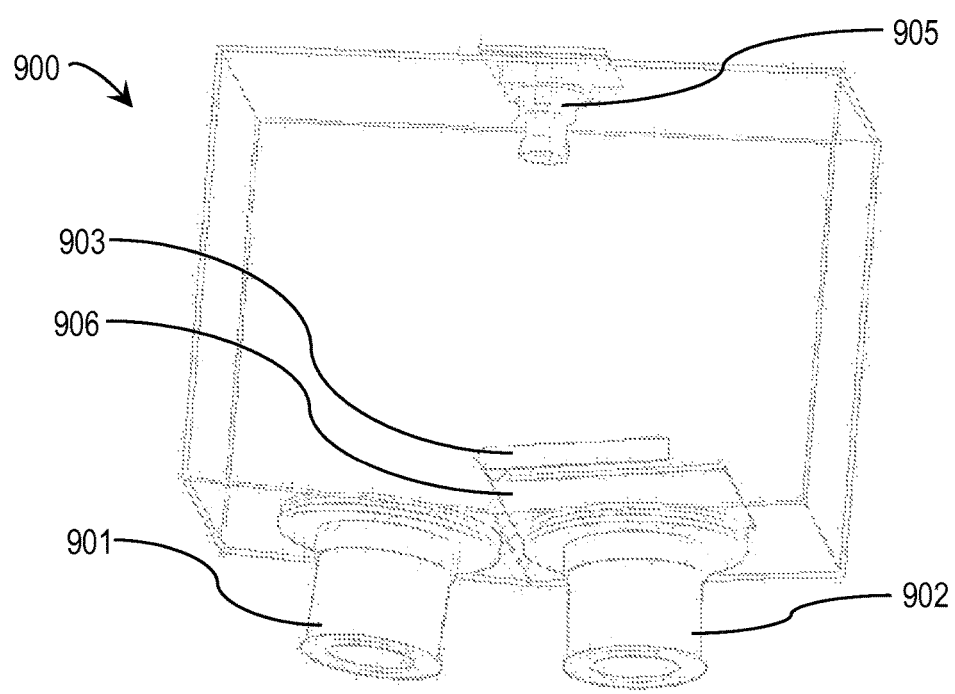
FIG. 9F shows a top perspective "X-ray" view of the binocular pupillometer of FIG. 9A covering the right eye.

As best seen in FIGS. 9E and 9F, eye cover handle 903 is coupled to an eye cover 906 rotatably disposed inside pupillometer 900 so as to permit eye cover 906 to selectively cover one eye while the other eye is being tested. FIG. 9E shows a view of eye cover handle 903 moved so that eye cover 906 covers the left eye, and FIG. 9F shows a view of eye cover handle 903 moved so that eye cover 906 covers the right eye. In a third position (not shown), the eye cover handle 903 is moved centrally so as to cover neither eye and permit both eyes to be tested concurrently.

Figure 9G:
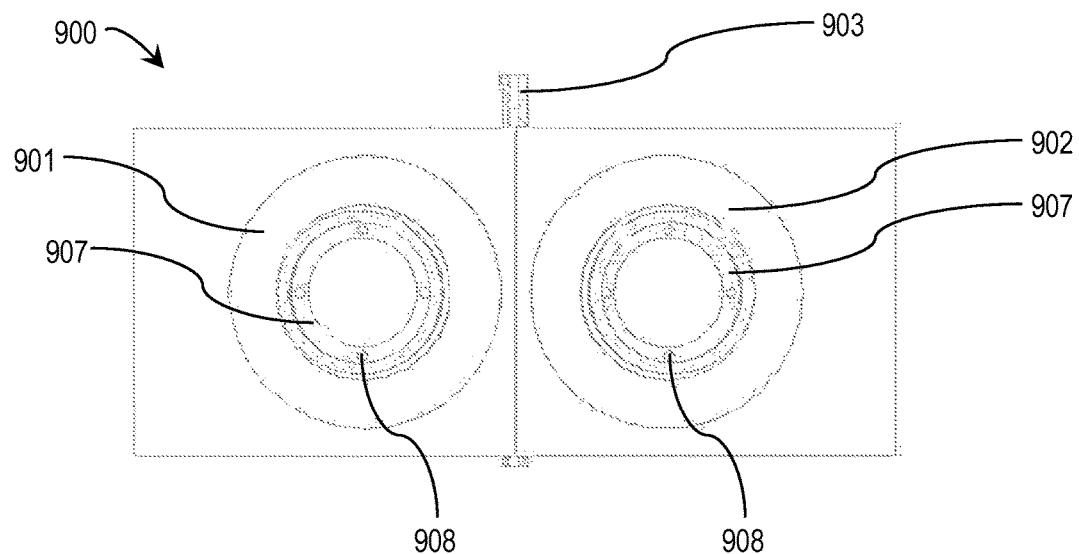
FIG. 9G shows a front perspective "X-ray" view of the binocular pupillometer of FIG. 9A showing the LED PC boards.

FIG. 9G shows an "X-ray" front perspective view of pupillometer 900, including the mounting of each of LED PC boards 907 at an interior portion of a respective ocular 901, 902 via mounts 908. Each PC board 907 has mounted thereon a plurality of LEDs (not shown) or other light sources for producing visual stimuli as described and illustrated herein.

Figure 9H:
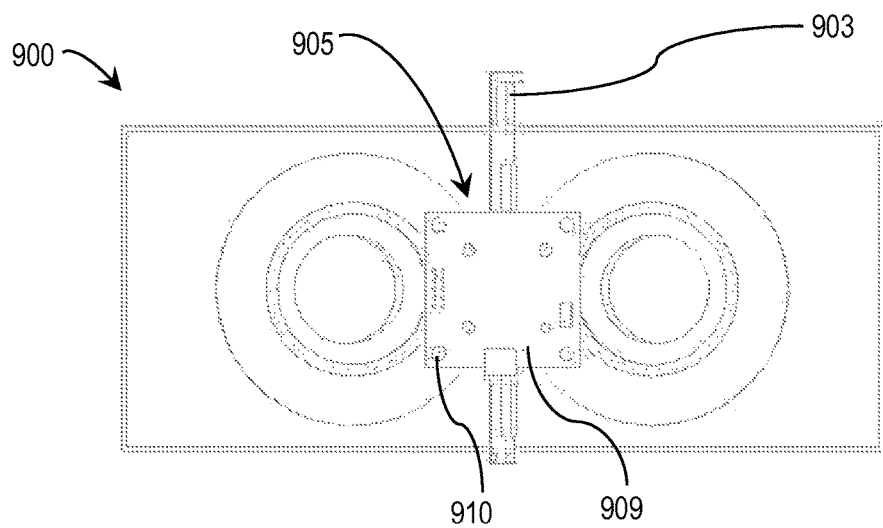
FIG. 9H shows a rear perspective "X-ray" view of the binocular pupillometer of FIG. 9A showing the rear PC board of the camera.

FIG. 9H shows an "X-ray" rear perspective view of pupillometer 900 showing the rear PC board 909 of camera 905, which is mounted to a rear surface (not shown) of pupillometer 900 via mounts 910.

In one exemplary embodiment, the portable binocular pupillometer is adapted for connection to a personal computer (PC), such as a laptop computer, tablet, smartphone, or the like, executing appropriate software to effect the functionality described herein. First, the pupillometer is connected to the PC (e.g., via a USB cable or WiFi connection), and the software is executed. Second, the pupillometer, e.g., in the form of a head-mounted reader device shown in FIGS. 9A-H, is placed over the subject's eyes, covering both eyes. Third, one eye (right or left) is initially selected, and the PC software is instructed by the operator to initiate capture of the subject's pupil via infrared detection. Fourth, the testing sequence begins (e.g., the exemplary testing sequence described below), and the PC software automatically begins capturing the subject's pupil responses to different light stimulations. Fifth, the PC software displays the results on the screen in a format (e.g., percentage of change) designed for the operator to make appropriate determinations for further diagnosis.

In one exemplary testing sequence referred to in the fourth step above, a binocular pupillometer as shown in FIGS. 9A-9H measures the pupillary response simultaneously in both eyes. Each eye is stimulated by 5 stimulus targets (center and up, down, temporal and nasal 20 degrees from center with blue and red lights). The light is polarized by a filter. Stimulus duration is 1000 ms, with intervals of 495 ms between stimuli. A double-channel computerized pupillometer is used to record the size of each pupil with alternating short wavelength and long wavelength light stimuli (recording time=4488 ms) for each fixation point. A total recording time of 100 s for all stimuli is employed. The stimuli data are: Target size, III; light intensity of 100 cd-s/m2 for short wavelength (480±5 nm) and 15 cd-s/m2 for short and long (640±5 nm). Pupil diameter is monitored under infrared illumination. Light intensities are chosen in compliance with safety regulations of light use, well below the recommendations of American National Standard (ANSI-2007) and International Commission on Non-Ionizing Radiation Protection (ICNIRP) for red, blue and infrared illumination.

In certain exemplary methods of use, a binocular pupillometer as shown in FIGS. 9A-9H permits measurement of pupil reactivity in a functional and non-invasive manner. Pupil amplitude response and pupil latency response for different stimuli are measured, and these results are analyzed by an algorithm to evaluate each of the visual field spots. The background light is 2 cd/m$^2$. One or more of the following data items are collected (either manually or using equipment such as a camera) from patients: Iris architecture (color, pigmentation, maximal pharmacologic dilatation).

Intra Cranial Pressure (ICP) is a routine measure in TBI patients. The normal values of ICP vary but should be below 20-25 mmHg. Increased ICP can result from, e.g., hematoma, brain edema, or additional intra-cranial volume. ICP is monitored using intra ventricular, subdural, or intraparenchymal device. Treatment of TBI is directed to the reduction of increased ICP.

The chromatic multifocal binocular design of the portable pupillometer provides accurate objective quantitative pupil measurements as well as early detection of pupil-size asymmetries, leading to non-invasive and early diagnosis of deterioration in brain volume and improved patient care.

Although the foregoing description refers to the use of a portable binocular pupillometer for objective chromatic perimetry analysis, a portable monocular pupillometer could alternatively be used.

Figure 10A:
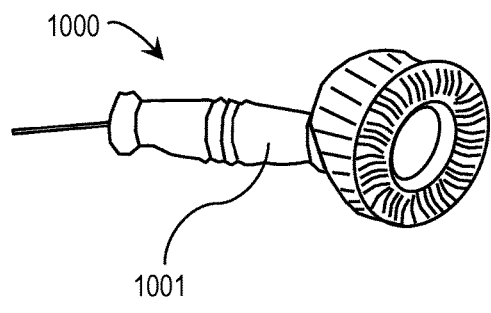
FIGS. 10A and 10B show perspective views of an exemplary portable monocular pupillometer consistent with one embodiment of the invention.
Figure 10B:
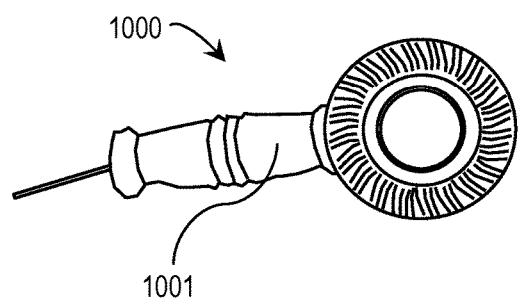
Figure 10C:
FIG. 10C shows the pupillometer of FIGS. 10A and 10B during use with the eye of a person being tested.

For example, FIGS. 10A and 10B show, respectively, two different perspective views of an exemplary portable monocular pupillometer 1000 consistent with one embodiment of the invention. FIG. 10C shows pupillometer 1000 in use with a patient's eye. It should be understood that some components are omitted in FIGS. 10A-10C for clarity, and that components omitted from FIGS. 10A-10C are similar or identical to those described above with respect to the system of FIGS. 1A and 1B. As seen in FIGS. 10A-10C, pupillometer 1000 is a hand-held portable monocular unit having a handle 1001.

Figure 11:
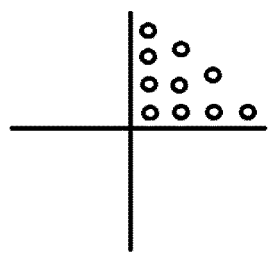
FIG. 11 shows a diagram of an exemplary grid system for the visual field map disposed within the pupillometer of FIGS. 10A-10B.

In one exemplary embodiment, as shown in FIG. 11, a grid system for the visual field map disposed within the pupillometer includes 10 total stimuli located 6° apart in one quadrant of the visual field, wherein the stimuli are: red light (long wavelength ~640±5 nm) and blue light (short wavelength ~480±5 nm). While one eye is being tested with the portable monocular pupillometer, the other eye may be obscured using a patch, dome, or other covering device.

It should be understood that some embodiments of the invention may employ either a binocular or a monocular pupillometer, as described herein, and that the pupillometer may either be portable or non-portable.

In one embodiment, a portable pupillometer is adapted to communicate, either wirelessly or via a wired connection, with a communications interface (e.g., WiFi, USB, serial, Bluetooth, etc.) on a smartphone or other portable electronic computing device (or laptop, tablet, PC, etc.). In this scenario, the portable pupillometer is a very small cup containing a camera and between one and five light sources in its center and four light sources distributed evenly peripherally to permit stimulation of low vision and/or extrafoveal vision. An application ("app") executing on the smartphone controls the light sources via the communications interface. Inside the cup, a circle is marked centrally to assist in patient centration. Patient centration is also assisted by the application monitoring the patient using the camera. One or more lenses (e.g., trial lenses) and/or a refraction system may be included within or mounted on the cup.

It should also be understood that a portable pupillometer consistent with embodiments of the invention may be used not only for TBI detection, but also in chromatic perimetry analysis for conventional purposes.

To confirm the accuracy of a portable pupillometer consistent with embodiments of the invention, ICP and pupillary measurements are recorded at indicated time points. Pearson correlation analysis is performed using SPSS, to examine correlation between changes in ICP and pupillary response.

Terrorist-attack and combat-related brain injuries are very common. American-football players and other sports game players also face TBI injuries. Blast injuries, vehicle collisions, and blows to the head are a significant cause of TBI. It is very clear that time is everything in triaging and in making the decision to evacuate affected soldiers. However, currently there are no available portable field devices to help with triaging of TBI patients, especially in the field. The use of a portable pupillometer consistent with embodiments of the invention enables exact and early diagnosis of severity of TBI in the field that would facilitate a quick evacuation of soldiers who require immediate intervention and prevent costly evacuations of soldiers who do not need one. Quick triage, evacuation and treatment of TBI patients reduces brain damage, increases chances of survival, and reduces the heavy burden of rehabilitation costs of affected veterans. Furthermore, the use of a portable pupillometer consistent with embodiments of the invention in ICU enables early diagnosis of changes in brain damage status and possibly monitoring during treatment. This leads to improved treatment, survival and rehabilitation prospects for injured soldiers, as well as reduced costs of rehabilitation.

Exemplary Embodiment 4

Method and Apparatus for Veterinary Objective Chromatic Perimetry Analysis

By using a chromatic pupillometer and/or method consistent with certain embodiments of the invention, objective chromatic perimetry analysis can be performed on animals other than humans, e.g., to assess ocular and other neurological diseases or conditions (e.g., brain damage) in domestic and farm animals. In this scenario, the pupillometer, which may be constructed, e.g., in similar manner to the system shown in FIGS. 1A and 1B and/or the portable pupillometer shown in FIGS. 9A-H, is adapted to conform to the head and face shape of the animal being tested and may include one or more straps or other attachment devices (not shown). Alternatively, the animal may be restrained using some other means (e.g., body or limb restraints or gates) in a position so that the animal is properly positioned with respect to the pupillometer during use, while the pupillometer remains stationary at a predetermined location. Individual and specific pupillometer head-mounted reader devices may be constructed for specific species or breeds of animal, or alternatively, a pupillometer may be constructed to be adjustable so that the device can be used with a variety of species and/or breeds of animal for testing. Since the testing process does not involve or require active or verbal feedback or participation on the part of the subject being tested, objective chromatic perimetry analysis can be used to assess brain damage and diagnose and monitor ocular, neurological, and other diseases and conditions, as described herein, on animals other than humans. No such test is presently commercially available.

Exemplary Embodiment 5

Method and Apparatus for Intra-Ocular Lens (IOL) Evaluation

In one embodiment, a pupillometer as described hereinabove is used in assessing contrast sensitivity, e.g., to determine whether a person is an appropriate candidate for a multifocal intra-ocular lens (IOL) implantation procedure. In this scenario, the pupillometer is adapted to measure pupil diameter at different illuminations to determine whether the person has sufficiently low pupil constriction in different background illumination conditions simulating day and night vision. In a variant method, a pupillometer is adapted to assess contrast sensitivity to diagnose objectively peripheral night-vision and contrast-sensitivity reduction after multifocal IOL implantation.

Exemplary Embodiment 6

Method and Apparatus for Evaluation of Zero-Gravity Brain Trauma

Astronauts who spend prolonged periods in the zero-gravity space environment tend to show eye abnormalities linked to pressure around the brain. Specifically, the space filled with cerebral spinal fluid that surrounds the optic nerve expands, causing flattening of the rear of the eyeball and bulging of the optic nerve. In one embodiment, a mobile pupillometer is used to monitor traumatic accumulation of fluids in the brain of astronauts, by monitoring changes (symmetric and asymmetric) in pupil size using one or more non-invasive procedures, as described in further detail above with respect to TBI analysis.

Exemplary Embodiments 7 and 8

Method and Apparatus for Evaluation of Blue Light-Filtering Intra-Ocular Lenses (IOLs), and Method and Apparatus for Evaluating Correlation of Aging, ipRGC Function, and Circadian Rhythms Although intraocular lenses (IOLs) that filter blue light have been available for over 10 years, whether the benefits they provide for patients are outweighed by the disadvantages has remained a matter of debate. It is generally accepted that excessive exposure to blue light damages retinal pigment epithelial cells, a precursor to several ocular diseases, including age-related macular degeneration. Blue light has also been shown to stimulate the proliferation of choroidal melanoma cells in vitro. Proponents of blue light-filtering IOLs maintain that they should be routinely used because they can protect the retina from these potential hazards, as well as reduce glare sensitivity and cyanopsia and increase contrast sensitivity in ambient light conditions for post-cataract surgery patients. Those who do not advocate routine use of blue light-filtering IOLs question whether the benefits come at the expense of visual acuity, color vision, contrast sensitivity in scotopic light conditions, and possible interference with patients' natural circadian rhythms. Those circadian rhythms are linked to melatonin production, which is controlled by light-dark signals detected by intrinsic photosensitive Retinal Ganglion Cells (ipRGCs) containing a photopigment called melanopsin.

In one embodiment, a multifocal chromatic pupillometer is used to determine the effect of blue-light-filtering Intra Ocular Lenses (IOL) on the visual field in response to blue light and to estimate the effect of blue-light-filtering IOLs on the function of ipRGCs in different locations of the visual field.

In another embodiment, a pupillometer is used to determine possible correlations between aging, ipRGC function, and circadian rhythms in healthy subjects and patients with sleep disorders. Using a portable pupillometer system permits monitoring and examination of patients on a constant, around-the-clock basis, and in a manner not previously possible with conventional stationary pupillometry.

Exemplary Embodiment 9

Method and Apparatus for Mapping Photosensitive Retinal Ganglion Cells (RGCs)

Recent studies have reported that outdoor activity is protective against myopia development in children. This protection is most likely mediated by the activation of retinal dopaminergic pathways by the high levels of outdoor illuminance. Inputs from intrinsically-photosensitive retinal ganglion cells (ipRGCs) at elevated light are believed to provide additional activation of retinal dopaminergic pathways.

In one embodiment, a chromatic pupillometer is used for mapping photosensitive RGCs. In this manner, by using a chromatic pupillometer, the function of ipRGCs at different visual field locations can be directly determined in myopes vs. non-myopes and in children in the process of myopization.

Exemplary Embodiment 10

Method and Apparatus for Assessing Visual Acuity

In one embodiment, a stationary or portable pupillometer as described hereinabove may provide, in addition to, or instead of other functionality described above, functionality for assessing visual acuity (for example, 20/20), i.e., a measure of acuteness or clearness of vision, which depends on the sharpness of the retinal focus within the eye, the sensitivity of the nervous elements, and the interpretative faculty of the brain. A pupillometer as described hereinabove can be used to measure visual acuity, including objective visual acuity and objective best-corrected visual acuity, particularly in the center of the visual field. A pupillometer as described above may additionally or alternatively be adapted to assess contrast sensitivity.

In one embodiment, the pupillometer may be adapted to test visual acuity at a single central point and a plurality of periphery points surrounding the single central point and corresponding to a plurality of degrees of central vision deficiency.

Alternatively or additionally, the pupillometer may be adapted to test contrast sensitivity at a single central point and a plurality of periphery points surrounding the single central point and corresponding to a plurality of degrees of central vision deficiency.

In one embodiment, to test visual acuity or contrast sensitivity, the test includes visual stimulus targets selected from one or more tests such as the tumbling E, Landolt C, or letters, or numerals, or simple pictures of familiar objects. Visual acuity and/or contrast sensitivity may be assessed objectively and/or subjectively using one color or different colors, in different embodiments. The light sources used may include one or more bulbs, lasers, and light-emitting diodes (LEDs).

In one embodiment, a comparison is made between two or more of the following: (i) the visual acuity test results from some or all of the central and periphery points, (ii) the contrast sensitivity test results from some or all of the central and periphery points, (iii) an individual's subjective visual acuity (e.g., using a Snellen chart or high- and low-contrast charts, such as Michelson or Bailey-Lovie charts), and (iv) an individual's subjective best-corrected visual acuity.

Alternative Embodiments

Different embodiments of the invention may be adaptable for different and specialized purposes. Embodiments of the invention may include implementation of a pupillometer in or on a network, shared server, or hardened appliance, and may be adapted, e.g., to permit use in a wireless networking environment, such as a hospital emergency department.

It should also be understood that a pupillometer consistent with embodiments of the invention can be employed, e.g., at endpoint nodes of a network, centrally within a network, as part of a network node, between a standalone pair of interconnected devices not networked to other devices (e.g., between an industrial robot and a controller), at a user's end, at the server end, or at any other location within a scheme of interconnected devices.

Embodiments of the invention may include combinations of one or more features from one or more separate embodiments described above. For example, a stationary pupillometer consistent with one embodiment of the invention includes functionality for intra-ocular lens (IOL) evaluation as well as visual acuity assessment. In another embodiment, a portable pupillometer includes both brain-injury detection and evaluation of zero-gravity brain trauma functionality.

It should be understood that appropriate hardware, software, or a combination of both hardware and software is provided to effect the processing described above, in the various embodiments of the invention. It should further be recognized that a particular embodiment might support one or more of the modes of operation described herein, but not necessarily all of these modes of operation.

It should be understood that various changes in the details, materials, and arrangements of the parts which have been described and illustrated in order to explain the nature of embodiments of the invention may be made by those skilled in the art without departing from the scope of the invention.

Embodiments of the present invention can take the form of methods and apparatuses for practicing those methods. Such embodiments can also take the form of program code embodied in tangible media, such as magnetic recording media, optical recording media, solid state memory, floppy diskettes, CD-ROMs, hard drives, or any other non-transitory machine-readable storage medium, wherein, when the program code is loaded into and executed by a machine, such as a computer, the machine becomes an apparatus for practicing embodiments of the invention. Embodiments of the invention can also be embodied in the form of program code, for example, stored in a non-transitory machine-readable storage medium including being loaded into and/or executed by a machine, wherein, when the program code is loaded into and executed by a machine, such as a computer, the machine becomes an apparatus for practicing embodiments of the invention. When implemented on a general-purpose processor, the program code segments combine with the processor to provide a unique device that operates analogously to specific logic circuits.

It will be appreciated by those skilled in the art that although the functional components of the exemplary embodiments of the system described herein may be embodied as one or more distributed computer program processes, data structures, dictionaries and/or other stored data on one or more conventional general-purpose computers (e.g., IBM-compatible, Apple Macintosh, and/or RISC microprocessor-based computers), mainframes, minicomputers, conventional telecommunications (e.g., modem, T1, fiber-optic line, DSL, satellite and/or ISDN communications), memory storage means (e.g., RAM, ROM) and storage devices (e.g., computer-readable memory, disk array, direct access storage) networked together by conventional network hardware and software (e.g., LAN/WAN network backbone systems and/or Internet), other types of computers and network resources may be used without departing from the present invention. One or more networks discussed herein may be a local area network, wide area network, internet, intranet, extranet, proprietary network, virtual private network, a TCP/IP-based network, a wireless network (e.g., IEEE 802.11 or Bluetooth), an e-mail based network of e-mail transmitters and receivers, a modem-based, cellular, or mobile telephonic network, an interactive telephonic network accessible to users by telephone, or a combination of one or more of the foregoing.

Embodiments of the invention as described herein may be implemented in one or more computers residing on a network transaction server system, and input/output access to embodiments of the invention may include appropriate hardware and software (e.g., personal and/or mainframe computers provisioned with Internet wide area network communications hardware and software (e.g., CQI-based, FTP, Netscape Navigator™, Mozilla Firefox™, Microsoft Internet Explorer™, Google Chrome™, or Apple Safari™ HTML Internet-browser software, and/or direct real-time or near-real-time TCP/IP interfaces accessing real-time TCP/IP sockets) for permitting human users to send and receive data, or to allow unattended execution of various operations of embodiments of the invention, in real-time and/or batch-type transactions. Likewise, a system consistent with the present invention may include one or more remote Internet-based servers accessible through conventional communications channels (e.g., conventional telecommunications, broadband communications, wireless communications) using conventional browser software (e.g., Netscape Navigator™, Mozilla Firefox™, Microsoft Internet Explorer™, Google Chrome™, or Apple Safari™). Thus, embodiments of the present invention may be appropriately adapted to include such communication functionality and Internet browsing ability. Additionally, those skilled in the art will recognize that the various components of the server system of the present invention may be remote from one another, and may further include appropriate communications hardware/software and/or LAN/WAN hardware and/or software to accomplish the functionality herein described.

Each of the functional components of embodiments of the present invention may be embodied as one or more distributed computer-program processes running on one or more conventional general purpose computers networked together by conventional networking hardware and software. Each of these functional components may be embodied by running distributed computer-program processes (e.g., generated using "full-scale" relational database engines such as IBM DB2™, Microsoft SQL Server™, Sybase SQL Server™, or Oracle 10g™ database managers, and/or a JDBC interface to link to such databases) on networked computer systems (e.g., including mainframe and/or symmetrically or massively-parallel computing systems such as the IBM SB2™ or HP 9000™ computer systems) including appropriate mass storage, networking, and other hardware and software for permitting these functional components to achieve the stated function. These computer systems may be geographically distributed and connected together via appropriate wide- and local-area network hardware and software. In one embodiment, data stored in the database or other program data may be made accessible to the user via standard SQL queries for analysis and reporting purposes.

Primary elements of embodiments of the invention may be server-based and may reside on hardware supporting an operating system such as Microsoft Windows NT/2000™ or UNIX.

Components of a system consistent with embodiments of the invention may include mobile and non-mobile devices. Mobile devices that may be employed in embodiments of the present invention include personal digital assistant (PDA) style computers, e.g., as manufactured by Apple Computer, Inc. of Cupertino, Calif., or Palm, Inc., of Santa Clara, Calif., and other computers running the Android, Symbian, RIM Blackberry, Palm webOS, or iPhone operating systems, Windows CE™ handheld computers, or other handheld computers (possibly including a wireless modem), as well as wireless, cellular, or mobile telephones (including GSM phones, J2ME and WAP-enabled phones, Internet-enabled phones and data-capable smart phones), one- and two-way paging and messaging devices, laptop computers, etc. Other telephonic network technologies that may be used as potential service channels in a system consistent with embodiments of the invention include 2.5G cellular network technologies such as GPRS and EDGE, as well as 3G technologies such as CDMA1×RTT and WCDMA2000, and 4G technologies. Although mobile devices may be used in embodiments of the invention, non-mobile communications devices are also contemplated by embodiments of the invention, including personal computers, Internet appliances, set-top boxes, landline telephones, etc. Clients may also include a PC that supports Apple Macintosh™, Microsoft Windows 95/98/NT/ME/CE/2000/XP/Vista/7/8™, a UNIX Motif workstation platform, or other computer capable of TCP/IP or other network-based interaction. In one embodiment, no software other than a web browser may be required on the client platform.

Alternatively, the aforesaid functional components may be embodied by a plurality of separate computer processes (e.g., generated via dBase™, Xbase™, MS Access™ or other "flat file" type database management systems or products) running on IBM-type, Intel Pentium™ or RISC microprocessor-based personal computers networked together via conventional networking hardware and software and including such other additional conventional hardware and software as may be necessary to permit these functional components to achieve the stated functionalities. In this alternative configuration, since such personal computers typically may be unable to run full-scale relational database engines of the types presented above, a non-relational flat file "table" (not shown) may be included in at least one of the networked personal computers to represent at least portions of data stored by a system according to embodiments of the present invention. These personal computers may run the Unix, Microsoft Windows NT/2000™, Windows 95/98/NT/ME/CE/2000/XP/Vista/7/8™, or OS X operating systems. The aforesaid functional components of a system according to the invention may also include a combination of the above two configurations (e.g., by computer program processes running on a combination of personal computers, RISC systems, mainframes, symmetric or parallel computer systems, and/or other appropriate hardware and software, networked together via appropriate wide- and local-area network hardware and software).

A system according to embodiments of the present invention may also be part of a larger system including multi-database or multi-computer systems or "warehouses" wherein other data types, processing systems (e.g., transaction, financial, medical, administrative, statistical, data extracting and auditing, data transmission/reception, and/or accounting support and service systems), and/or storage methodologies may be used in conjunction with those of the present invention to achieve additional functionality.

In one embodiment, source code may be written in an object-oriented programming language using relational databases. Such an embodiment may include the use of programming languages such as C++ and toolsets such as Microsoft's .Net™ framework. Other programming languages that may be used in constructing a system according to embodiments of the present invention include Java, HTML, Perl, UNIX shell scripting, assembly language, Fortran, Pascal, Visual Basic, and QuickBasic. Those skilled in the art will recognize that embodiments of the present invention may be implemented in hardware, software, or a combination of hardware and software.

Accordingly, the terms "server," "computer," and "system," as used herein, should be understood to mean a combination of hardware and software components including at least one machine having a processor with appropriate instructions for controlling the processor. The singular terms "server," "computer," and "system" should also be understood to refer to multiple hardware devices acting in concert with one another, e.g., multiple personal computers in a network; one or more personal computers in conjunction with one or more other devices, such as a router, hub, packet-inspection appliance, or firewall; a residential gateway coupled with a set-top box and a television; a network server coupled to a PC; a mobile phone coupled to a wireless hub; and the like. The term "processor" should be construed to include multiple processors operating in concert with one another.

It should also be appreciated from the outset that one or more of the functional components may alternatively be constructed out of custom, dedicated electronic hardware and/or software, without departing from the present invention. Thus, embodiments of the invention are intended to cover all such alternatives, modifications, and equivalents as may be included within the spirit and broad scope of the disclosure.

It should be understood that various changes in the details, materials, and arrangements of the parts which have been described and illustrated in order to explain the nature of this disclosure may be made by those skilled in the art without departing from the scope of the disclosure.

Reference herein to "one embodiment" or "an embodiment" means that a particular feature, structure, or characteristic described in connection with the embodiment can be included in at least one embodiment of the disclosure. The appearances of the phrase "in one embodiment" in various places in the specification are not necessarily all referring to the same embodiment, nor are separate or alternative embodiments necessarily mutually exclusive of other embodiments.

Although the disclosure is described herein with reference to specific embodiments, various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the disclosure.

Although the disclosure has been set forth in terms of the exemplary embodiments described herein and illustrated in the attached drawings, it is to be understood that such disclosure is purely illustrative and is not to be interpreted as limiting. Consequently, various alterations, modifications, and/or alternative embodiments and applications may be suggested to those skilled in the art after having read this disclosure. Accordingly, it is intended that the disclosure be interpreted as encompassing all alterations, modifications, or alternative embodiments and applications as fall within the true spirit and scope of this disclosure.

It will be further understood that various changes in the details, materials, and arrangements of the parts which have been described and illustrated in order to explain the nature of this disclosure may be made by those skilled in the art without departing from the scope of the disclosure as expressed in the following claims.

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

The invention claimed is:

1. A pupillometer comprising:
a testing compartment;
at least one ocular;
at least one camera; and
a computing device, wherein
the testing compartment comprises a plurality of chromatic beam emitters arranged about a visual field of the pupillometer,
selected ones of the plurality of chromatic beam emitters are structurally configured to generate chromatic stimuli within a blue portion of a visible electromagnetic spectrum,
selected ones of the plurality of chromatic beam emitters are structurally configured to generate chromatic stimuli within a red portion of the visible electromagnetic spectrum,
the at least one ocular is positioned to facilitate exposure of light sensitive ocular structures of an eye to blue and red chromatic stimuli of the plurality of chromatic beam emitters,
the at least one camera is configured to capture temporal images of a pupil of a subject, the temporal images indicating temporal pupil contraction of the eye in response to the blue and red chromatic stimuli of the plurality of chromatic beam emitters, and
the computing device is programed to
control emission wavelength, intensity, and duration of the plurality of chromatic beam emitters,
receive images from the at least one camera,
process the temporal images of the pupil captured by the at least one camera to generate a signal representative of the eye in response to the blue and red chromatic stimuli of the plurality of chromatic beam emitters, and
drive the plurality of chromatic beam emitters to generate chromatic stimuli within the blue and red portions of the visible electromagnetic spectrum such that red chromatic intensity is at least 2 times greater than blue chromatic stimuli intensity for generation of the signal.

2. The pupillometer of claim 1, wherein the red chromatic stimuli intensity is between about 2 and about 5 times greater than blue chromatic stimuli intensity.

3. The pupillometer of claim 1, wherein:
the red chromatic stimuli has a luminance between about 200 cd/m² and about 1000 cd/m²; and
an intensity of the red chromatic stimuli is between about 2 and about 5 times greater than the blue chromatic stimuli intensity.

4. The pupillometer of claim 1, wherein:
the emission wavelength of the blue chromatic stimuli has a peak value lying in a range from about 450 nm to about 490 nm; and
the emission wavelength of the red chromatic stimuli has a peak value lying in a range from about 620 nm to about 750 nm.

5. The pupillometer of claim 1, wherein:
the emission wavelength of the blue chromatic stimuli has a peak value lying in a range from about 480 nm to about 490 nm; and
the emission wavelength of the red chromatic stimuli has a peak value lying in a range from about 620 nm to about 630 nm.

6. The pupillometer of claim 1, wherein the plurality of chromatic beam emitters are driven to generate the red and blue chromatic stimuli throughout a substantial entirety of the visual field.

7. The pupillometer of claim 1, wherein the plurality of chromatic beam emitters is in a range of about 13 to about 256 chromatic beam emitters.

8. The pupillometer of claim 1, wherein the testing compartment is comprises a substantially hemisphere bowl and the plurality of chromatic beam emitters are arranged about the substantially hemisphere bowl.

9. The pupillometer of claim 1, wherein the computing device is programed to control the emission wavelength by selectively activating different ones of a set of red and blue chromatic beam emitters.

10. The pupillometer of claim 1, wherein the computing device is programed to activate selected ones of the chromatic beam emitters for a duration between about 0.1 seconds and about 10 seconds.

11. The pupillometer of claim 1, wherein:
the computing device is programed to generate emitter drive signals indicative of a wavelength within the blue or red portion of the visible electromagnetic spectrum, and
the computing device is programed to control the emission wavelength by changing the emitter drive signals between the blue and red portions of the visible electromagnetic spectrum.

12. A pupillometer comprising:
a computing device; and
a testing compartment comprising a plurality of chromatic beam emitters arranged about a visual field of the pupillometer, wherein
selected ones of the plurality of chromatic beam emitters are structurally configured to generate chromatic stimuli within a blue portion of a visible electromagnetic spectrum,
selected ones of the plurality of chromatic beam emitters are structurally configured to generate chromatic stimuli within a red portion of the visible electromagnetic spectrum, and
the computing device is programed to
control emission wavelength, intensity, and duration of the plurality of chromatic beam emitters,
process temporal images of a pupil to generate a signal representative of an eye in response to the blue and red chromatic stimuli of the plurality of chromatic beam emitters, and
drive the plurality of chromatic beam emitters to generate chromatic stimuli within the blue and red portions of the visible electromagnetic spectrum such that red chromatic intensity is at least 2 times greater than blue chromatic stimuli intensity for generation of the signal.

13. The pupillometer of claim 1, wherein the signal representative of the eye in response to the blue and red chromatic stimuli of the plurality of chromatic beam emitter is a time of maximum contraction velocity (TCV) signal.

14. The pupillometer of claim 12, wherein the signal representative of the eye in response to the blue and red chromatic stimuli of the plurality of chromatic beam emitter is a time of maximum contraction velocity (TCV) signal.

* * * * *

UNITED STATES PATENT AND TRADEMARK OFFICE
CERTIFICATE OF CORRECTION

PATENT NO. : 10,258,230 B2
APPLICATION NO. : 15/031842
DATED : April 16, 2019
INVENTOR(S) : Ygal Rotenstreich Page 1 of 1

It is certified that error appears in the above-identified patent and that said Letters Patent is hereby corrected as shown below:

On the Title Page

In page 2, Column 2, item (56), references cited, other publications (7), Line 21 delete "34rd" and insert --34th--, therefor.

In page 2, Column 2, item (56), references cited, other publications (8), Line 25 delete "34rd" and insert --34th--, therefor.

In page 2, Column 2, item (56), references cited, other publications (9), Line 29 delete "34rd" and insert --34th--, therefor.

In page 3, Column 1, item (56), references cited, other publications (5), Line 19 delete "perimetryin" and insert --perimetry in--, therefor.

In page 3, Column 2, item (56), references cited, other publications (2), Line 6 delete "primetry" and insert --perimetry--, therefor.

In page 3, Column 2, item (56), references cited, other publications (8), Line 24 delete "perimtry" and insert --perimetry--, therefor.

In the Drawings

In sheet 5, figure 3, above "(stage 302)", delete "Light adaptaion" and insert --Light adaptation--, therefor.

Signed and Sealed this
First Day of October, 2019

Andrei Iancu
*Director of the United States Patent and Trademark Office*